US012805800B2

(12) United States Patent
Levin et al.

(10) Patent No.: US 12,805,800 B2
(45) **Date of Patent: *Nov. 24, 2026**

(54) MANAGING FLUID LEVELS IN A PATIENT AND ASSOCIATED DEVICES, SYSTEMS, AND METHODS

(71) Applicant: REPRIEVE CARDIOVASCULAR, INC., Milford, MA (US)

(72) Inventors: Howard R. Levin, Teaneck, NJ (US); Jim Dillon, Milford, MA (US); Andrew Halpert, Brookline, MA (US); Jeffrey Testani, New Haven, CT (US)

(73) Assignee: REPRIEVE CARDIOVASCULAR, INC., Milford, MA (US)

( * ) Notice: Subject to any disclaimer, the term of this patent is extended or adjusted under 35 U.S.C. 154(b) by 344 days.

This patent is subject to a terminal disclaimer.

(21) Appl. No.: 18/595,182

(22) Filed: Mar. 4, 2024

(65) Prior Publication Data

US 2024/0197244 A1 Jun. 20, 2024

Related U.S. Application Data

(63) Continuation of application No. 18/296,292, filed on Apr. 5, 2023, now Pat. No. 11,950,925, which is a (Continued)

(51) Int. Cl.
*A61B 5/00* (2006.01)
*A61B 5/20* (2006.01)
*A61M 5/142* (2006.01)

(52) U.S. Cl.
CPC ............ *A61B 5/4839* (2013.01); *A61B 5/208* (2013.01); *A61M 5/142* (2013.01); (Continued)

(58) Field of Classification Search
CPC ........ A61M 5/1723; A61M 2202/0496; A61B 5/208; A61B 5/4836; A61B 5/4839
See application file for complete search history.

(56) References Cited

U.S. PATENT DOCUMENTS 3,954,010 A 5/1976 Hilblom
4,132,644 A 1/1979 Kolberg
(Continued)

FOREIGN PATENT DOCUMENTS

DE 4023336 A1 2/1992
DE 4137075 C2 11/1993
(Continued)

OTHER PUBLICATIONS

U.S. Appl. No. 16/544,975, filed Aug. 20, 2019, Levin.
(Continued)

*Primary Examiner* — William R Carpenter

(57) ABSTRACT

Devices, systems, and methods for delivering fluid therapy to a patient are disclosed herein. An exemplary method can comprise obtaining a urine output rate from a patient; causing a diuretic to be provided to the patient at a dosage rate, and increasing the dosage rate of the diuretic from the initial dosage rate to additional dosage rates higher than the initial dosage rate over a period of time. In some embodiments, the additional dosage rates include a first dosage rate higher than the initial dosage rate, a second dosage rate higher than the first dosage rate, and a third dosage rate higher than the second dosage rate.

20 Claims, 12 Drawing Sheets

Related U.S. Application Data continuation of application No. 17/806,681, filed on Jun. 13, 2022, now Pat. No. 11,627,912, which is a continuation of application No. 17/112,925, filed on Dec. 4, 2020, now Pat. No. 11,357,446.

(60) Provisional application No. 62/945,058, filed on Dec. 6, 2019.

(52) U.S. Cl.
CPC ............. *A61M 2005/14208* (2013.01); *A61M 2202/0496* (2013.01); *A61M 2205/3327* (2013.01); *A61M 2205/3396* (2013.01); *A61M 2205/50* (2013.01)

(56) References Cited

U.S. PATENT DOCUMENTS

| | | | | |
|---|---|---|---|---|
| 4,146,029 | A | 3/1979 | Ellinwood, Jr. | |
| 4,204,957 | A | 5/1980 | Weickhardt | |
| 4,216,462 | A | 8/1980 | McGrath et al. | |
| 4,229,299 | A | 10/1980 | Savitz et al. | |
| 4,261,360 | A | 4/1981 | Perez | |
| 4,275,726 | A | 6/1981 | Schael | |
| 4,291,692 | A | 9/1981 | Bowman et al. | |
| 4,343,316 | A | 8/1982 | Jespersen | |
| 4,411,649 | A | 10/1983 | Kamen | |
| 4,448,207 | A | 5/1984 | Parrish | |
| 4,449,538 | A | 5/1984 | Corbitt et al. | |
| 4,504,263 | A | 3/1985 | Steuer et al. | |
| 4,658,834 | A | 4/1987 | Blankenship et al. | |
| 4,712,567 | A | 12/1987 | Gille et al. | |
| 4,728,333 | A | 3/1988 | Masse et al. | |
| 4,728,433 | A | 3/1988 | Buck et al. | |
| 4,745,929 | A | 5/1988 | Silver | |
| 4,813,925 | A | 3/1989 | Anderson, Jr. et al. | |
| 4,923,598 | A | 5/1990 | Schal | |
| 4,994,026 | A | 2/1991 | Fecondini | |
| 5,038,109 | A | 8/1991 | Goble | |
| 5,098,379 | A | 3/1992 | Conway et al. | |
| 5,176,148 | A | 1/1993 | Wiest et al. | |
| 5,179,862 | A | 1/1993 | Lynnworth | |
| 5,207,642 | A | 5/1993 | Orkin et al. | |
| 5,573,506 | A | 11/1996 | Vasko | |
| 5,586,973 | A | 12/1996 | Lemaire et al. | |
| 5,709,670 | A | 1/1998 | Vancaillie et al. | |
| 5,722,947 | A | 3/1998 | Jeppsson et al. | |
| 5,769,087 | A | 6/1998 | Westphal et al. | |
| 5,814,009 | A | 9/1998 | Wheatman | |
| 5,891,051 | A | 4/1999 | Han et al. | |
| 5,910,252 | A | 6/1999 | Truitt et al. | |
| 5,916,153 | A | 6/1999 | Rhea, Jr. | |
| 5,916,195 | A | 6/1999 | Eshel et al. | |
| 5,981,051 | A | 11/1999 | Motegi et al. | |
| 5,984,893 | A | 11/1999 | Ward | |
| 6,010,454 | A | 1/2000 | Arieff et al. | |
| 6,171,253 | B1 | 1/2001 | Bullister et al. | |
| 6,231,551 | B1 | 5/2001 | Barbut | |
| 6,272,930 | B1 | 8/2001 | Crozafon | |
| 6,514,226 | B1 | 2/2003 | Levin et al. | |
| 6,531,551 | B2 | 3/2003 | Ohno et al. | |
| 6,537,244 | B2 | 3/2003 | Paukovits et al. | |
| 6,554,791 | B1 | 4/2003 | Cartledge et al. | |
| 6,640,649 | B1 | 11/2003 | Paz et al. | |
| 6,740,072 | B2 | 5/2004 | Starkweather et al. | |
| 6,752,779 | B2 | 6/2004 | Paukovits et al. | |
| 6,796,960 | B2 | 9/2004 | Cioanta et al. | |
| 6,827,702 | B2 | 12/2004 | Lebel et al. | |
| 6,942,637 | B2 | 9/2005 | Cartledge et al. | |
| 7,029,456 | B2 | 4/2006 | Ware et al. | |
| 7,044,002 | B2 | 5/2006 | Ericson et al. | |
| 7,086,615 | B2 | 8/2006 | Joseph | |
| 7,137,964 | B2 | 11/2006 | Flaherty | |
| 7,278,983 | B2 | 10/2007 | Ireland et al. | |
| 7,727,222 | B2 | 6/2010 | Da Silva | |
| 7,736,354 | B2 | 6/2010 | Gelfand | |
| 7,739,921 | B1 | 6/2010 | Babcock | |
| 7,758,562 | B2 | 7/2010 | Gelfand | |
| 7,758,563 | B2 | 7/2010 | Gelfand | |
| 7,837,667 | B2 | 11/2010 | Gelfand | |
| 7,938,817 | B2 | 5/2011 | Gelfand | |
| 8,007,460 | B2 | 8/2011 | Gelfand | |
| 8,075,513 | B2 | 12/2011 | Rudko et al. | |
| 8,233,957 | B2 | 7/2012 | Merz et al. | |
| 8,444,623 | B2 | 5/2013 | Gelfand | |
| 8,556,846 | B2 | 10/2013 | O'Mahony et al. | |
| 8,714,030 | B1 | 5/2014 | Liu | |
| 9,526,833 | B2 | 12/2016 | Gelfand et al. | |
| 10,045,734 | B2 | 8/2018 | Da Silva | |
| 10,537,281 | B2 | 1/2020 | Thompson et al. | |
| 10,639,419 | B2 | 5/2020 | Halpert | |
| 10,881,774 | B2 | 1/2021 | Halpert | |
| 11,064,939 | B2 | 7/2021 | Da Silva | |
| 11,213,621 | B2 | 1/2022 | Halpert | |
| 11,357,446 | B2 * | 6/2022 | Levin | G16H 20/17 |
| 11,627,912 | B2 | 4/2023 | Levin et al. | |
| 11,633,137 | B2 | 4/2023 | Conley et al. | |
| 11,696,985 | B2 | 7/2023 | Halpert | |
| 11,986,302 | B2 | 5/2024 | Conley et al. | |
| 11,992,332 | B2 | 5/2024 | Da Silva | |
| 2001/0029340 | A1 | 10/2001 | Mault et al. | |
| 2002/0025597 | A1 | 2/2002 | Matsuda | |
| 2002/0072647 | A1 | 6/2002 | Schock et al. | |
| 2002/0107536 | A1 | 8/2002 | Hussein | |
| 2002/0151834 | A1 | 10/2002 | Utterberg | |
| 2002/0161314 | A1 | 10/2002 | Sarajarvi | |
| 2003/0040700 | A1 | 2/2003 | Hickle | |
| 2003/0048185 | A1 | 3/2003 | Citrenbaum et al. | |
| 2003/0048432 | A1 | 3/2003 | Jeng et al. | |
| 2003/0114786 | A1 | 6/2003 | Hiller et al. | |
| 2004/0025597 | A1 | 2/2004 | Ericson et al. | |
| 2004/0059295 | A1 | 3/2004 | Cartledge et al. | |
| 2004/0073177 | A1 | 4/2004 | Hickle | |
| 2004/0081585 | A1 | 4/2004 | Reid | |
| 2004/0087894 | A1 | 5/2004 | Flaherty | |
| 2004/0122353 | A1 | 6/2004 | Shahmirian et al. | |
| 2004/0133187 | A1 | 7/2004 | Hickle | |
| 2004/0163655 | A1 | 8/2004 | Gelfand et al. | |
| 2004/0167415 | A1 | 8/2004 | Gelfand et al. | |
| 2004/0167464 | A1 | 8/2004 | Ireland et al. | |
| 2004/0176703 | A1 | 9/2004 | Christensen et al. | |
| 2004/0193328 | A1 | 9/2004 | Zaitsu et al. | |
| 2004/0243075 | A1 | 12/2004 | Harvie | |
| 2005/0027254 | A1 | 2/2005 | Vasko | |
| 2005/0065464 | A1 | 3/2005 | Talbot et al. | |
| 2005/0085760 | A1 | 4/2005 | Ware et al. | |
| 2005/0119626 | A1 | 6/2005 | Rahe-Meyer | |
| 2006/0052764 | A1 | 3/2006 | Gelfand et al. | |
| 2006/0064053 | A1 | 3/2006 | Bollish et al. | |
| 2006/0100743 | A1 | 5/2006 | Townsend et al. | |
| 2006/0184084 | A1 | 8/2006 | Ware et al. | |
| 2006/0235353 | A1 | 10/2006 | Gelfand et al. | |
| 2006/0253064 | A1 | 11/2006 | Gelfand et al. | |
| 2006/0270971 | A1 | 11/2006 | Gelfand et al. | |
| 2007/0055198 | A1 | 3/2007 | O'Mahony et al. | |
| 2007/0088333 | A1 | 4/2007 | Levin et al. | |
| 2007/0258838 | A1 | 11/2007 | Drake et al. | |
| 2008/0027409 | A1 | 1/2008 | Rudko et al. | |
| 2008/0033394 | A1 | 2/2008 | Gelfand et al. | |
| 2008/0051764 | A1 | 2/2008 | Dent et al. | |
| 2008/0171966 | A1 | 7/2008 | Rudko et al. | |
| 2008/0221512 | A1 | 9/2008 | Da Silva et al. | |
| 2009/0054745 | A1 | 2/2009 | Jennewine | |
| 2009/0062727 | A1 | 3/2009 | Woo | |
| 2009/0062730 | A1 | 3/2009 | Woo | |
| 2010/0133510 | A1 | 6/2010 | Kim et al. | |
| 2010/0185175 | A1 | 7/2010 | Kamen | |
| 2010/0274217 | A1 | 10/2010 | Da Silva et al. | |
| 2010/0280443 | A1 | 11/2010 | Gelfand et al. | |
| 2010/0280444 | A1 | 11/2010 | Gelfand et al. | |
| 2010/0286559 | A1 | 11/2010 | Paz et al. | |
| 2010/0312039 | A1 | 12/2010 | Quirico | |
| 2011/0046514 | A1 | 2/2011 | Greenwald et al. | |
| 2011/0046516 | A1 | 2/2011 | Paz et al. | |

(56) References Cited

U.S. PATENT DOCUMENTS

| | | | |
|---|---|---|---|
| 2011/0106004 | A1 | 5/2011 | Eubanks et al. |
| 2011/0120231 | A1 | 5/2011 | Berger |
| 2011/0196304 | A1 | 8/2011 | Kramer et al. |
| 2011/0218411 | A1 | 9/2011 | Keenan |
| 2011/0288524 | A1 | 11/2011 | Gelfand et al. |
| 2012/0078137 | A1 | 3/2012 | Mendels |
| 2012/0259308 | A1 | 10/2012 | Gelfand |
| 2013/0104667 | A1 | 5/2013 | Koyano |
| 2013/0235691 | A1 | 9/2013 | Volker |
| 2013/0261412 | A1 | 10/2013 | Reed |
| 2013/0267892 | A1 | 10/2013 | Woolford |
| 2013/0274705 | A1 | 10/2013 | Burnes et al. |
| 2013/0304027 | A1 | 11/2013 | Haddad et al. |
| 2014/0031787 | A1 | 1/2014 | Burnes et al. |
| 2014/0073973 | A1 | 3/2014 | Sexton |
| 2014/0163487 | A1 | 6/2014 | Tout et al. |
| 2014/0228755 | A1 | 8/2014 | Darrah et al. |
| 2014/0260600 | A1 | 9/2014 | Rike |
| 2014/0366641 | A1 | 12/2014 | Jedema et al. |
| 2015/0025468 | A1 | 1/2015 | Grandolfo |
| 2015/0105694 | A1 | 4/2015 | Mahajan |
| 2015/0204860 | A1 | 7/2015 | Chui |
| 2015/0233749 | A1 | 8/2015 | Wang et al. |
| 2015/0258277 | A1 | 9/2015 | Halpert et al. |
| 2016/0051176 | A1 | 2/2016 | Ramos et al. |
| 2016/0051750 | A1 | 2/2016 | Tsoukalis |
| 2016/0136356 | A1 | 5/2016 | Ribble et al. |
| 2017/0016755 | A1 | 1/2017 | Boussange et al. |
| 2017/0052056 | A1 | 2/2017 | Yamasaki et al. |
| 2017/0290974 | A1 | 10/2017 | Tsoukalis |
| 2018/0071455 | A9 | 3/2018 | Halpert |
| 2018/0110455 | A1 | 4/2018 | Chang et al. |
| 2018/0177945 | A1 | 6/2018 | Sims et al. |
| 2018/0245967 | A1 | 8/2018 | Parker et al. |
| 2018/0250461 | A1 | 9/2018 | Gura |
| 2018/0280620 | A1 | 10/2018 | Reichthalhammer |
| 2019/0001057 | A1 | 1/2019 | Tsoukalis |
| 2019/0038833 | A1 | 2/2019 | Pirazzoli et al. |
| 2019/0046102 | A1 | 2/2019 | Kushnir et al. |
| 2019/0262532 | A1 | 8/2019 | Oh et al. |
| 2019/0321588 | A1 | 10/2019 | Burnett |
| 2020/0061273 | A1 | 2/2020 | Hogard et al. |
| 2020/0230351 | A1 | 7/2020 | Kelly et al. |
| 2020/0284234 | A1 | 9/2020 | Huberts et al. |
| 2020/0297900 | A1 | 9/2020 | Holigan et al. |
| 2020/0324044 | A1 | 10/2020 | Gylland et al. |
| 2020/0360604 | A1 | 11/2020 | Kolko et al. |
| 2020/0405955 | A1 | 12/2020 | Shah et al. |
| 2021/0024536 | A1 | 1/2021 | Bhattacharya |
| 2021/0077007 | A1 | 3/2021 | Jouret et al. |
| 2021/0085853 | A1 | 3/2021 | Chen et al. |
| 2021/0128815 | A1 | 5/2021 | Byrne et al. |
| 2021/0162188 | A1 | 6/2021 | Cui |
| 2021/0169408 | A1 | 6/2021 | Levin |
| 2021/0170084 | A1 | 6/2021 | Zacharia |
| 2021/0196880 | A1 | 7/2021 | O'Mahony et al. |
| 2021/0236727 | A1 | 8/2021 | Levin et al. |
| 2021/0244381 | A1 | 8/2021 | Sweeney et al. |
| 2021/0260306 | A1 | 8/2021 | Gravenstein et al. |
| 2021/0283357 | A1 | 9/2021 | Leonard |
| 2021/0298653 | A1 | 9/2021 | Woodward et al. |
| 2021/0369959 | A1 | 12/2021 | Abal et al. |
| 2022/0152302 | A1 | 5/2022 | Halpert |
| 2022/0273213 | A1 | 9/2022 | Sokolov |
| 2022/0288362 | A1 | 9/2022 | Porter et al. |
| 2022/0296140 | A1 | 9/2022 | Nguyen et al. |
| 2022/0296406 | A1 | 9/2022 | Keelen |
| 2022/0313158 | A1 | 10/2022 | Levin et al. |
| 2022/0330866 | A1 | 10/2022 | Conley et al. |
| 2022/0330867 | A1 | 10/2022 | Conley et al. |
| 2022/0339622 | A1 | 10/2022 | Halpert |
| 2023/0010793 | A1 | 1/2023 | Testani |
| 2023/0068431 | A1 | 3/2023 | Erbey, II et al. |
| 2023/0240600 | A1 | 8/2023 | Levin et al. |
| 2023/0414871 | A1 | 12/2023 | Halpert |
| 2024/0260874 | A1 | 8/2024 | Halpert |
| 2024/0269382 | A1 | 8/2024 | Uemura et al. |
| 2024/0347162 | A1 | 10/2024 | Meese et al. |

FOREIGN PATENT DOCUMENTS

| | | | |
|---|---|---|---|
| EP | 0258690 | | 3/1998 |
| EP | 1986007 | | 10/2008 |
| EP | 3278833 | | 2/2018 |
| EP | 4108171 | | 12/2022 |
| GB | 2560580 | | 9/2018 |
| JP | 2008110150 | | 5/2008 |
| JP | 2010503515 | | 2/2010 |
| JP | A-2011-520549 | | 7/2011 |
| JP | A-2017-536857 | | 2/2017 |
| KR | 10-2022-0035738 | | 3/2022 |
| WO | WO-1996016685 | | 6/1996 |
| WO | WO-1996028209 | | 9/1996 |
| WO | WO-1997016220 | | 5/1997 |
| WO | WO-1999006087 | | 2/1999 |
| WO | WO-2005102441 | | 11/2005 |
| WO | WO-2006041496 | | 4/2006 |
| WO | 2009029899 | A1 | 3/2009 |
| WO | 2013154783 | A1 | 10/2013 |
| WO | WO-2014022422 | | 2/2014 |
| WO | 2015142617 | A1 | 9/2015 |
| WO | WO-2016103256 | | 6/2016 |
| WO | 2018044959 | A1 | 3/2018 |
| WO | WO-2018114794 | | 6/2018 |
| WO | 2019222485 | A1 | 11/2019 |
| WO | WO-2020033752 | | 2/2020 |
| WO | 2021205345 | | 10/2021 |
| WO | WO-2022219578 | | 10/2022 |
| WO | 2022259115 | A1 | 12/2022 |
| WO | 2024013731 | A1 | 1/2024 |

OTHER PUBLICATIONS

U.S. Appl. No. 18/434,540, filed Feb. 6, 2024, Halpert.

U.S. Appl. No. 18/637,340, filed Apr. 16, 2024, Conley et al.

U.S. Appl. No. 18/641,241, filed Apr. 19, 2024, Da Silva.

"2016 ESC Guidelines for the Diagnosis and Treatment of Acute and Chronic Heart Failure—Web Addenda," European Heart Journal, 17 pages.

Adams et al., "Executive Summary: HFSA 2006 Comprehensive Heart Failure Practice Guideline," Journal of Cardiac Failure, vol. 12, No. 1, 2006, pp. 10-38.

Adaptec Medical Devices, "Ongoing Access To Real-Time And Accurate Monitoring Of Urine Output Could Improve Management Of Critically Ill Patients," Clinical Literature Review, (2016) 8 pages.

Bell et al., "Risk of Postoperative Acute Kidney Injury in Patients Undergoing Orthopaedic Surgery—Development and Validation of Risk score and Effect of Acute Kidney Injury on Survival: Observational Cohort Study," BMJ: 2015, 9 pages.

Bouman et al., "Red Blood Cell Transfusion and Furosemide in Cardiac Surgery: Friend and Foe?" The Netherlands Journal of Medicine, Dec. 2012, vol. 70, No. 10, 3 pages.

Cosgrove III et al., "Automated Control Postoperative Hypertension: A Prospective Randomized Multicenter Study," 1989 by The Society of Thoracic Surgeons, 6 pages.

Farcy, "Review: Pitfalls in Using Central Venous Pressure as a Marker of Fluid Responsiveness," Emergency Medicine. Jan. 2016;48(1):18-28, 15 pages.

Furutani et al., "An Automatic Control System of the Blood Pressure of Patients Under Surgical Operation," International Journal of Control, Automation, and Systems, vol. 2, No. 1, Mar. 2004, pp. 39-54.

Gheorghiade et al., "Current Medical Therapy for Advanced Heart Failure," American Heart Journal, Jun. 1998, pp. S231-S248.

Goren et al., "Perioperative Acute Kidney Injury," British Journal of Anaesthesia, 2015, 12 pages.

Josephs et al., "Perioperative Risk Assessment, Prevention, and Treatment of Acute Kidney Injury," International Anesthesiology Clinics, vol. 47, No. 4, www.anesthesiaclinics.com, pp. 89-105.

(56) References Cited

OTHER PUBLICATIONS

Kambiz Kalantari, "Assessment Of Intravascular Volume Status And Volume Responsiveness In Critically Ill Patients," Kidney International (2013) 83, 1017-1028 (Jan. 9, 2013) 12 pages.
Kolh, "Renal Insufficiency After Cardiac Surgery: A Challenging Clinical Problem," European Heart Journal, 2009, pp. 1824-1827.
Kui Jin et al., "Intensive Monitoring of Urine Output Is Associated With Increased Detection of Acute Kidney Injury and Improved Outcomes," Chest Journal—Original Research Critical Care, 152#5, pp. 972-979 (Nov. 2017) 8 pages.
Lara, "Accurate Monitoring Of Intravascular Fluid Volume: A Novel Application Of Intrathoracic Impedance Measures For The Guidance Of Volume Reduction Therapy," IJC Heart & Vasculature, 8 (2015) pp. 47-51, 5pages.
Lassnigg et al., "Lack of Renoprotective Effects of Dopamine and Furosemide During Cardiac Surgery," J. Am Soc Nephrol, 2000, pp. 97-104.
Lenihan et al., "Trends in Acute Kidney Injury, Associated Use of Dialysis and Mortality After Cardiac Surgery, 1999 to 2008," Ann Thorac Surg. 2013, 17 pages.
Magder et al., "The Clinical Role of Central Venous Pressure Measurements", Journal of Intensive Care Medicine 22(1); 207, 8 pages.
Mayo Clinic, "Creatinine Test", Mayo Foundation for Medical Education and Research (MFMER) (downloaded Aug. 16, 2018).
Meersch et al., "Perioperative Acute Kidney Injury: An Under-Recognized Problem," vol. 125, No. 4, www.anesthesia-analgesia.org, Oct. 2017, pp. 1223-1232.
Olivero et al., "Acute Kidney Injury After Cardiovascular Surgery: An Overview," debakeyheartcenter.com/journal, 2012, pp. 31-36.
Otero, "A New Device to Automate the Monitoring of Critical Patients' Urine Output", Hindawi Publishing Corp, BioMed Research Int'l, vol. 2014, Article ID 587593, 8 pages.
Rosenberg et al., "Combination Therapy with Metolazone and Loop Diuretics in Outpatients with Refactory Heart Failure: An Observational Study and Review of the Literature," Cardiovascular Drugs and Therapy, Kluwer Academic Publishers, vol. 19, No. 4, Aug. 2005, 6 pages.
Rui Geng et al., "Identification of Modifiable Risk Factors for Acute Kidney Injury After Coronary Artery Bypass Graft Surgery in an Asian Population," The Journal of Thoracic and Cardiovascular Surgery, Apr. 2014, pp. 1356-1361.
Se Won Oh et al., "Loop Diuretics In Clinical Practice", Electrolytes & Blood Pressure, www.ncbi.nlm.nih.gov/pmc/articles/PMC4520883, printed Mar. 25, 2019, 6 pages.
Shepherd, "Measuring and Managing Fluid Balance", Nursing Times, vol. 107, No. 28, pp. 12-16 (Jul. 19, 2011) 5 pages.
Stickler et al., "A Sensor To Detect the Early Stages in the Development of Crystalline Proteus mirabilis Biofilm on Indwelling Bladder Catheters", Journal of Clinical Microbiology, Apr. 2006, p. 1540-1542.
Teixeira et al., "Fluid Balance and Urine Volume are Independent Predictors of Mortality in Acute Kidney Injury", Critical Care 17:R14 (2013) 11 pages.
Testani et al., "Rapid and Highly Accurate Prediction of Poor Loop Diuretic Natriuretic Response in Patients with Heart Failure," Circulation; Heart Failure, vol. 9. No. 1, 2016, 32 pages.
Thakar, "Perioperative Acute Kidney Injury," Advances in Chronic Kidney Disease, vol. 20, No. 1, 2013, pp. 67-75.
Tricoli, "Miniaturized Bio-and Chemical-Sensors for Point-of-Care Monitoring of Chronic Kidney Diseases," Sensors 2018, 18, 942; (Mar. 22, 2018) 18 pages.
Vellinga et al., "Identification of Modifiable Risk Factors for Acute Kidney Injury After Cardiac Surgery," The Netherlands Journal of Medicine, vol. 70, No. 10, Dec. 2012, pp. 450-454.
Vivane Conradds, "Sensitivity And Positive Predictive Value Of Implantable Intrathoracic Impedance Monitoring As A Predictor Of Heart Failure Hospitalizations: The SENSE-HF Trial," European Heart Journal (2011) 32, 2266-2273, 8pages.
Written Opinion of the International Searching Authority for PCT Application No. PCT/US2005/008948 dated Oct. 3, 2006, 3 pages.
Written Opinion of the International Searching Authority for PCT Application No. PCT/US2007/021791 dated May 8, 2008, 7 pages.
Written Opinion of the International Searching Authority for PCT Application No. PCT/U20S07/009685 dated Jul. 18, 2008, 10 pages.
Written Opinion of the International Searching Authority for PCT Application No. PCT/US2007/009684 dated Jul. 21, 2008, 7 pages.
Written Opinion of the International Searching Authority for PCT Application No. PCT/US2008/007845 dated Sep. 17, 2008, 5 pages.
Written Opinion of the International Searching Authority for PCT Application No. PCT/US2008/007841 dated Sep. 18, 2008 4 pages.
Written Opinion of the International Searching Authority for PCT Application No. PCT/US2007/009683 dated Nov. 24, 2008, 6 pages.
Written Opinion of the International Searching Authority for PCT Application No. PCT/US2009/002739 dated Jun. 19, 2009, 4 pages.
Written Opinion of the International Searching Authority for PCT Application No. PCT/US2010/000137 dated Mar. 16, 2010, 8 pages.
Written Opinion of the International Searching Authority for PCT Application No. PCT/US2015/020196, dated Jun. 12, 2015, 5 pages.
Bart et al., "Ultrafiltration in Decompensated Heart Failure With Cardiorenal Syndrome", The New England Journal of Medicine, Dec. 13, 2012, 9 pages, Massachusetts Medical Society.
Brezis et al., Hypoxia of the Renal Medulla—Its Implications for Disease, New England Journal of Medicine, vol. 322, No. 10, Mar. 9, 1995, 9 pages.
Briguori et al., "Renal Insufficiency After Contrast Media Administration Trial II (REMEDIAL II): RenalGuard System in High-Risk Patients for Contrast-Induced Acute Kidney Injury", Circulation, Journal of the American Heart Association, Mar. 13, 2011, 10 pages.
Dorval et al., "Feasibility Study of the RenalGuard™ Balanced Hydration System: A Novel Strategy for the Prevention of Contrast-Induced Nephropathy in High Risk Patients", International Journal of Cardiology, 2011, 5 pages, Elsevier Ireland Ltd.
Edelson et al., Pharmacokinetics of lohexol, a New Nonionic Radiocontrast Agent, in Humans, Journal of Pharmaceutical Sciences, vol. 73, No. 7, Jul. 1984, 3 pages.
Felker et al., "Diuretic Strategies in Patients With Acute Decompensated Heart Failure", The New England Journal of Medicine, Mar. 3, 2011, vol. 364, No. 9, 9 pages.
Gloor, James M. and Vincente E. Torres, Reflux and Obstructive Nephropathy, Atlas of Diseases of the Kidney, on-line edition, vol. Two, Section I, Ch. 8, pp. 8.1-8.25, 1999, 27 pages.
Hvistendahl et al., Renal Hemodynamic Response to Gradated Ureter Obstruction in the Pig, Nephron 1996, 74:168-74, 7 pages.
Lelarge et al., Acute Unilateral Renal Failure and Contralateral Ureteral Obstruction, American Journal of Kidney Diseases, vol. XX, No. 3, Sep. 1992, 3 pages.
Levin et al. High-volume diuresis with matched maintenance of intravascular volume may prevent contrast-induced nephropathy in post-transplant patients with moderate-severe baseline renal impairment, Cardiovascular Revascularization Medicine, Elsevier, NL, vol. 8, No. 2, Apr. 1, 2007, 1 page.
Lloyd-Jones et al., "Heart Disease and Stroke Statistics—2009 Update. A Report From the American Heart Association Statistics Committee and Stroke Statistics Subcommittee", Circulation, Journal of the American Heart Association, Jan. 27, 2009, 161 pages.
Marenzi et al . . . "Prevention of Contrast Nephropathy by Furosemide With matched Hydration. The MYTHOS (Induced Diuresis With Matched Hydration Compared to Standard Hydration for Contrast Induced Nephropathy Prevention) Trial", JACC: Cardiovascular Interventions, vol. 5, No. 1, 2012 The American College of Cardiology Foundation, 8 pages.
Mawer et al., "Value of Forced Diuresis in Acute Barbiturate Poisoning", Jun. 29, 1968, British Medical Journal, 2, 4 pages.
Paterna et al., "Changes in Brain Natriuretic Peptide Levels and Bioelectrical Impedance Measurements After Treatment With High-Dose Furosemide and Hypertonic Saline Solution Versus High-

(56) References Cited

OTHER PUBLICATIONS

Dose Furosemide Alone in Refractory Congestive Heart Failure", Journal of the American College of Cardiology, 2005, vol. 45, No. 12, 7 pages.
Pederson et al., Renal Water and Sodium Handling During Gradated Unilateral Ureter Obstruction, Scand J. Urol Nephrol, 2002, 36:163-72, 11 pages.
Rihal et al., Incidence and Prognostic Importance of Acute Renal Failure After Percutaneous Coronary Intervention, Circulation, May 14, 2002, 6 pages.
Rosamilia et al., Electromotive Drug Administration of Lidocaine and Dexamethasone Followed by Cystodistension in Women with Interstitial Cystitis, International Urogyecologyl Journal, Pelvic Floor Dysfunction 1997; 8: 142-5, 4 pages.
S215 Ultra Low Profile Single Point Load Cell—Strain Guage Sensors and Load Cells, Ultra-Low Profile Single Point Load Cell—S215, http://smdsensors.com/detail_pgs/s215.htm 2005, 3 pages.
Solomon et al., Effects of Saline, Mannitol, and Furosemide on Acute Decreases in Renal Function Induced by Radiocontrast Agents, The New England Journal of Medicine, vol. 331: 1416-1420, Nov. 24, 1994, No. 21, 5 pages.
Stevens, Melissa A., MD et al., A Prospective Randomized Trial of Prevention Measures in Patients at High Risk for Contrast Nephropathy, Results of the P.R.I.N.C.E. Study, Journal of American College of Cardiology, vol. 33, No. 2, Feb. 1999, 9 pages.
Stevenson et al., "Editorial Comment, Torrent or Torment From the Tubules?", Challenge of the Cardiorenal Connections, Journal of the American College of Cardiology, vol. 45, No. 12, 2005, 4 pages.
Wakelkamp et al., The influence of drug input rate on the development of tolerance to frusemide, Br. J. Clin. Pharmacol 1998, 46:479-487, 9 pages.
Weinstein et al., Potential deleterious Effect of Furosmide in Radiocontrast Nephropathy, Department of Medicine, Hadassah Univeristy Hospital, Mount Scopus, Jerusalem, Israel, Nephron 1992, 62: 413-415, pages.
Doty et al., Effect of Increased Renal Venous Pressure on Renal Function, The Journal of Trauma: Injury, Infection and Critical Care, vol. 47, No. 6, Dec. 1999, 4 pages.
Heyman et al., Pathophysiology of Radiocontrast Nephropathy: A Role for Medullary Hypoxia, Investigative Radiology, vol. 34, No. 11, Nov. 1999, 7 pages.
Felker et al., "Diuretic Therapy for Heart Failure Patients," American College of Cardiology, Mar. 9, 2020, 4 pages.
Phillips et al., "Measurement of sodium ion concentration in undiluted urine with cation-selective polymeric membrane electrodes after the removal of interfering compounds", Talanta, Elsevier, Amsterdam, NL, vol. 74, No. 2, Nov. 15, 2007, pp. 255-264.
Allen et al., "Continuous Versus Bolus Dosing of Furosemide for Patients Hospitalized for Heart Failure," American Journal of Cardiology, 105(12):1794-1794, 2010.
Brater, "Diuretic Therapy," New England Journal of Medicine, 339:387-395, 1998.
Baliga, "Diuretic Therapy for Heart Failure Patients," American College of Cardiology, 75:1178-1195, 2020.
Ellison et al., "Diuretic Treatment in Heart Failure," New England Journal of Medicine, 377:1964-1975, 2017.
Farkas, "Deresuscitation: Dominating the Diuresis," The Internet Book of Critical Care, 43 pages, 2020.
Hasselblad et al., "Relation Between Dose of Loop Diuretics and Outcomes in a Heart Failure Population: Results of the ESCAPE Trial", European Journal of Heart Failure, 9(10):1064-1069, 2007.
Marenzi et al., "Prevention of Contrast Nephropathy by Furosemide With Matched Hydration," JACC: Cardiovascular Interventions, 5(1):90-97, 2011.
Mendeley et al., "Furosemide", Science Direct, 5 pages, 2016.
Oh et al., "Loop Diuretics in Clinical Practice," Electrolyte Blood Press, 13(1):17-21, 2015.
Palazzuli et al. "Continuous versus bolus intermittent loop diuretic infusion in acutely decompensated heart failure: a prospective randomized trial," Critical Care 18, 2014.
Prandota et al., "Pharmacokinetics and metabolism of furosemide in man," European Journal of Drug Metabolism and Pharmcokinetics, 1(4):177-181, 1976.
PCT Search Report and Written Opinion, Appl. No. PCT/US20/63487, dated Mar. 19, 2021, 19 pages.
Unknown Author, "Furosemide Drug Summary," Prescriber's Digital Reference, pp. 1-31, 2016.
Yeh et al., "Goal-directed diuresis: A case—control study of continuous furosemide infusion in critically ill trauma patients", The Journal of Emergencies, Trauma, and Shock, 8(1): 34-38, 2015.

* cited by examiner

MANAGING FLUID LEVELS IN A PATIENT AND ASSOCIATED DEVICES, SYSTEMS, AND METHODS

CROSS-REFERENCE TO RELATED APPLICATIONS

The present application is a continuation of U.S. patent application Ser. No. 18/296,292, filed Apr. 5, 2023, now U.S. Pat. No. 11,950,925, which is a continuation of U.S. patent application Ser. No. 17/806,681, filed Jun. 13, 2022, now U.S. Pat. No. 11,627,912, which is a continuation of U.S. patent application Ser. No. 17/112,925, filed Dec. 4, 2020, now U.S. Pat. No. 11,357,446, which claims priority to U.S. Provisional Application No. 62/945,058, filed Dec. 6, 2019, the disclosures of which are incorporated herein by reference in their entireties.

TECHNICAL FIELD

The present disclosure relates to methods, devices, systems, and algorithms for managing patient fluid levels and, in particular embodiments, treating fluid overload conditions for patients with heart failure.

BACKGROUND

Physiological systems in humans seek to naturally maintain a balance between fluids ingested and fluids that are excreted. When there is an imbalance of fluids, a patient may suffer from fluid overload in which an excessive amount of fluid is retained. Patients may be in a fluid overloaded condition due to acute decompensated heart failure (ADHF), chronic heart failure (CHF) or other conditions in which insufficient fluid is excreted to avoid fluid overload in the body. Patients in fluid overload may suffer from shortness of breath (called dyspnea), edema, hypertension and other undesirable medical conditions that are symptoms of fluid overload.

To treat fluid overload, patients are typically treated with a diuretic drug which induces and/or increases urine production. Producing and excreting urine reduces the amount of fluid and sodium in the body and thus may be used to treat a fluid overload condition. Diuretics can be given orally as a pill or as an IV (intravenous) injection. IV diuretics are typically used when oral diuretics are no longer effective or able to be absorbed. Where “diuretics” are mentioned, authors primarily refer to IV diuretics. Popular loop diuretics are diuretics that act at the ascending limb of the loop of Henle in the kidney. Examples of loop diuretics include: Bumetanide (Bumex®), Ethacrynic acid (Edecrin®), Furosemide (Lasix®), Torsemide (Demadex®).

The short-term effects of diuretics on urine production are not adequately predictable to administer high doses at early stages of treatment. For example, one patient may produce much less urine than expected for a given does of diuretic, while another patient administered the same does may produce excessive amounts of urine. This raises concerns of hypotension (low blood pressure) and vital organ damage in the patient. As a result, it is difficult to predict which patients will respond to a certain dose of a diuretic by excreting none or too small amounts of urine, and which patients will respond by excreting excessive amounts of urine.

The potential for substantially different responses and treatment outcomes in response to the same dosage of diuretics creates uncertainties for physicians such that safe and correct diuretic dosing for an individual patient requires monitoring the patient’s clinical signs and symptoms over a period of time. Because of these uncertainties, physicians may initially prescribe a conservative (low) diuretic dosage and wait a few hours before considering whether to increase the dosage. The conservative low dose approach starts with a low diuretic dose, and slowly and incrementally increases the dosage until the patient’s urine output reaches a threshold level, e.g., rate. Slowly increasing the diuretic dosage avoids causing an excessive urine output that can lead to hypovolemia and other undesirable medical conditions.

The current standard practice for treating fluid overload in ADHF and CHF uses a conservative low-dose approach that can prolong the treatment time to relieve a fluid overload condition in a patient. Generally, a physician increases a diuretic dosage at six to twelve hours intervals. These long intervals are often required to allow the patient to react to a new dosage level of a diuretic and produce urine at a rate induced by the new level of a diuretic. At the end of each interval, the physician determines if the diuretic dosage should be changed, such as increased, to cause the patient to produce a desired level of urine. Because these intervals are typically several hours in length, it may take six hours, twelve hours, a day or more to determine a safe, efficacious dosage level of a diuretic. For example, in patients who have not taken prior loop diuretic therapy, an initial IV furosemide dose of 20 to 40 mg is reasonable. Max diuretic dose recommended by regulatory guidelines is 40 to 80 mg of furosemide equivalent IV bolus. Subsequently, the dose can be titrated up according to the urine output to a maximum intravenous dose of 80 to 100 mg of furosemide. In the patients that developed some resistance to diuretics, doses need to be higher.

One aspect of this conservative approach for reducing fluid overload is that the patient’s symptoms associated with fluid overload may be prolonged while the physician determines and administers a safe and effective diuretic dosage to achieve a desired urine output rate. One drawback of this delay is that the clinical state underlying the fluid overload condition may worsen due to the prolonged fluid overload condition. For example, delays of many hours or days can occur before urine output reaches the desired levels to cause significant fluid loss and relieve the patient’s fluid overload condition. Another drawback is that the patient is hospitalized for several days (e.g., 4-5 days), which is expensive. Additionally, even after receiving a conventional treatment for reducing fluid overload about 23% of the patients are readmitted for fluid overload within 30 days. As a result, there is a long-felt need to reduce the time needed to cause a patient to increase urine output using a diuretic and more quickly cause the patient to output sufficient urine to reduce a fluid overloaded condition.

Another concern with using diuretics to treat fluid overload conditions results when the urine flow of a patient reaches high flow rates. Although high urine flow rates are beneficial in quickly reducing a fluid overload condition, high urine flow rates risk excessively reducing the volume of blood in the vasculature, as well as increased excretion of electrolytes. Rapid removal of electrolytes may lead to electrolyte imbalance (e.g. loss of potassium), which can further deteriorate a patient’s clinical condition. These risks and side effects of IV diuretics, which are often referred to as hypovolemia and hypokalemia, are known unnecessary risks and an unmet clinical need still is present during this necessary and commonly used therapy.

Excessive urine flow, such as in excess of 2.5 liters per day, may lead to hypovolemia, hypokalemia and other undesirable medical conditions. The risks of excessive urine flow caused by conventional fluid overload treatments, such as by using diuretics, are traditionally mitigated by limiting the rates at which urine flow is induced. Limiting the urine flow rates tends to increase the period needed to reduce a fluid overload condition in a patient.

To avoid these drawbacks, the approved dosages for certain diuretics have been limited, at least in part, to avoid or reduce the risks of hypovolemia, hypokalemia and other such undesirable medical conditions associated with intravascular blood volume becoming too low. For example, in a patient previously unexposed to loop diuretics (diuretic naïve) the furosemide diuretic is recommended to be administered intravenously (IV) at an initial dose of 20 milligrams per hour (mg/hr), and may be increased only every 6 to 12 hours. In heart failure patients that routinely take oral diuretics initial doses and stepwise dose increases need to be adjusted by a significant amount and this further complicates the titration of therapy.

In conventional approaches, the dosage level is not to be increased once a certain urine output level is reached. Other commonly prescribed diuretics, such as loop diuretics, such as bumetanide and torsemide; thiazide diuretics, such as hydrochlorothiazide and metolazone; potassium sparing diuretics, such as spironolactone; and carbonic anhydrase inhibitors, such as acetazolamide, are believed to also have regulated dosage limits to prevent excessive urine flow rates and other possible side effects of these drugs.

SUMMARY

A primary purpose of hospital admissions in heart failure patients is to remove extra fluid. However, for more than half of the heart failure patients during a hospital admission in the United States, the total fluid loss is less than five pounds (2.3 kilograms), which generally does not achieve effective relief from a fluid overload condition. Accordingly, there remains a need to improve upon conventional fluid management technologies, and achieve greater net fluid losses from patients in a shorter timeframe.

Embodiments of the present technology address the need for improved advances in patient fluid management, e.g., by creating an at least partially automated system that enables safe administration of diuretics, increased diuretic efficiency, and at least moderates diuretic resistance, while conserving valuable hospital resources and patient comfort. As described herein, clinical tests of embodiments of the present technology have caused rapid decongestion, removed excess fluid, increased sodium excretion, and reduced weight, each with improved effectiveness and/or speed. For example, whereas conventional systems and methods for treating fluid overload required hospitalization exceeding multiple days (e.g., 4-5 days), embodiments of the present technology are able to diagnose and/or relieve fluid overload conditions within 1-2 days.

The present technology relates to methods, devices, systems, and algorithms to reduce fluid levels in a fluid overloaded patient, such as one suffering from ADHF, CHF or other conditions that result in fluid overload. In some embodiments, an exemplary method includes a diuretic treatment regimen having multiple phases, including a Phase I, II, and III. Phase I can include determining an appropriate diuretic dosage that is specific to the patient, which may be done in iterations. For example, in some embodiments during a first iteration of Phase I, an initial diuretic dose, possibly automatically, is delivered to the patient. The dose is increased during Phase I, such as incrementally in steps, progressively increasing steps and/or exponentially. For example, the dose may be increased in a stepwise manner every two to three minutes. The dose can be increased until the patient reaches a desired urine output level or rate and/or until an upper threshold is reached. The first diuretic dosage provided to the patient is at the start of treatment and subsequent dosages can be in response to urine output falling below a threshold and/or outside a threshold range. The threshold may define a maximum (e.g., total) amount of the diuretic given to the patient, a maximum rate at which the diuretic is given to the patient, or a maximum period for Phase I, such as one hour.

Phase II is optional and can allow the patient to respond to the diuretic dose given during Phase I. After the urine output reaches a desired level during Phase I, Phase II can include delivering the diuretic to the patient at a constant maintenance dosage level for an extended period (e.g., at least one hour, at least two hours, four hours, 8 hours, 12 hours, 24 hours, or 36 hours). The maintenance dosage level is calculated based on the diuretic dosage in Phase I which resulted in urine output exceeding the desired output level.

Phase III is optional and can run concurrently with Phase II. During Phase III, diuretic continues to be administered and net fluid levels in a patient (e.g., a patient who has responded to Phase I and is producing above a threshold level of urine) can be rapidly reduced by infusing a hydration fluid or solution (e.g., saline) into the patient. During Phase III, the hydration fluid infused into the patient can be (i) automatically adjusted to match urine output during relatively low urine rates, (ii) automatically adjusted to reduce the hydration fluid to less than urine output (e.g., at least 10%, 20%, 30%, 40%, or 50% of urine output) during a range of higher urine rates, and/or (iii) automatically adjusted to maintain a substantially constant hydration fluid rate (e.g., within 10% to 20% of a maximum hydration fluid rate), while the urine output exceeds an upper urine threshold. During Phase III, the maintenance dosage of the diuretic may be adjusted, e.g., by restarting Phase I and initiating a re-ramp of the diuretic (e.g., in an exponential manner). Phase I can be restarted either by resuming where Phase I was last stopped or by repeating Phase I from its initial starting point.

Simultaneous with the diuretic regimen described above, the amount or rate of hydration solution given to the patient may be related to the amount or rate of urine output. For example, the amount or rate of the hydration solution delivered to the patient may be less than the amount or rate of urine output at higher levels of urine output. The rate of hydration infusion may be adjusted to match the rate of urine output for a particular period of time (e.g., the first hour of therapy) and/or a threshold volume amount (e.g., until at least 250 milliliters (ml) of urine has been produced). The rate of hydration solution infusion may remain at a constant rate while the urine rate exceeds a threshold high urine rate.

The maintenance diuretic dosage for Phases II and III may be calculated based on a percentage, such as in a range of 100% to 10% percent (e.g., 20%, 30%, 40%, 50%, 60%, 70%, 80%, 90%, etc.), of a maximum dose of the diuretic given during Phase I. The percentage reduction of the maximum continuous maintenance dose may be a ratio of the diuretic dosage (amount or rate) reached during Phase I that resulted in the urine output exceeding the desired output level and the maximum diuretic amount or rate of the upper threshold in Phase I.

If the upper threshold (e.g., the total amount of diuretic delivered to the patient) is reached in Phase I before urine output reaches the desired output, the patient may be diagnosed as diuretic resistant, and a different diuretic or a different treatment may be given to the patient. Such treatments can include ultrafiltration and/or use of an artificial pump (e.g., a venous pump) to enable the kidneys to produce more urine. If the urine output falls below a lower urine threshold for a certain period in Phase III, the regimen may repeat Phase I to induce greater urine output and identify a more effective diuretic dose level (e.g., a higher diuretic dosage).

Phase I may be restarted if the urine output (e.g., rate or amount) falls below a urine output threshold during Phase I, II or III. When Phase I is resumed from where it last stopped, it can be restarted at the rate of diuretic dosage which was given at the end of the prior iteration of Phase I. At the end of each iteration of Phase I, the maintenance diuretic dosage may be calculated based on the total amount of diuretic given during all of the iterations of Phase I.

Phases I and III may be applied as independent treatments. For example, an operator (e.g., a physician, health care specialist, nurse, etc.) may determine an initial diuretic dosage in a conventional manner and thereafter treat a patient using the Phase III portion of the regime. Similarly, an operator may use the Phase I portion of the regime to quickly determine an effective diuretic dosage to achieve a desired urine output rate and thereafter choose not to adjust the maintenance dosage of the diuretic or not to infuse the hydration fluid into the patient or select a different relationship between the diuretic dosage, urine output and hydration fluid solution infusion than is proposed in Phase III. Further, since Phase II is optional, Phase III may start immediately after Phase I.

The present technology may include a method to treat patients suffering fluid overload and can comprise: administrating a diuretic, such as automatically, to the patient to increase urine output of the patient; determining urine output by the patient during the administration of the diuretic; infusing a hydration fluid into the patient; and automatically adjusting a rate of the hydration fluid infused into the patient to achieve a desired net fluid loss in the patient. In some embodiments, the method may include automatic adjustment of the rate of the hydration fluid based on a difference between the urine output and the desired net fluid loss. The automatic adjustment of the rate of the hydration fluid may be calculated based on a current rate increase of the urine output, such that the rate increase of the hydration fluid is reduced in response to the urine output exceeding a first threshold output, such as a current rate of urine output. Additionally or alternatively, the automatic adjustment of the rate of the hydration fluid may include increasing the rate of the hydration fluid to a rate within 10% of a current rate of urine output, until the current rate of urine output reaches a first threshold output. The first threshold output may be a urine output rate in a range of 200 ml/hr to 240 ml/hr or an equivalent volume of urine output. The rate of the hydration fluid infusion may be limited to a maximum limit for the hydration fluid while a current urine output rate is above a second threshold is above 500 ml/hr, above 700 ml/hr, or above 1020 ml/hr.

In some embodiments, the method may include limiting a rate of the hydration fluid infusion to a maximum limit for the hydration fluid; maintaining the rate of the hydration fluid infusion at the maximum limit while the urine output exceeds a maximum threshold urine output rate; ending the treatment when the net fluid loss reaches a desired amount for the net fluid loss; automatically adjusting the diuretic administered to the patient based on the urine output; increasing a rate of the diuretic being administered until the urine output reaches a desired minimum urine value, wherein the minimum urine value is a minimum urine output rate; and/or automatically adjusting the diuretic by increasing the diuretic level at intervals of five minutes or less, e.g. two to three minutes, until the urine output reaches the desired minimum urine value. In some embodiments, each increase in the diuretic level, e.g., during a diuretic dosage determining phase or ramp, may be a greater increase than the immediately prior increase.

In some embodiments, the method may include determining a reduced diuretic dosage rate in response to the urine output reaching the desired minimum urine volume or rate. The reduced diuretic dosage rate is below the diuretic dosage rate when the urine output reached the desired minimum urine value or rate. The diuretic may be administered at the reduced rate for a period of at least one hour such as periods of two, three or four hours. This reduced diuretic administration rate may involve reducing the diuretic infusion rate to a very low rate until the measured urine rate drops below a desired threshold or a period, such as one hour, elapses. The diuretic administration rate may then be calculated based on the time required for the urine rate to drop to the desired threshold, or reduced by a predetermined percentage (such as 25%) if the urine output remains above the threshold when the period of very low infusion completes.

In some embodiments, a method of treatment or an automated regimen for managing or optimizing net fluid volume removal and/or enhancing quality of urine removed includes an initial personalized diuretic dosage determining phase followed by a fluid reduction phase. During the process of determining the diuretic dosage determining phase, the patient's urine response to an administered diuretic at increasing levels is assessed within a predetermined period of time to establish a diuretic dosage to be used in the following phase and/or to assess if the patient is diuretic resistant. During the fluid reduction phase, the diuretic is infused at the established diuretic dosage while replacing a portion of the urine production with hydration fluid, e.g., to maintain intravascular volume and/or turn off salt and water retaining mechanisms to optimize net volume removal. Throughout the fluid therapy, urine output is continuously monitored. The diuretic dosage may be adjusted based on the urine output rate. For example, very low urine output (e.g., less than 25 ml/hr averaged over the previous 15 minutes) may indicate equipment malfunction or improper set up and an alert may be given to the user. As another example, low urine output (e.g., low urine output may be defined as less than 325 ml/hr averaged over the previous 3 hours, or be defined by an integral debt function where the debt is more than 150 ml over the previous 3 hours) may indicate that a greater diuretic dosage may be allowed and a diuretic dosage may be reestablished. For example, the user may select to reenter the diuretic dosage determining phase or manually increase the dosage. As another example, high urine output (e.g., more than 625 ml/hr averaged over the previous 3 hours) may indicate too much diuretic is being infused and the infused diuretic may be reduced for a period of time (e.g., reduced to 0 to 0.4 ml/hr for 50 minutes or until the urine output has dropped below 525 ml/hr) and a new diuretic dosage may be established. For example, the new dosage may be a fraction of the previous dosage based on how quickly the urine output decreased during said period of time or be established by reentering the dosage determining phase. Furthermore, hydration fluid may be infused throughout the fluid reduction phase based on urine output.

The present technology may be embodied as a fluid management system comprising: a hydration fluid pump configured to pump a hydration fluid into a patient; a diuretic pump configured to pump a diuretic into the patient; a measurement device configured to measure urine output of the patient; a computer executing an algorithm configured to: determine an amount or rate of urine output of the patient; automatically inject a diuretic to the patient by controlling the diuretic pump to deliver the diuretic at a dosage rate determined by the algorithm; automatically infuse a hydration fluid into the patient by controlling the hydration fluid pump; and automatically adjust the rate or the amount of the hydration fluid infused into the patient to achieve a desired level or rate of net fluid loss in the patient or net sodium loss.

The algorithm may be configured to determine the automatic adjustment of the rate of the hydration fluid based on a difference between the urine output and the desired net fluid change; limit a rate of the hydration fluid infusion to a maximum limit for the hydration fluid; maintain the rate of the hydration fluid infusion at the maximum limit while the urine output exceeds a maximum threshold urine output rate, and/or stop the administration of the diuretic when the net fluid loss reaches a desired amount for the net fluid loss. Additionally or alternatively, the computer algorithm may be configured to automatically adjust the diuretic administered to the patient based on the urine output. The automatic adjustment of the diuretic may include increasing a rate of the diuretic being administered until the urine output reaches a desired minimum urine value, such as a minimum urine output rate. The adjustment of the diuretic may include automatically increasing the diuretic level at intervals of five minutes or less until the urine output reaches the desired minimum urine value, wherein at least one of the increases in the diuretic level is a greater increase than the immediately prior increase. Each of the increases in the diuretic level is greater than the increase of the immediately prior increase. The automatic adjustment of the diuretic may include: calculating a reduced rate for diuretic administration in response to the urine output reaching the desired minimum urine value or rate, wherein the reduced rate is below and based on a value of the diuretic administered when the urine output reached the desired minimum urine value or rate, and administering the diuretic at the reduced rate for a period of at least one hour.

BRIEF DESCRIPTION OF THE DRAWINGS

Features, aspects, and advantages of the presently disclosed technology may be better understood with regard to the following drawings.

Figure 1:
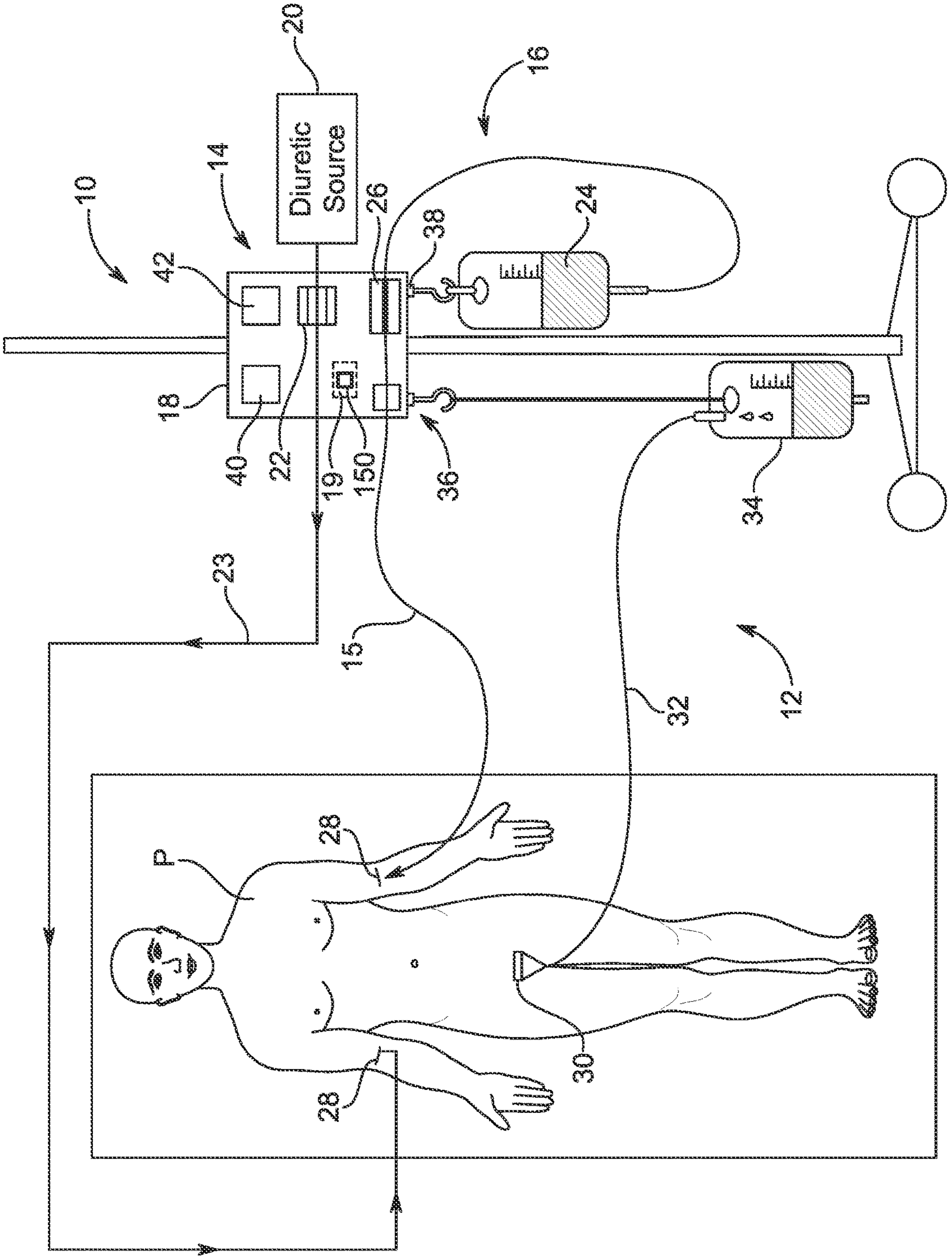
FIG. 1 is a schematic view of a patient hydration system configured to monitor urine output and control the injection of a fluid into a patient, in accordance with embodiments of the present technology.

A person skilled in the relevant art will understand that the features shown in the drawings are for purposes of illustrations, and variations, including different and/or additional features and arrangements thereof, are possible.

DETAILED DESCRIPTION

I. Overview of Devices, Systems and Associated Methods for Managing Fluid Levels Disclosed herein are devices, systems, and associated methods related to managing fluid levels of a patient. Relative to current fluid management systems, embodiments of the present technology can improve efficacy, safety and quality of fluid management treatment, improve resource management in a hospital, quickly assess if a patient is diuretic resistant, and/or increase diuretic efficiency. Diuretic efficiency can be defined as the amount of urine and/or excreted sodium obtained over a given time per milligram of diuretic infused intravenously. One expected result of the present technology is that diuretic efficiency can be increased by intravenous infusion of hydration fluid that contains sodium and/or chloride. This is counterintuitive since a goal of fluid therapy is net removal of salt (e.g., sodium and chloride) and fluid. As described herein, embodiments of the present technology can increase net removal of fluid and sodium while both the hydration rate and the urine excretion or output rate are also increased, and, in some embodiments, with the urine excretion rate being increased more than the hydration infusion rate. Increasing diuretic efficiency, which embodiments of the present technology do, as opposed to increasing diuretic dose, is a clinically relevant and beneficial therapy, as it allows for the treatment of fluid overload conditions in a more efficient manner (e.g., shorter timeframe, higher net fluid loss, and/or higher net sodium loss). Additionally, embodiments of the present technology are configured to increase diuretic efficiency while preventing hypotension, e.g., by automatically maintaining net fluid loss above a set fluid loss limit (e.g., at least 50 ml/hour, 100 ml/hour, 150 ml/hour, or 200 ml/hour). As explained elsewhere herein, net fluid loss can be controlled by adjusting the diuretic dosage rate, and/or adjusting the hydration infusion rate relative to the urine output rate, or more specifically, based on whether the urine output rate is above or below a number of different thresholds.

FIG. 1 shows a patient fluid management system 10 that includes a urine collection and monitoring system 12 ("urine system 12") and an automated diuretic infusion system 14 ("diuretic system 14"). In some embodiments, the fluid management system 10 can further include an automated hydration fluid infusion system 16 ("hydration system 16"). The urine system 12, diuretic system 14, and hydration system 16 can be connected to a patient P by tubing lines (e.g., intravenous (IV) lines) 15, 23 for the respective diuretic and hydration systems 14, 16, and a catheter line 32 (e.g., a Foley catheter, Texan Condom catheter, Pure Wick catheter, etc.) for the urine system 12. The fluid management system 10 can include a console 18 housing one or more pumps or electric motor actuators 22, 26, a computer (e.g., a controller or microprocessor(s)) 19, and a user input device 40 (e.g., a key pad) and output device 42 (e.g., a display) in communication with the urine system 12, diuretic system 14, and/or hydration system 16. The controller includes electronic programmable memory and receives input from various sensors (e.g. a urine monitor, a hydration monitor, weight scales, flowmeters, optical sensors, fluid level meters, ultrasound fluid meters, feedback sensors of pump speeds or actuator movements, pressure sensors, blood pressure sensors, air detectors, etc.), and/or a user interface. The controller is configured to automatically control actuators to infuse the hydration fluid and the diuretic, e.g., to promote safe and effective diuresis of the patient.

The diuretic system 14 includes or is in fluid communication with a source of a diuretic 20. The diuretic 20 can include Bumetanide (Bumex®), Ethacrynic acid (Edecrin®), Furosemide (Lasix®), Torsemide (Demadex®), and/or other diuretics known in the art, each of which may be part of a fluid solution (e.g., a mixture of saline and a diuretic or other agent). The diuretic 20 can be infused into the patient using a separate IV tube inserted into a suitable peripheral vein of the patient or added to the hydration fluid prior to the infusion.

In some embodiments, the diuretic 20 may be contained in a syringe barrel (not shown) or other container (e.g., bag), and injected intravenously through an IV needle. The diuretic system 14 may include multiple syringes or containers of the diuretic 20 that are each available for use, such that if a first syringe or container is spent, supply of the diuretic 20 can continue (e.g., without substantial interruption) via a second (or third) syringe or container. As an example, the diuretic system 14 can be designed such that two independent syringe pumps are available for use, each fluidly coupled to its own syringe filled with diuretic 20. It is noted that such syringes may only be filled by pharmacists or other health care professionals, and thus may not be readily replaced (e.g., in less than a few hours). When the diuretic system 14 detects that the first syringe is empty, diuretic supply can begin (e.g., automatically or manually begin) to dispense diuretic 20 from the second syringe. In some embodiments, this may entail stopping a first syringe pump fluidly coupled to the now spent first syringe, and starting a second syringe pump fluidly coupled to the second syringe. Additionally or alternatively, if only a single pump is utilized, switching between the first syringe and second syringe may involve manipulating one or more valves such that the pump is supplied from the second syringe. Upon manually or automatically switching to the second syringe, an alert to the operator can then be made to let the operator know that the first syringe must be replaced with a new full syringe.

Additionally or alternatively, the diuretic system 14 can predict when the diuretic 20 is nearly empty (e.g., will be empty in an hour), alert the user, and/or automatically switch to the second syringe or ask the user to confirm switching manually to the second syringe. In some embodiments, manually switching may be required for regulatory concerns, e.g., to ensure the diuretic system 14 does not automatically infuse a large volume of diuretic 20 without user confirmation. Additionally or alternately, the system can be designed with only one syringe pump, and the system can alert the operator in advance of the first syringe being empty, and the operation can momentarily halt the syringe pump so that the first nearly empty syringe can be removed and replaced with a second full syringe, and the pump restarted to continue dispensing of diuretic.

By having a second (or third, fourth, etc.) syringe, or more generally a backup supply, administering the diuretic 20 can proceed without interruption throughout a fluid therapy session. As described elsewhere herein, the lack of interruption can help ensure that the fluid therapy, described with reference to embodiments of the present disclosure, is most effective and inhibits or prevents unnecessary delays. More specifically, interruption in therapy, even if for short periods, can cause urine output rate to drop and/or require a diuretic ramp (as explained elsewhere herein) to be reimplemented. Embodiments of the present technology that utilize a backup supply of the diuretic 20, as well as other redundancy measures explained herein (e.g., with respect to the hydration fluid source, urine collection, etc.) can thus avoid such interruption and enable more effective therapy.

The pump 22 can be a peristaltic pump, a syringe pump, a metering pump or another device suitable for controllable injection of IV medication. In such embodiments including a syringe pump, the pump 22 can include a mechanical injector operably coupled to the computer 19, such that the computer 19 causes movement of the injector to transfer the diuretic 20 from the source to the patient. An actuator can be a mechanical actuator under an electric motor control by a rotary motor or a linear motor or a series of electrically actuated solenoids configured to propel liquid through an IV delivery tubing toward the patient. The pump 22 or actuator delivers the diuretic 20 at a controlled continuous rate and/or in controlled boluses delivered at regular intervals through the IV line 23 and into the patient. The pump 22 or actuator is controlled by the computer 19, which may have executable instructions or a software algorithm incorporated in the console. The computer 19 or associated algorithm is configured to determine a pumping rate of the diuretic 20 and/or associated solution to achieve a desired dosage for the diuretic 20. The computer 19 controls the pump 22 or actuator to deliver dosage amounts of the diuretic 20 based on a treatment regimen prescribed, e.g., by an operator and managed by the computer 19. The control logic of the computer 19 can be a software or a firmware embedded therein to control the infusion of diuretic based on the program time profile, user input and/or input from various sensors.

The diuretic system 14 can include a reusable motor, actuator and control electronics, as well as one or more reusable or disposable parts connectable to the motor, actuator and electronics. The reusable or disposable parts can include a medical agent (e.g., a medicament or diuretic) container or reservoir (e.g., a plastic syringe, plastic bag, etc.), IV tubing set and needle. In some embodiments, the reusable and disposable parts described herein are attached with attachment schemes that are comparatively simple to engage and disengage, for example, in a single-step procedure (e.g., snap connections).

In some embodiments, the diuretic system 14 can include one or more syringe pumps. Each of the syringe pumps can be designed to allow attachment of needles, tubing, and other attachments to the syringe pump, and can include a plunger mounted to a shaft that pushes a liquid out of a reservoir. The reservoir may be a tube-shaped structure having a port at one end such that the plunger can push (i.e., discharge) the liquid out of the syringe pump. Syringe pumps can be coupled to an actuator that mechanically drives the plunger to control the delivery of liquid to the patient. The linear actuator may comprise, for example, a nut for rotating a lead screw to drive a plunger through the medical agent reservoir. A syringe pump can be equipped with a plunger position sensor, air bubble detector and other embedded electronics needed to provide feedback signals to the controller. In some embodiments, the syringe pump for administering an agent to a patient comprises a housing, a lead screw, and a sliding block assembly. The sliding block assembly can comprise a threaded portion capable of engaging and disengaging from the lead screw, and a latching mechanism for quick engaging and disengaging of the syringe thus enabling quick change of an empty syringe for a full one. In some embodiments, a syringe pump for administering diuretic to a patient comprises a housing. Within the housing may be a motor, a gearbox operatively connected to the motor, a means for sensing rotation of said motor (e.g., a tachometer or an optical encoder), a controller (e.g., a microcontroller) acting to control operation of said motor and monitor the quantity of diuretic delivered to the patient, and a pump assembly. In some cases, the plunger includes a fluid-contacting surface made from an elastic material such as silicone rubber or urethane. In some cases, the reusable part forms a void space for receiving the lead screw when the lead screw is retracted from the reservoir.

In some embodiments, a combination of two or more medical agents may be needed for optimal and/or effective diuresis of the patient. For this purpose, in some embodiments, the disposable part can further include a second reservoir for containing additional fluid agent, a second plunger for driving additional fluid agent out of the second reservoir, a second lead screw attached to the second plunger, and a second nut operable to displace the second lead screw, such that when the reusable part and the disposable part are attached, the second nut is coupled with the drive component. In some embodiments, the step of controlling the device such that the fluid agent is delivered includes simultaneously driving both of the first and second plungers (e.g., at the same rate or at different rates). In other instances, the step of controlling the device such that the fluid agent is delivered includes independently driving the first and second plungers (e.g., sequentially and/or intermittently).

In some embodiments, the pump may be a syringe pump or peristaltic pump. Although design of these two types of pumps is mechanically deferent, both can be considered computer-controlled, electrically actuated mechanical devices for precise and controlled propulsion of liquid (i.e., solution containing diuretic of choice or a combination of diuretics, electrolytes and other active and passive ingredients) to inject the liquid solution into the patient's bloodstream through a suitable vein.

In embodiments including a peristaltic pump, a liquid solution containing a diuretic may be supplied in the disposable container, which can be a plastic bag with attachments to plastic tubing, and the reusable part can be a peristaltic pump capable of engaging the plastic tubing and propelling fluid from the bag into the patient under precise control from the electronic controller. In such embodiments, the reusable component may incorporate an electric motor activated actuator that can be a roller pump with compression rollers cyclically engaging the tubing or a liner peristaltic pump sequentially engaging, compressing and releasing the tubing, thus propelling the bolus of fluid forward towards the patient.

As shown in FIG. 1, the diuretic 20 may be stored in a container (e.g., bag). The container may include a solution (e.g., saline) with a certain concentration of a diuretic. The concentration of the diuretic can be input into the computer 19, such as via the user input device 40, which may include a scanner to read bar codes on such containers and thereby indicate the type of diuretic and concentration. Alternatively, a coupling between the container and the console 18 may be configured such that the coupling only receives a certain container that is known by the computer 19 to store a known diuretic at a certain concentration.

In some embodiments, The hydration system 16 includes or is connectable to a fluid source 24, such as a saline bag containing a saline solution (which may or may not be the same saline solution previously described that is mixed with the diuretic), a hydration fluid infusion pump 26 (e.g., a peristaltic pump) optionally mounted to the console 18 that may accept an IV line 15. The IV line 15 is coupled or connectable to the fluid source 24 and an intravenous (I.V.) needle 28 for insertion into a vein of the patient. The amount or rate of hydration fluid(s) flowing from the source 24 into the patient may be measured by a flow, volumetric, or other sensor downstream of the pump 26, or by the pumping rate or number of rotations of the infusion pump 26. The amount or rate can be an input, e.g., into the algorithm or computer 19. As explained elsewhere herein, the pumping rate of the hydration fluid may be regulated by the computer 19 or associated algorithm and based, at least in part, on the urine output and an electronically stored relationship between urine output and infusion of the hydration fluid. The computer 19 may monitor the amount of or change in hydration fluid in the source 24, e.g., with input from a weight scale 38 weighing the source 24. The amount of hydration fluid or rate of change of hydration fluid can also be measured by other means, such as a fluid level monitor, float sensors, optical sensors, drip counters, flow measurement sensors, or the like.

In some embodiments, the hydration system 16 can include multiple (e.g., redundant) fluid sources 24, e.g., to ensure supply of the hydration fluid can continue without interruption for the entirety of a therapy session. As an example of such embodiments, when the system or computer 19 detects that the first source container is empty or near empty (e.g., through measuring container weight, a reduction in flow rate, etc.), flow can be stopped from the first source and started from the second source. For example, supply may be switched from the first source to the second source by closing a first valve (e.g., a pinch valve applied to the exterior of the fluid supply tubing), and opening a second valve allowing flow from the second container. An alert to the operator may then be made to let the operator know that the first source container must be replaced with a new full container. Additionally or alternatively, the hydration system 16 can predict when the fluid source is nearly empty (e.g., will be empty in 15 minutes), alert the user, and/or automatically switch to the second fluid source. In some embodiments, manually switching may be required for regulatory concerns, e.g., to ensure the hydration system 14 does not automatically infuse hydration fluid without user confirmation. By having a second (or third, fourth, etc.) supply of hydration fluid, or more generally a backup supply, infusing the hydration fluid can proceed without interruption throughout a fluid therapy session. As described elsewhere herein, the lack of interruption can help ensure that the fluid therapy is most effective, e.g., by relieving a fluid overload condition as fast and as safe as possible. Stated differently, interruption in fluid therapy, even if for short periods, can cause urine output rate to drop and/or require a diuretic ramp (as explained elsewhere herein) to be reimplemented. Embodiments of the present technology that utilize a backup supply of the diuretic 20, as well as other redundancy measures explained herein (e.g., with respect to the diuretic, urine collection, etc.) can avoid such interruption and thus enable more effective therapy.

The urine system 12 includes or is connectable to a disposable catheter 30 (e.g., a Foley catheter) for placement in the bladder of patient, and disposable tubing 32 that connects the catheter 30 to a urine collection device (e.g., a disposable bag) 34. The amount of urine collected in the bag 34 can be monitored by a weight scale 36 or other urine flow measurement device which communicates with the computer 19. For example, the amount or rate of urine flow can be determined via a urine measurement device, fluid level monitor, float sensors, optical sensors, drip counters, flow measurement sensors, or the like. The amount or rate of urine collected can be monitored in real time by the computer 19 or calculated. Similarly, the amount of fluid or diuretic 20 may be measured for example by a weight scale 38 and monitored by the computer 19. Alternatively, the weight scales 36, 38 may be a single weight scale which measures the combined change in urine output and fluid input by and to the patient. The combined change in urine output and fluid input indicates the net fluid change by the patient.

In some embodiments, the urine system 12 can include multiple (e.g., redundant) independent urine collection devices 34, e.g., to ensure fluid therapy does not need to be stopped or interrupted due to a full urine collection device. As an example of such embodiments, when the system or computer 19 detects that a first urine collection device is full (e.g., by sensing the weight of the collection device, by calculating the total collected volume with a flow sensor, etc.), urine flow from the patient can be redirected to the second collection device. An alert to the operator can then be made to instruct the operator to empty the first urine collection device and indicate its replacement in the system. In some embodiments, the urine drain tubing leading from the patient may be connected (e.g., through a "Y" fitting) to two flexible tubing lines each leading to one of the available urine collection devices. Flow to each collection device may be controlled with pinch valves that compress the tubing from the outside, thereby allowing flow through the tubing to be stopped when the pinch valve is released. If the first pinch valve is opened and the second one is closed, urine flow will be directed to the first collection device and not the second collection device. When the first collection device is detected by the computer 19 to be full, the first pinch valve can close and the second pinch valve can open, thus switching urine flow to the second collection device and allowing the first collection to be taken offline and removed.

In some embodiments, the fluid management system 10 corresponds or is similar to the Reprieve Cardiovascular™ system, developed and clinically tested by Reprieve Cardiovascular, Inc. of Milford, Massachusetts.

The computer 19 may include a processor(s) and tangible, non-transient memory configured to store program instructions, settings for the patient fluid management system 10 and data collected or calculated by the computer 19. The data may include historical data for the patient, e.g., diuretic doses delivered to the patient, urine output volume or rate, amount of hydration fluid infused into the patient, the weight or change in weight of the patient at various times during the infusion of the diuretic, indicators of the patients renal function (e.g., estimated glomerular Filtration Rate (eGFR)), and/or the time(s) during which the patient was treated with the patient fluid management system 10.

As previously described, the console 18 and/or the computer 19 may have a user input device 40, such as a key pad, and a user output device 42, such as a computer display. A user may interface with the computer 19 through the input device 40, which may be used to input certain parameters of the treatment sessions, such as a desired fluid balance level, desired urine output level, the planned duration of the input balance level or urine output level, the diuretic type, and minimum and maximum dosages of the diuretic. Other inputs may be regarding the patient (e.g., sex, weight, "dry" weight, age, target fluid removal volume, renal function, etc.). The inputs may be used by the computer 19 to lookup from tables or other data stored in the computer 19 certain parameters such as maximum diuretic dosage, maximum continuous diuretic dosage, and minimum desired urine rate. The computer 19 may display recommended levels of initial and maximum diuretic levels for the operator to select and program into the computer settings. Another input may be the amount of fluids during the treatment session received by the patient through means other than the diuretic 20, such as fluid ingested or other medical agents injected. For example, the input device 44 may be configured to receive inputs indicating the amount of diuretic injected into the patient such as from the pump 22 for the diuretic or from the source 20 of the diuretic.

Figure 2A:
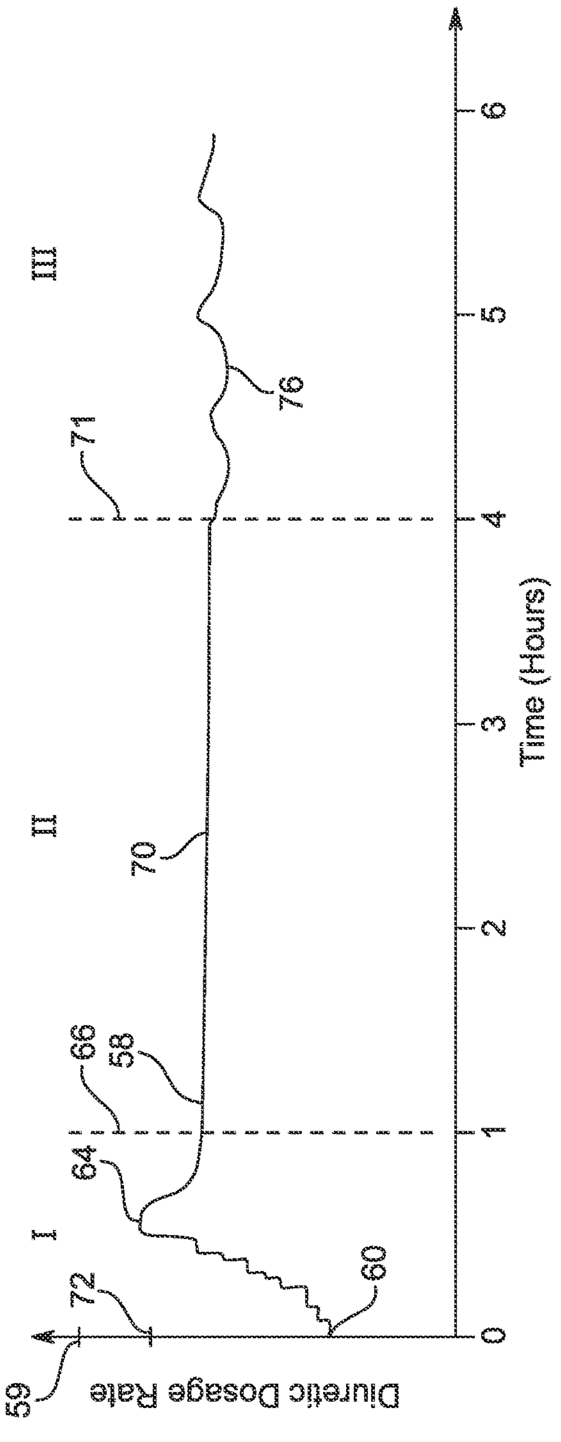
FIG. 2A is a graphical representation showing a timeline of diuretic dosage dispensed by a fluid management system during a treatment regimen, in accordance with embodiments of the present technology.
Figure 2B:
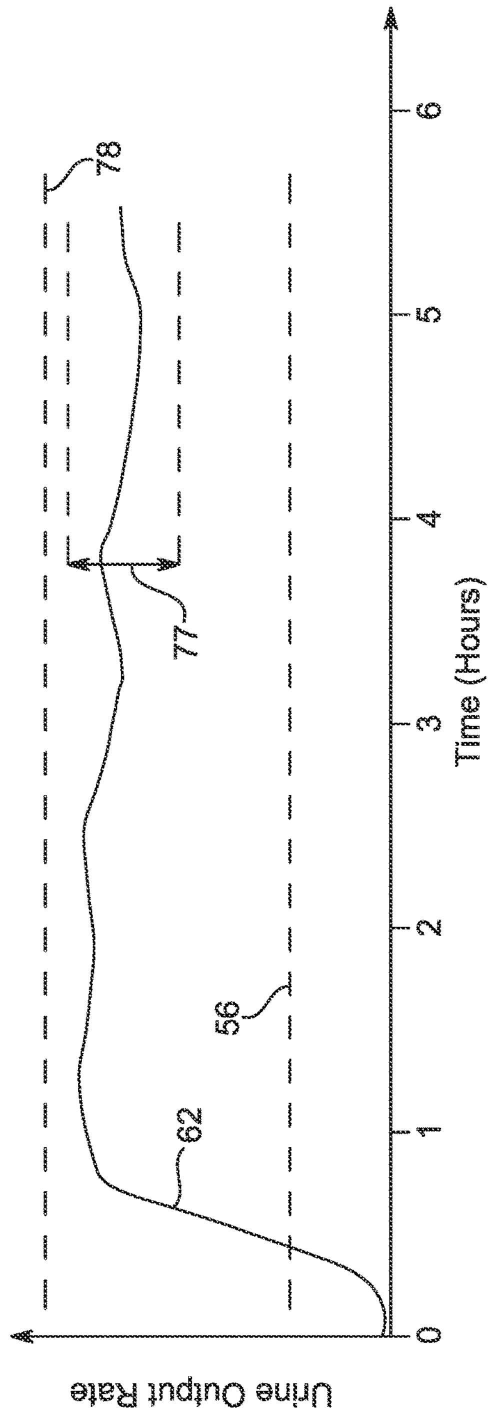
FIG. 2B is a graphical representation showing a timeline of urine flow rate achieved by the diuretic dispensed by the fluid management system during the treatment regimen of FIG. 2A.

FIGS. 2A and 2B are graphical representations of an exemplary treatment method, with FIG. 2A illustrating a diuretic dosage rate 58 (e.g., mass of the diuretic per hour) dispensed over a period of time and FIG. 2B illustrating a corresponding urine output rate 62 (e.g., volume or urine per hour). In accordance with embodiments of the present technology, the treatment method shown and described with reference to FIGS. 2A and 2B can enable a patient to reach and maintain a desired urine output rate within a predetermined period of time. Referring to both FIGS. 2A and 2B together, the diuretic dosage 58 and urine flow rate 62 are shown on the graphical representation for a time period of approximately six hours, which includes an initial period referred to as Phase I or a "diuretic dosage determining phase", a subsequent period referred to as Phase II or a "continuous diuretic dosage phase", and a final period referred to as Phase III. As shown in FIG. 2A, Phase I is approximately one hour, Phase II is approximately three hours, and Phase III is approximately two hours. In other embodiments, these times can vary and be more or less than the time durations shown in FIG. 2A. For example, Phase III can include a majority of a therapy sessions and thus may be 1-36 hours.

In Phase I, an effective and safe diuretic dosage rate and/or dose is determined, e.g., in as short a time as possible, to cause the patient to produce urine at or above a threshold level 56. In order to quickly increase urine output rate 62, e.g., in less than 30 minutes, 60 minutes, 90 minutes, or 120 minutes, the diuretic dosage rate 58 can be intentionally significantly higher than the dosage rate to be later applied to maintain urine output at or above the threshold urine rate or another urine rate level. That is, the maximum diuretic dosage rate 58 administered in Phase I may be intentionally higher (e.g., 100% higher, 200% higher, 300% higher, 400% higher, 500% higher, 600% higher, or within a range of 100-600% higher) than the expected diuretic dosage rate 58 needed to produce the urine output rate 62 above the threshold level 56 (as shown in Phase II).

During Phase I, the diuretic dosage rate 58 can be set to an initial dosage 60 that may be prescribed by the operator who inputs the dosage via the user input device 42 of a console (e.g., the console 18; FIG. 1). The initial dosage rate 60 is a non-zero value and can be at least 50 mg/hr, 75 mg/hr, 100 mg/hr, 125 mg/hr, 150 mg/hr or within a range of 50-150 mg/hr (or any value therebetween). In some embodiments, the initial dosage rate 60 may be determined by the system and be set as a default initial dosage rate or be based on other input data specific to the patient (e.g., the patient's weight, excess fluid weight, or other parameter). The operator may also input other parameters of the treatment regimen, such as a maximum allowable diuretic dosage (maximum total amount of diuretic and/or maximum diuretic dosage rate) 59, minimum 56 and/or maximum 78 desired urine outputs (total amount of urine output and/or urine output rate), and/or periods for Phases I, II and III. The initial dosage 60 of the diuretic may be selected as being conservative and lower than needed to cause the patient to produce urine. For some patients, the initial dosage rate may be sufficient to promote a urine output rate above the threshold 56.

A computer or controller (e.g., the computer 19; FIG. 1) monitors and may track urine output rate 62. Monitoring of urine output rate may start before or when the initial low dosage rate 60 of the diuretic is given to the patient. The urine output rate may be monitored or calculated in real-time or at regular intervals, such as every 30 seconds, minute or multiple minutes. In some embodiments, the initial urine output is expected to be below the minimum desired urine output rate 56. If the initial urine output rate is above the minimum desired urine output rate 56, the operator may consider increasing the minimum desired urine output rate or altering the amount and/or rate of diuretic to be administered. In some embodiments, the computer automatically increases the dosage rate of the diuretic during Phase I until the urine output rate is at or above the desired minimum urine rate 56. The diuretic dosage rate may be automatically increased by the computer by adjusting operation of a diuretic pump (e.g., the diuretic pump 22; FIG. 1). The computer may be programmed to exponentially increase the dosage rate, increase the dosage rate at a linear rate, or determine dosage rate increases based on another algorithm for increasing the dosage rate executed by the computer. The computer, or algorithm utilized by the computer, may limit the diuretic dosage rate to be no greater than a maximum diuretic dosage rate 59 entered by the operator or stored in the computer. In some embodiments, the diuretic dosage rate is increased in steps from the initial dosage rate 60 to a peak diuretic dosage rate 64 of Phase I, such that each step increases (e.g., doubles) the amount of increase made in the prior step, e.g., by at least 50% or 100% (or a value therebetween). In such embodiments, the rate of increase of the dosage rate (i.e., the slope of the diuretic dosage) may continually increase with each step until the maximum dosage 64 is reached. The end 66 of Phase I may be a preset time period, be determined based on when the peak diuretic dosage rate 64 is reached, or be a certain period (e.g., at least 2 minutes, 5 minutes, 10 minutes or within a range of 2-10 minutes) after the peak diuretic dosage rate 64 is reached.

The diuretic dosage rate 58 can be increased continuously, or in increments after a set period of time (e.g., every 2 minutes, 3 minutes, 4 minutes, or 5 minutes) during Phase I, wherein each increase in the dosage is a greater than the prior increase. In some embodiments, the increase is exponential and/or may result in a doubling of the diuretic dosage rate every 15 minutes. The algorithm may be derived by fitting series of step increases to an exponential curve defined by f(x)=a*b*x, wherein f(x) is an exponential function, a is a constant, b is a positive real number, and x is an exponent. The values for a, b and x may be determined by experimentation and/or a physician, and may be specifically tailored for each patient. The values for a, b and x may be set in the algorithm stored in the computer. Additionally or alternatively, such values may be based on patient specific inputs (e.g., the patient's weight, excess fluid weight, home dose of oral diuretic, or other parameter).

As the diuretic dosage rate 58 is increased during Phase I, the computer monitors the urine output rate 62. The computer can automatically increase the diuretic dosage rate 58 according to the algorithm for diuretic dosage rate increases executed by the computer. The increases in diuretic dosage rate can continue until the urine output rate 62 reaches or exceeds the desired minimum urine rate 56. When the computer determines that urine output rate 62 reaches the desired minimum urine output rate 56, the diuretic dosage rate 58 is not further increased and thus corresponds to the peak diuretic dosage rate 64. In some embodiments, the computer may be programmed to prevent the diuretic dosage rate 58 to exceed the maximum diuretic dosage rate 59 regardless of whether the urine output reaches the desired minimum urine output rate 56.

In some patients, the urine output rate 62 can significantly exceed the desired minimum urine rate due to the rapidly increasing and possibly relatively large diuretic dosage rate 64. As discussed elsewhere herein, patients with high urine output rates may require simultaneous infusion of hydration fluid and optionally down titration of diuretic dosage if the urine output rate is too high, both of which may be controlled by the computer algorithm.

Phase I may also end if a specified time period 66 for the phase expires before urine output rate reaches the desired minimum urine rate. The period 66 may be determined based on the maximum diuretic dosage rate 59, such as no more than 5, 10, 15, or 30 minutes (or another value therebetween) after the maximum diuretic dosage rate 59 is reached. Phase I may be an hour, in a range of 45-90 minutes or 30-120 minutes. If the Phase I period expires, the computer may generate an alert (e.g., from the user output device 42; FIG. 1) to indicate that (i) Phase I expired due to time and not upon reaching a maximum diuretic dosage rate 59, which may indicate a lower than desired urine rate, (ii) the patient is diuretic resistant, (iii) a different diuretic may be given to the patient and Phase I restarted, and/or (iv) an alternative fluid reduction treatment should be given to the patient, such as ultrafiltration or venous pumping. Relative to current methods of administering a diuretic to produce urine output, embodiments of the present technology can cause the urine output rate to increase at a faster pace and thereby enable rapid decongestion, rapid symptom relief (E.g., dyspnea) increased fluid removal, increased sodium excretion, and/or weight reduction in a shorter time period. As previously described, conventional technologies often take conservative approaches and increase the diuretic dosage rates slowly so as to maintain more control over urine output. However, doing so can cause delays of hours or days, which thereby further exacerbate the underlying fluid overload condition. Unlike these conventional technologies, the relatively fast pace of embodiments of the present technology can be beneficial to patients suffering from fluid overload or pulmonary edema in a shorter time frame, as the rapid increase in diuretic dosage rate and thus urine production can decrease the volume of fluid in the patient's extravascular space and pull fluid back into the intravascular space within just a few hours. Moreover, as explained in detail elsewhere herein, in some embodiments, the rapid diuretic ramp can be paired with a corresponding infusion of hydration fluids to optimize net fluid loss while also maintaining a sufficient amount of intravascular volume to maintain proper kidney function.

With continued reference to FIGS. 2A and 2B, the regimen or method can automatically transition to Phase II after the peak diuretic dosage rate 64 is reached or the Phase I period 66 expires. Phase II may extend until the end of the fluid therapy and can be configured to maintain the diuretic dosage rate 58 at a constant rate or dosage level for an extended period of time 71, such as at least two hours, three hours, four hours, eight hours, 12 hours, 24 hours, 36 hours, or other set period. In some embodiments, Phase II is intended to allow the patient's body to adjust to the diuretic dosage rate 58, and generate for the entire Phase II period a urine output rate that is (i) at or greater than the desired minimum urine output rate 56 and/or (ii) maintained within a particular range.

During Phase II, the diuretic dosage rate 58 may be set at a continuous dosage level (e.g., a maintenance dosage rate) 70, which may remain constant during all or most of Phase II. The maintenance dosage rate 70 may be the same as the peak dosage rate 64 reached during Phase I or a certain proportion of the peak dosage rate 64, such as 90%, 80%, 70%, 60%, 50%, 40%, 30%, 20%, 10%, or in a range of 90% to 10% of the peak dosage rate 64. In some embodiments, the diuretic maintenance dosage 70 is set based on a diuretic dosage level 72, which corresponds to a dosage rate required in Phase I to reach the desired minimum urine rate 56, or a total amount of diuretic required during Phase I. For example, in some embodiments, the diuretic maintenance dosage rate 70 has a value that is a percentage (e.g., 15%, 20%, 30%, 40%, 50%, or within a range of 15-50%) of a value of the total or cumulative dose (e.g., in terms of mass or volume) delivered in Phase I. For example, if the total dose of diuretic delivered in Phase I is 100 mg, then the diuretic maintenance dosage rate 70 may be 20 mg/hr. Additionally or alternatively, in embodiments wherein Phase II begins due to time expiration of Phase I, the diuretic maintenance dosage rate 70 can limited to a maximum rate (e.g., no more than 40 mg/hr, 35 mg/hr, 30 mg/hr). The maintenance dosage rate 70 given in Phase II may be selected by the operator and input into the computer. In some embodiments, the maximum diuretic maintenance dosage rate 72 may be stored in the computer such as in a table.

The regimen or method can automatically transition to Phase III at the end of Phase II. Phase III can continue until the treatment regimen is completed, which may occur when the net fluid removed from the patient reaches a certain volume or weight (e.g., determined automatically or by the operator), or at the expiration of a certain period of time (e.g., one, two or three days). Net fluid removal refers to a difference between the amount of fluids excreted by the patient (which may correspond to urine output) and the amount of fluid intake by the patient.

During Phase III, the computer may adjust the diuretic dosage rate 76 to, for example, (i) maintain the urine output rate 62 within a desired range 77, (ii) adjust the diuretic dosage rate 76 to maintain the urine output rate 62 above a desired minimum output rate 56, and/or (iii) keep the urine output rate 62 below a maximum urine output rate 78. The desired range 77 may be automatically calculated based on the average urine output rate during Phase II, such as a range of 80% to 120% of the average urine output rate during Phase II. The desired range 77 may be a range centered on 525 ml/hr, e.g., with the lower end of the range at 475 ml/hr and the high end at 575 ml/hr. Alternatively, the desired range or desired minimum and maximum urine output rates may be parameters input by the operator into the computer or may be stored in the computer. The diuretic dosage rate for Phase III may also be the kept at the same dosage rate as the continuous dosage rate 70 for Phase II, such that Phases II and III operate in similar manners. Further, if the urine output level 62 falls below a desired minimum urine output level (which may or may not be the same level as in Phase I), the computer may automatically restart Phase I or issue an alert or report from the computer suggesting that Phase I be restarted, e.g., in order to determine a more optimal diuretic maintenance dosage rate. For example, if the urine rate falls below 325 ml/hr for a period of three hours, the computer may restart Phase I. Similarly, if the urine output rate repeatedly cycles between below 325 ml/hr and above 325 ml/hr such that the net fluid reduction is effectively too low, the computer may restart Phase I. To determine if the net fluid reduction is too low, the software may calculate a "debt" value, defined as the area below 325 ml/hr and above the current urine output rate over a given period of time, such as 3 hours. For instance, if the urine output rate was 300 ml/hr for an hour, the "debt" would be 25 ml (325 minus 300). If the "debt" exceeds a set value over a set amount of time, for instance 150 ml of debt over 3 hours, the computer may automatically restart Phase I or issue an alert or report from the user output device 42 suggesting that Phase I be restarted.

During Phase III, the computer may automatically reduce the dosage of the diuretic, such as a 20%, 35%, 55%, 75% or more, of the current dosage rate, if the urine output rate exceeds a high threshold level. If, after a certain period, such as one hour, the urine output rate remains too high after the diuretic dosage rate is reduced, e.g., remains above the threshold level, the computer may automatically stop or down-titrate infusion of the diuretic for a certain period. For example, if the urine output rate exceeds 625 ml/hr for an hour, the computer may automatically stop infusion of the diuretic or reduce the diuretic dosage rate to the minimum dosage rate for a predefined period (e.g., 50 minutes to an hour). If the urine output rate drops below a set threshold in response to the reduction in diuretic dosage rate, the computer may resume continuous diuretic infusion at a percentage of the previous continuous dosage rate. The reduction may be based on the duration of stopped diuretic dosage rate that had elapsed when the urine output rate dropped below the threshold level. If the predefined period elapses and the urine output rate remains above the threshold level, then the continuous dosage rate may be resumed at a rate reduced by a predefined amount, such as a 25 percent reduction from the continuous dosage rate prior to the stopping of the injection.

In addition to controlling the diuretic dosage rate, the computer may execute a program for controlling infusion of the hydration fluid from the hydration fluid source 24 into the patient. The computer may control the infusion of the hydration fluid by controlling the infusion pump (e.g., the infusion pump 26; FIG. 1) based on an algorithm to achieve a desired net fluid reduction in the patient.

Figure 3:
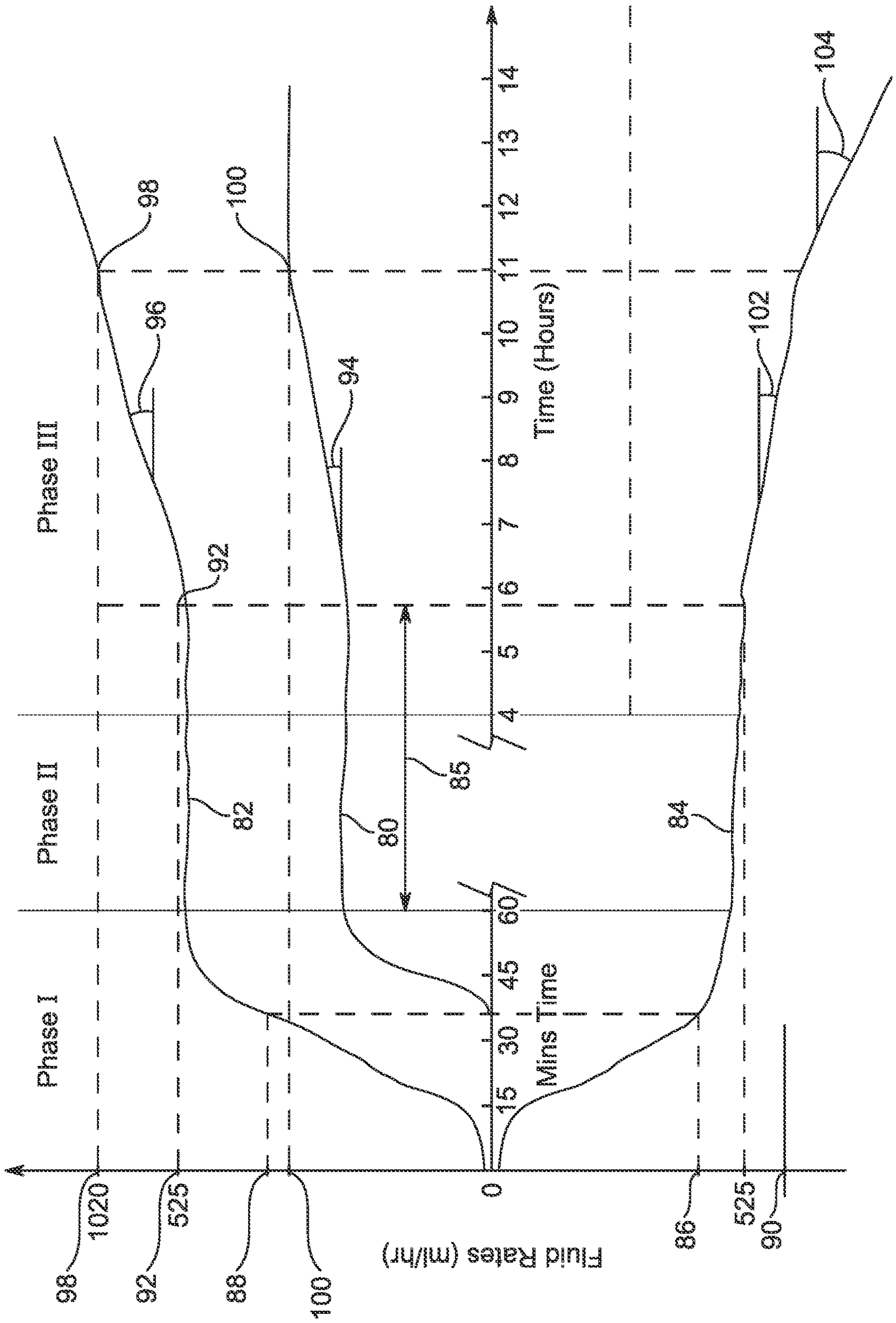
FIG. 3 is a graphical representation showing a relationship between urine output, hydration fluid infusion, and net fluid loss, in accordance with embodiments of the present technology.

FIG. 3 is a graphical representation showing a relationship between urine output, hydration fluid infusion, and net fluid loss, in accordance with embodiments of the present technology. Stated differently, FIG. 3 illustrates an exemplary representation for how embodiments of the present technology automatically control the hydration fluid infusion rate 80 based on the urine output rate 82 to achieve a net fluid change rate 84 in a patient. The control of the hydration fluid infusion rate 80 can be performed simultaneously to the control of diuretic dosage during Phases I, II and/or III.

The urine output rate 82 is expected to initially increase during Phase I and thereby result in an increase in the net fluid reduction rate. In some embodiments, the hydration fluid infusion rate 80 can match the urine output rate 82 until a predetermined volume (e.g., at least 150 ml, 200 ml, 250 ml, 300 ml, 400 ml, 500 ml, or within a range of 150-500 ml) of urine has been measured, or a particular period of time (e.g., at least 60 minutes) has elapsed. In some embodiments, the net fluid reduction rate 84 may substantially equal the urine output rate 82 until hydration fluid is infused into the patient. The computer may determine that hydration fluid is to be added if and when the net fluid reduction rate 84 falls below a threshold minimum value 86 or the urine output rate 82 exceeds a threshold urine output rate 88. These threshold values may be input by the physician into the user input device 40 or stored (e.g., as defaults) in the computer. These threshold values need not occur simultaneously as shown in FIG. 3, but are related and thus are likely to happen at approximately the same time. Alternatively, the computer may cause hydration fluid to be infused at near the same time that the diuretic begins to be infused, including when Phase I or a diuretic dosage determining phase is implemented (e.g., reimplemented). Once one or both of the threshold values 86, 88 are reached, the computer may automatically initiate the infusion of hydration fluid 80 by actuating an infusion pump (e.g., the hydration infusion pump 26; FIG. 1) to pump hydration fluid from a fluid source (e.g., the fluid source 24; FIG. 1) into the patient. The rate of hydration fluid 80 infusion may be calculated or determined by the computer based on, for example, a difference between the current urine output rate and a desired net fluid balance rate 90. For example, if the desired net fluid reduction rate is 200 (ml/hr) and the urine output rate is 400 ml/hr, then the computer may automatically control the infusion of the hydration fluid at a rate of 200 ml/hr.

The computer may adjust the infusion rate 80 of the hydration fluid to maintain a desired net fluid reduction rate 84, such a net fluid balance rate 84 that is constant, between a particular range, or below (i.e., more negative than) a threshold. During an initial phase or period 85, the hydration fluid may be infused for an hour or until a predetermined amount (e.g., at least 500 ml) of hydration fluid is infused, whichever event occurs first. During the initial phase 85, the computer may match the rate of increase in urine output 82 with the rate of increase in the hydration fluid infusion 80. Increasing the hydration fluid at the same rate of increase of urine output infuses into the vascular system a substantial amount of hydration fluid. Hydration fluid includes a relatively high concentration of sodium and/or chloride as compared to the typical respective sodium and chloride concentration in urine, and thus infusing hydration fluid into the vascular system increases the sodium and/or chloride level in the blood, even as the patient is excreting urine. Similarly, the hydration fluid may add potassium to the blood at rates greater than the discharge of potassium from urine. In doing so, the initial period 85 allows the sodium, chloride, and/or potassium levels in the blood to be artificially increased which provides a safeguard against sodium, chloride, and/or potassium depletion in the patient if the blood volume drops to relatively low levels during the treatment.

After the initial phase 85, the computer may increase the hydration fluid rate 80 at a rate 94 less than the current rate increase 96 of urine output rate 82 (e.g., a proportion of the current rate increase 96 of about 10%, 20%, 30%, 40%, 50%, 60%, 70%, 80%, 90%, 95%, or within a range of 10%-95%). Alternatively, the computer may reduce the rate of increase 94 for the hydration fluid in response to the urine output rate 82 exceeding a first threshold value 92 (e.g., 400 ml/hr, 420 ml/hr, 440 ml/hr, or within a range of 400-440 ml/hr), above which hydration fluid rate 80 is not further increased. If and while the urine output rate 82 exceeds a first threshold 92, the computer may reduce further the rate of increase 94 in the hydration fluid 80 to significantly less than the current rate of increase 96 of the urine output 82. For example, while the urine output rate 82 is above the first threshold 92, a further rate of increase 96 in the urine output rate 82 will be matched by a further rate of increase 94 in the hydration fluid infusion rate 80, which is increased at only one-half, or in a range of one quarter to three-fourths, the rate of increase 96 of the urine output rate 82. Simultaneously, the rate of decrease 102 of net fluid reduction 84 increases due to the greater rate of increase of urine output as compared to the lower rate of increase of hydration fluid. As described elsewhere herein, adjusting (e.g., increasing or decreasing) the hydration fluid rate (or rate of increase of the hydration fluid rate) less than that of the urine output rate can cause net fluid removal of salt within the patient, as well as net fluid loss.

If the urine output rate 82 continues to increase and exceeds a second threshold 98 (e.g., at least 500 ml/hr, 1020 ml/hr, or a range of 500-1020 ml/hr), the computer may automatically cease further increases in the hydration fluid rate 80. While the urine output rate 82 is above the second threshold 98, the computer may maintain the hydration fluid rate 80 at a constant rate 100 (e.g., 200 ml/hr) regardless of further increases in the urine output rate 82. Moreover, the increase in the net fluid reduction rate 84 has an advantage of reducing the period needed to reach a desired total net fluid reduction. The rate 104 of net fluid reduction increases due to the increase in the urine output rate 82 and the constant hydration fluid rate 80.

Setting the threshold 98 for a maximum urine output beyond which hydration fluid is not further increased is based, in part, on a desire to avoid excessive sodium levels in the patient. The sodium concentration in urine may change throughout the treatment as the physiological state of the patient changes but less than (e.g., approximately one-half) the sodium concentration of a saline solution that is expected to be used as the hydration fluid. At high infusion rates of the hydration fluid, the net sodium increase to the patient may become excessive over the course of an hour or more of treatment. To reduce the sodium added to the patient, an upper limit 100 is applied to the hydration fluid rate 80. This limit may be indirectly imposed by setting a threshold maximum urine output rate 98 beyond which the hydration fluid rate 80 is not increased as the urine rate increases beyond the threshold 98.

As mentioned above, the computer may automatically act to reduce high urine output rates, such as above thresholds 92 and/or 98, by reducing the diuretic dosage. The diuretic dosage rate may be increased to dosage levels previously considered inappropriate for fluid reduction treatments. Embodiments of the present technology can administered diuretic at these high levels due to (i) the automatic reduction in the diuretic dosage in response to the urine output rate 82 exceeding threshold levels 92, 98, and/or (ii) hydration fluid infusion directly into the vascular system of a patient. The infusion of the hydration fluid reduces the risk that the blood volume in the patient will become too low due to a high diuretic dosage. Thus, the diuretic dosage levels 64, 70, 76 described with reference to FIG. 2A may be substantially greater than maximum dosage levels conventionally viewed as appropriate and approved.

The computer may store certain limits on the treatment, such as a default fluid balance rate and a maximum net fluid loss. The default net fluid balance rate may be a negative 220 ml/hr or in a range of 150 ml/hr to 260 ml/hr. The maximum net fluid loss limit may be 5 liters (5,000 ml), at which point the computer issues a report or alarm, and may stop injecting the diuretic, at least temporarily. An operator may respond to the alarm by entering higher maximum net fluid loss limit, such as in increments of 1 liter. In response to the higher maximum net fluid loss limit, the computer may resume Phase III.

A clinical study utilizing embodiments of the present technology consistently reduced the fluid volume in patients faster than conventional standards of care. In previous studies of this patient population, only 47% of patients receiving standard of care achieve a goal of removing four to five liters of fluid volume and it typically takes five days of hospitalization to achieve. In comparison, embodiments of the present technology resulted in removing a net of four to five liters of fluid volume in 24 hours or less. The urine sodium data from this study confirms that embodiments of the present technology also remove significant amounts of salt via high-sodium urine from the patients in addition to net decrease in fluid volume. The urine of patients receiving the conventional standard of care remove substantially only hypotonic urine (e.g., 60-70 mmol sodium). The greater removal of salt achieved via embodiments of the present technology may result in less drive for the patient to reaccumulate fluid after discharge and result in a significant reduction in rehospitalization rates.

In addition to automating delivery of diuretic and hydration fluids based on urine output, embodiments of the present technology may optimize net fluid volume removal; reduce time needed to achieve desired net fluid removal by allowing physicians to use higher doses or dosage rates of diuretics earlier in treatment compared to the standard of care; avoid or reduce risk of adverse events such as over-diuresis, dehydration, or intravascular depletion; quickly assess if a patient is diuretic resistant; and provide a record of treatment data. Embodiments of the present technology aim to obtain an average net fluid removal rate (average rate of urine released minus average rate of hydration fluid introduced) of at least 225 ml/hr, which provides 3.4 liters per day of net fluid volume removal based on introducing 2 liters of fluid per day orally or through IV infusion. This rate of fluid removal while replacing sodium may allow a reduction in length of stay (LOS), as well as enable enhanced decongestion.

To achieve these objectives, embodiments of the present technology have a short diuretic dosage determining phase to determine an appropriate continuous diuretic infusion rate, which is then used in a fluid reduction phase during which urine output is continuously monitored and used to assess if the diuretic infusion rate continues to be suitable and to adjust the diuretic infusion rate accordingly. Concurrently, the algorithm controls infusion of hydration fluid to replace a portion of the sodium and fluid removed. The rate of infusion of hydration fluid is at least in part a function of the rate of urine output.

Figure 4A:
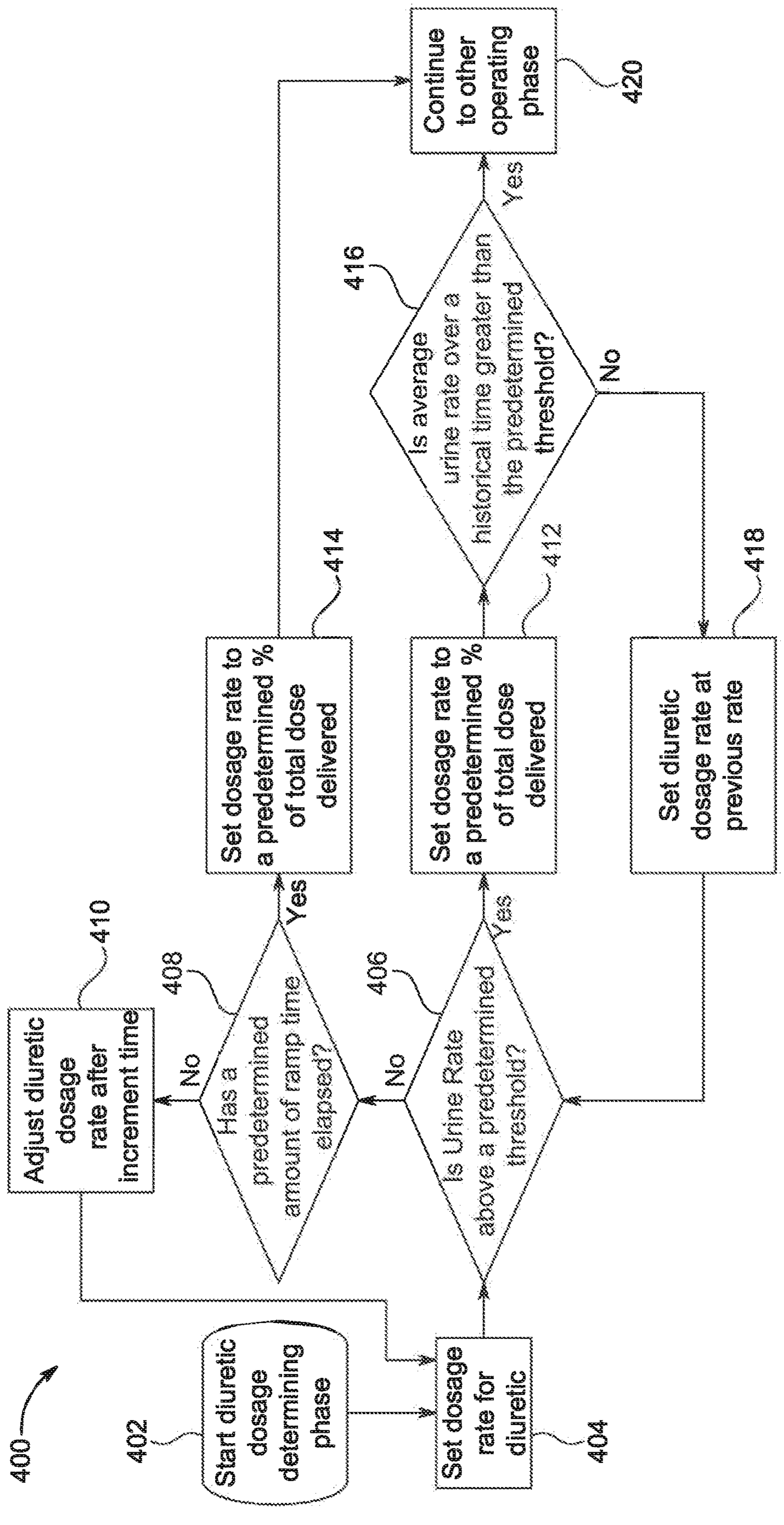
FIG. 4A is a flowchart for controlling diuretic dosage during a diuretic dosage determining phase, in accordance with embodiments of the present technology.

FIG. 4A shows a flowchart of a method 400 that controls a rate of infusion of diuretic during a diuretic dosage determining phase (process portion 402). The method 400 can be part of the algorithm described elsewhere herein. The diuretic dosage determining phase can correspond in whole or in part to the diuretic dosage determining phase described with reference to FIG. 2. The diuretic dosage determining phase can correspond to the beginning of fluid management therapy, or be triggered when one of more of a set of conditions is met (e.g., the urine output drops below a threshold). The start of the diuretic dosage determining phase may be triggered manually by a user, e.g., if the user thinks the diuretic dosage rate is too low or the urine output is too low and wants to reassess the diuretic dosage. In this regard, the underlying physiological state of the patient often changes over the course of fluid therapy of hospitalization, and therefore the diuretic dosage required to cause the patient to produce a desired urine output rate may need to be adjusted by repeating the diuretic dosage determining phase.

As shown in FIG. 4A, the diuretic dosage determining phase can begin by setting a diuretic dosage rate (process portion 404). The initial diuretic dosage rate can be set relatively low (e.g., no more than 60 mg/hr, 80 mg/hr, 100 mg/hr, 120 mg/hr, or within a range of 60-120 mg/hr), and/or be based on factors specific to the patient (e.g., sex, age, weight, historical treatment, etc.). Once a diuretic dosage rate is provided, the system (e.g., the fluid management system 10, the diuretic system 14, and/or any subsystems thereof; FIG. 1) can check whether the urine rate is above a predetermined threshold (process portion 406). The predetermined threshold can be 200 ml/hour, 300 ml/hour, 400 ml/hour, 450 ml/hour, 500 ml/hour, 525 ml/hour, 550 ml/hour, or within a range of 200-550 ml/hour. If the urine rate is not above the predetermined threshold, the system can check whether a predetermined amount of time (e.g., ramp time) has elapsed (process portion 408). The ramp time can be no more than 40 minutes, 50 minutes, 60 minutes, 70 minutes, or 80 minutes, or within a range of 40-80 minutes. If the ramp time has elapsed without the urine rate exceeding the predetermined threshold, the system may adjust the diuretic dosage rate on an iterative basis after an increment time (e.g., every 2 minutes, 3 minutes, 4 minutes, or other set interval). The adjusted diuretic dosage rate can be increased linearly or exponentially until either the urine output rate exceeds the predetermined threshold or the ramp time has elapsed. The diuretic dosage rate for a given minute t may calculated with the formula: A*(2^(t*B))+C, where A, B, and Care constant values. In some embodiments, an exponential increase may optimize speed of finding a suitable dosage rate safely, whereas a slower increase (e.g., a linear increase) can work to find the suitable dosage rate but may take longer. In some embodiments, each incremental step increase is greater than the immediately previous step, such that the diuretic dosage rate is doubled over a certain time period (e.g., every 5 minutes, 10 minutes, 15 minutes, 20 minutes, or within a range of 5-20 minutes). In doing so, the system enables the urine rate to increase in an efficient and rapid manner, thereby enabling excess fluid to be removed from the patient as soon as possible and/or identify whether the patient has a condition (e.g., is diuretic resistant) as soon as possible. In some embodiments, the diuretic may be limited to a maximum dose amount (e.g., 200 mg for furosemide) over the ramp time. In this regard, the system can be configured to only provide diuretic dosages that are within health care regulations and can be safely delivered.

If the urine rate, in response to the increased diuretic dosage, is above the predetermined threshold, then a value of the adjusted dosage rate (e.g., the initial rate for the subsequent continuous infusion phase) is set to a predetermined percentage (e.g., 10%, 15%, 20%, 25%, 30%, or within a range of 10-30%) of a value of the total dose delivered to the patient at that time (process portion 412). For example, if the total dose delivered is 100 mg, then the adjusted dosage rate may be 20 mg/hr if the predetermined percentage is 20%. Similarly, if the ramp time elapses before the urine rate exceeds the predetermined threshold, the value of the dosage rate can be set to the predetermined percentage of the value of the total dose delivered to the patient at that time (process portion 414). The percentage may be based on a pharmacokinetic characteristic of the particular diuretic being infused. For example, if the diuretic is furosemide, the fraction may be 20%, and if 50 mg of furosemide is infused in 60 minutes, then the calculated continuous diuretic dosage rate may be 10 mg/hr. This concept is described in additional detail with reference to FIG. 4B. Decreasing the diuretic dosage rate rapidly to a percentage of the total dose delivered, and/or less than the immediately previous dosage rate or average dosage rate over the previous 5-10 minutes, can enable the urine rate to decrease its rate of increase (e.g., to approach a slope of zero) but without actually decreasing the urine output itself. Additionally or alternatively, such a diuretic dosage decrease can enable the urine rate to be maintained at a predetermined rate and/or within a predetermined range.

Once the dosage rate is set, per process portion 412, the system may determine whether the average urine rate over a predetermined historical time (e.g., 5 minutes, 10 minutes, 15 minutes) is greater than the predetermined threshold (process portion 416). Process portion 416 can serve as an additional verification that the urine rate is high enough to proceed to other operating phases. For example, if the urine rate peaked over the predetermined threshold for a moment but was not consistently over the predetermined threshold, process portion 416 would provide an alarm and/or prevent the system from proceeding to a subsequent operating phase. If the average unit rate is over the predetermined threshold, the system can proceed to another operating phase, such as the continuous infusion phase (e.g., described with reference to FIG. 5). If the average urine rate is not greater than the predetermined threshold, the diuretic dosage rate may be set to the immediately previous rate (process portion 418) and then returned to process portion 406, e.g., to re-ramp the diuretic dosage rate to increase the urine rate.

The diuretic dosage determining phase enables the diuretic dosage rate to be ramped quickly and to a high dosage rate, relative to current systems and methods, thereby allowing a patient's urine rate to be rapidly increased to be above a minimum threshold. Unlike current systems and methods which do not quickly ramp the diuretic dosage, but rather slowly increase the diuretic dosage to err on the side of safety (e.g., to avoid over-diuresis), embodiments of the present technology can ramp the diuretic dosage rate in a relatively fast manner, because the risk of diuresis or related issues can be mitigated, e.g., by the ability of these same embodiments to automatically decrease the diuretic dosage rate once a certain urine output is reached and/or control hydration fluid infusion. In doing so, embodiments of the present technology can efficiently cause net fluid loss from the patient, while also setting a net fluid loss limit (e.g., 100 ml/hr) to ensure that a sufficient amount of intravascular volume is maintained by the patient. This inhibits the drop in cardiac output and renal perfusion that is often observed when urine output rates approach elevated levels for heart failure patients.

Figure 4B:
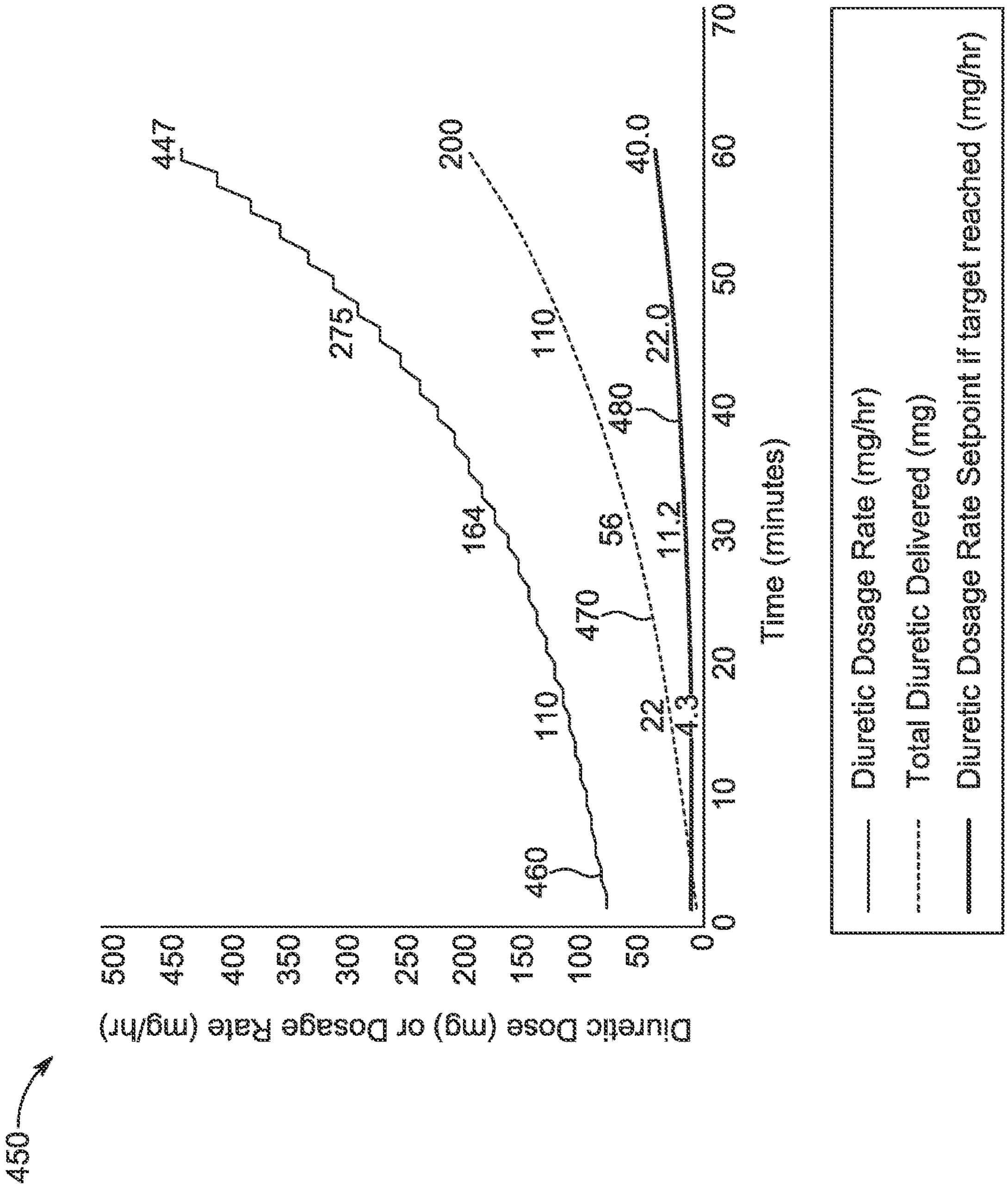
FIG. 4B is a graphical representation showing a relationship between diuretic dosage rate and total diuretic delivered, in accordance with embodiments of the present technology.

FIG. 4B is a graphical representation 450 showing a relationship between diuretic dosage rate 460 and total diuretic delivered 470, in accordance with embodiments of the present technology. The concepts shown and described in FIG. 4B can apply to other aspects of the present technology that relate to the diuretic dosage determining phase, diuretic ramp, and associated features. As shown in FIG. 4B, the diuretic dosage rate 460 can be ramped from an initial rate of about 75 mg/hr to a final rate of about 447 mg/hr within a time period of 60 minutes. As such, the diuretic dosage rate 460 can increase by about 500% over the time period. As also shown, the diuretic dosage rate 460 can effectively double within a time period of about 20 minutes.

The total diuretic delivered 470 (mg) corresponds to the cumulative amount of diuretic that has been delivered up to that point in time. As previously described (e.g., with reference to FIG. 4A), a value of the total diuretic delivered 470 can be used to determine the value or set point for the diuretic after the urine output rate of the patient reaches a predetermined threshold. For example, once the urine output rate reaches the predetermined threshold (e.g., 400 ml/hour, 450 ml/hour, 500 ml/hour, 525 ml/hour, 550 ml/hour, or within a range of 400-550 ml/hour), a value of the diuretic dosage rate may be set to be a percentage (e.g., 20%) of a value of the total diuretic delivered 470 up to that point in time. As shown in FIG. 4B, the diuretic dosage rate setpoint 480 corresponds to 20% of the value of the total diuretic delivered 470. It is noted that the values shown in FIG. 4B may be used for a furosemide diuretic. Use of other diuretics may require different dosage rates, but similar general principles as those described herein would apply.

II. Reramp or Rapid Increase of Diuretic Dosage Rate

Figure 5:
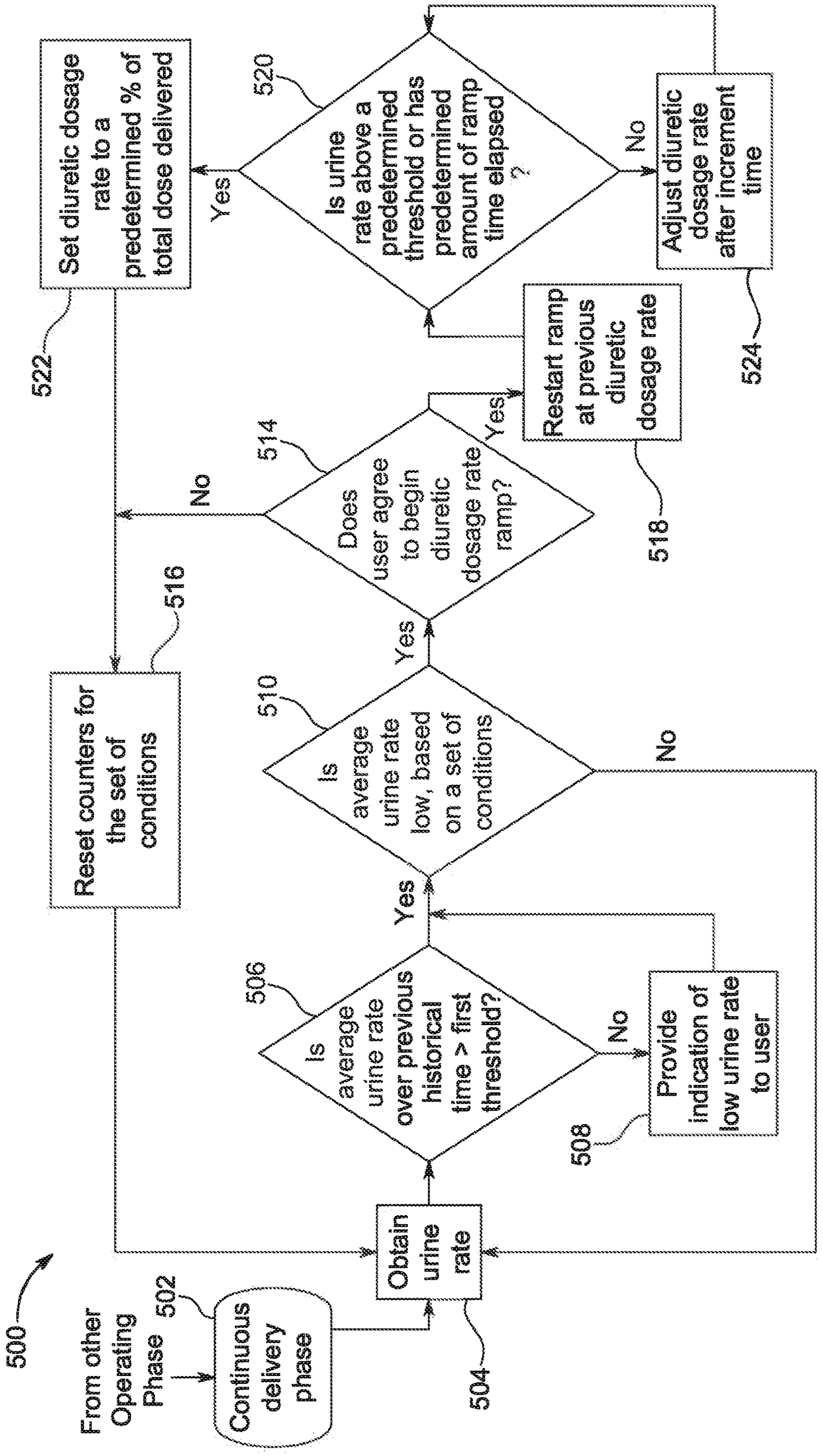
FIG. 5 is a flowchart of a continuous infusion or fluid reduction phase, in accordance with embodiments of the present technology.

FIG. 5 is a flowchart 500 of a continuous diuretic delivery phase or another phase (e.g., a fluid reduction phase), in accordance with embodiments of the present technology. As described elsewhere herein, the continuous delivery phase 502 can occur after the diuretic dosage determining phase, or more specifically after the urine output rate had previously been above a predetermined threshold. The continuous infusion phase may coincide with the fluid reduction phase, during which hydration fluid is infused at a rate less than the urine output rate to thereby cause net fluid loss. During the continuous delivery phase, the urine rate is checked and/or obtained (process portion 504) on a regular basis (e.g., every minute) to ensure the urine rate is at expected levels and responding to the diuretic dosage. As part of this check, the system can determine whether the average urine output over a previous historical time (e.g., the previous 10 minutes, 15 minutes, 20 minutes) is greater than a first threshold amount (e.g., 20 ml, 25 ml, 30 ml, 40 ml) (process portion 506). If the average urine output is not greater than the first threshold, an alert message may be given (e.g. displayed on the User Output Device 42; FIG. 1) to inform the user of very low urine rate and risk of blocked Foley catheter or other equipment malfunction (process portion 508). Subsequently, the average urine rate can be checked against a set of conditions to determine if urine rate is low (process portion 510) and/or if a ramp (e.g., a reramp) of the diuretic dosage is warranted. If any one of the set of conditions is met and thus urine output is determined to be low, the system may proceed to ramp or reramp the diuretic dosage to establish (e.g., by returning to the diuretic dosage determining phase), or reestablish the urine rate above a minimum threshold. If the urine rate is not low, the system may operate in a loop to continuously monitor urine rate.

The set of conditions can include determining whether (i) the average urine rate is below a predetermined threshold rate (e.g., 250 ml/hr, 300 ml/hr, 325 ml/hr, 350 ml/hr, 400 ml/hr, or within a range of 250-400 ml/hr) for a predetermined period of time (e.g., 2 hours, 2.5 hours, 3 hours, or within a range of 2-3 hours), or (ii) more than a predetermined amount (e.g., 100 ml, 125 ml, 150 ml, 175 ml, or within a range of 100-175 ml/hr) of debt has accumulated over the predetermined period of time. "Debt" can be defined as the area on a plot between the urine output rate and a set rate (e.g., 325 ml/hr), and essentially represents how much of and for how long the urine output rate has been below the set rate. The debt can accumulate unless an associated counter is reset. For example, if the patient released urine at a constant rate of 300 ml/hr over 3 hours the debt will be 75 ml for a set rate of 325 ml/hr. The lower the urine output rate the greater the debt. If the urine output rate rises above the set rate, debt is not accumulated, but is still considered until a certain amount of time (e.g., 3 hours) have passed since the debt was accumulated. Calculating debt in such a manner enables embodiments of the present technology to respond to a low urine output rate more quickly than if debt calculation was not utilized.

If any one of the set of conditions is met and thus the average urine rate is too low, the user may be asked to confirm that a reramp or diuretic dosage determining phase is to be implemented (process portion 514). Regulations may require that the user's confirmation be received prior to beginning the reramp. If the user does not agree to the reramp, the counters for the set of conditions may be reset. That is, the debt accumulated and the period of time used to calculate whether the urine rate is below the predetermined threshold can be reset to zero. If the user agrees to the reramp, the ramp can be started at the previous diuretic dosage rate (process portion 518), e.g., where the previous ramp finished. In such embodiments, the diuretic dosage rate begins at the final rate in the previous ramp and the total elapsed ramp time accumulates on the previous total elapsed ramp time. This concept is shown and described in additional detail with reference to FIG. 6. After starting the ramp, the system determines whether the urine rate is above a predetermined threshold (e.g., 400 ml/hour, 450 ml/hour, 500 ml/hour, 525 ml/hour, 550 ml/hour, or within a range of 400-550 ml/hour) or whether a predetermined amount of time (e.g., the ramp time) has elapsed (process portion 520). If not, the system may adjust the diuretic dosage rate after an increment time (process portion 524), as described elsewhere herein. If the urine rate is above the predetermined threshold, the diuretic dosage rate can be set to a predetermined percentage (e.g., 10%, 15%, 20%, 25%, 30%, or within a range of 10-30%) of the total dose delivered to the patient at that time (process portion 522). Subsequently, the counters for the set of conditions are reset (process portion 516), and the system may revert to process portion 504.

In some embodiments, the user may check over the equipment and decide to manually adjust the continuous diuretic dosage rate, or trigger reentry to the diuretic dosage determining phase. If reentry is manually triggered, the patient can receive up to 60 minutes of total elapsed ramp time, which may be the highest continuous dose allowed per the regulatory agencies. As such, if the total elapsed ramp time is more than 55 minutes, then there may be little benefit to reentering a ramp. In such embodiments, a 3-hour average urine output rate is reset and a urine debt is set to 0 and the algorithm returns to process portion 504. However, if the total elapsed ramp time is less than or equal to 55 minutes, the user may be asked to confirm a ramp restart (process portion 514).

Figure 6:
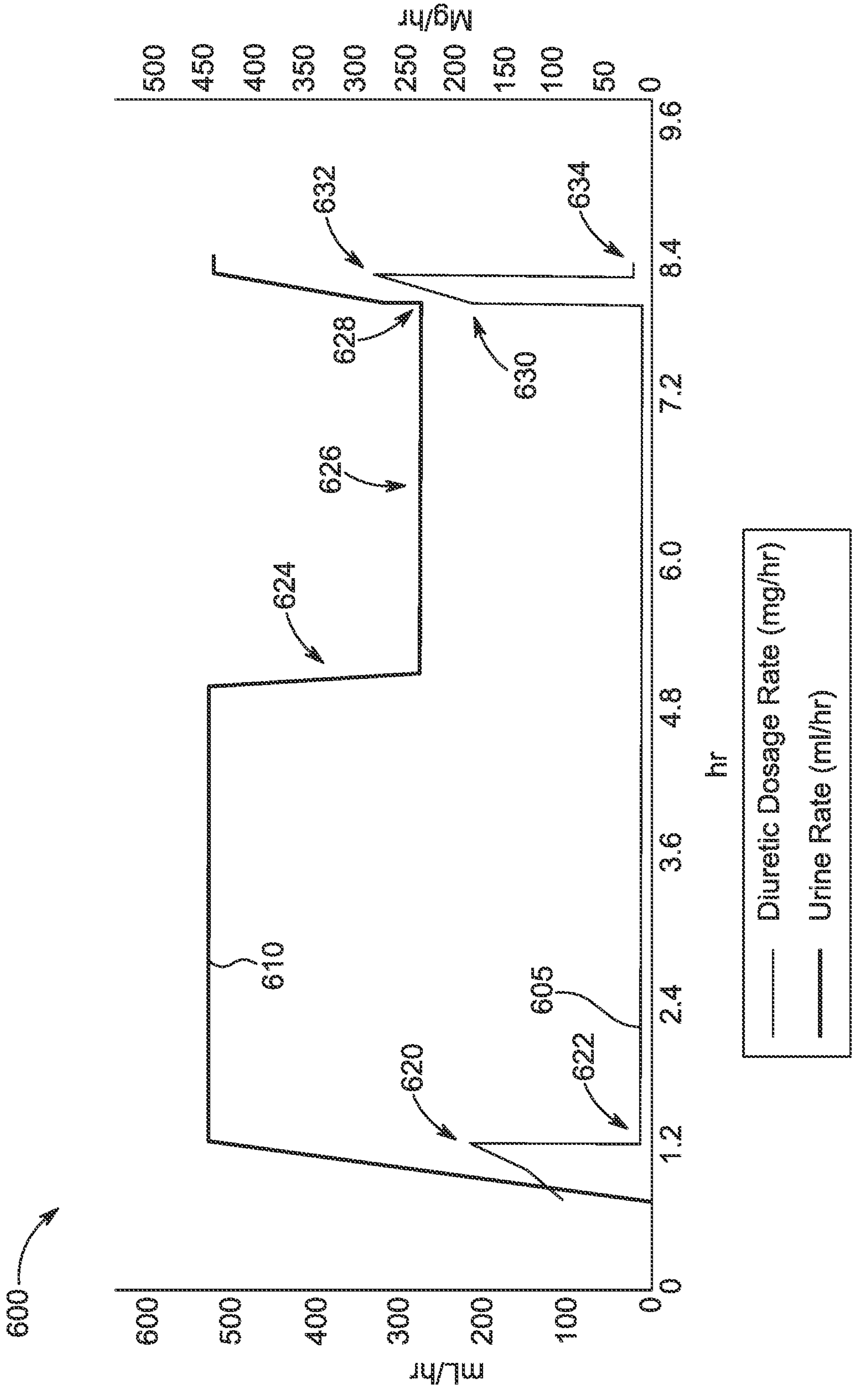
FIG. 6 is a graphical representation of diuretic dosage rate and corresponding urine output rate, in accordance with embodiments of the present technology.

FIG. 6 is a graphical representation 600 of diuretic dosage rate 605 and corresponding urine output rate 610, in accordance with embodiments of the present technology. The graphical representation 600 generally illustrates the embodiments described with reference to FIG. 5. Initially, the diuretic dosage rate 605 is increased or ramped until the urine rate 610 reaches a predetermined threshold, which in this instance is approximately 525 ml/hr. Once the predetermined threshold is reached, the ramp of the diuretic dosage rate 605 ceases (e.g., at point 620), and the diuretic dosage rate 605 is set to a percentage (e.g., 10%, 15%, 20%, 25%, 30%, or within a range of 10-30%) of the total diuretic dose delivered to the patient up to that point in time. For the embodiment illustrated in FIG. 6, the ramp of the diuretic dosage rate 605 completes at the point 620 after 50 mg of diuretic has been delivered, and the diuretic dosage rate 605 is thereafter set to 10 mg/hr or 20% of the total diuretic infused up to that point. The decreased diuretic dosage rate 605 can then be provided at the continuous rate of 10 mg/hr until the system causes the dosage rate 605 to be adjusted, e.g., in response to the urine rate dropping and/or a regulatory limit being met.

As illustrated by line 624, the urine rate 610 may decrease to a lower urine rate, as illustrated by line 626. This drop is urine rate 610 may be due to a change in the patient's response to the diuretic or other condition. Though the urine rate after line 624 is now below the predetermined threshold of 525 ml/hour, the diuretic dosage rate may not be immediately adjusted. Instead, as described elsewhere herein (e.g., with reference to FIG. 5), the diuretic dosage rate 605 may be adjusted only after (i) the urine rate is below another predetermined threshold (e.g., a second predetermined threshold) (e.g., 250 ml/hr, 300 ml/hr, 325 ml/hr, 350 ml/hr, 400 ml/hr, or 250-400 ml/hr) for a predetermined period of time (e.g., 2 hours, 2.5 hours, or 3 hours), or (ii) more than a predetermined amount (e.g., 100 ml, 125 ml, 150 ml, 175 ml) of debt has accumulated over the second predetermined period of time. Using these time-weighted average measurements of urine rate, as opposed to an instantaneous drop below the first predetermined threshold, to initiate a reramp of the diuretic dosage can prevent unnecessary reramps when, for example, the drop in urine rate 610 is due merely to a blocked Foley catheter, temporary faulty sensor, or other related short-term measure. At point 628, the system determines that the average urine rate has been below the second predetermined threshold for 3 hours. As a result, a reramp of the diuretic dosage rate 605 is initialized and the dosage rate is set to the rate at which the previous ramp ceased (as shown at point 630), in this instance approximately 180 mg/hr. The diuretic dosage rate 605 is then ramped according to the same conditions described elsewhere herein (e.g., with reference to FIGS. 2A-4). In some embodiments, the initial diuretic dosage rate 605 for the reramp can be set to a rate below (e.g., 10%, 20%, 30%, or 10-30% below) the rate at which the previous ramp ceased. Once the urine output rate reaches the predetermined threshold, the ramp of the diuretic dosage rate 605 ceases (i.e., at point 632), and the diuretic dosage rate 605 is set to a percentage, in this instance 20%, of the total diuretic dose delivered to the patient up to that point. For the embodiment illustrated in FIG. 6, the ramp of the diuretic dosage rate 605 completes at the point 632 after 50 mg of diuretic has been delivered via the second ramp or a total of 100 mg of diuretic (i.e., 50 mg from the second ramp and 50 mg previously delivered to the patient during the previous ramp ending at point 620), and the diuretic dosage rate 605 is thereafter set to 20 mg/hr or 20% of the total diuretic infused up to that point. The decreased diuretic dosage rate 605 can then be provided at the continuous rate of 20 mg/hr until the system causes the dosage rate 605 to be adjusted.

III. Down-titration or Decrease of Diuretic Dosage Rate

Figure 7:
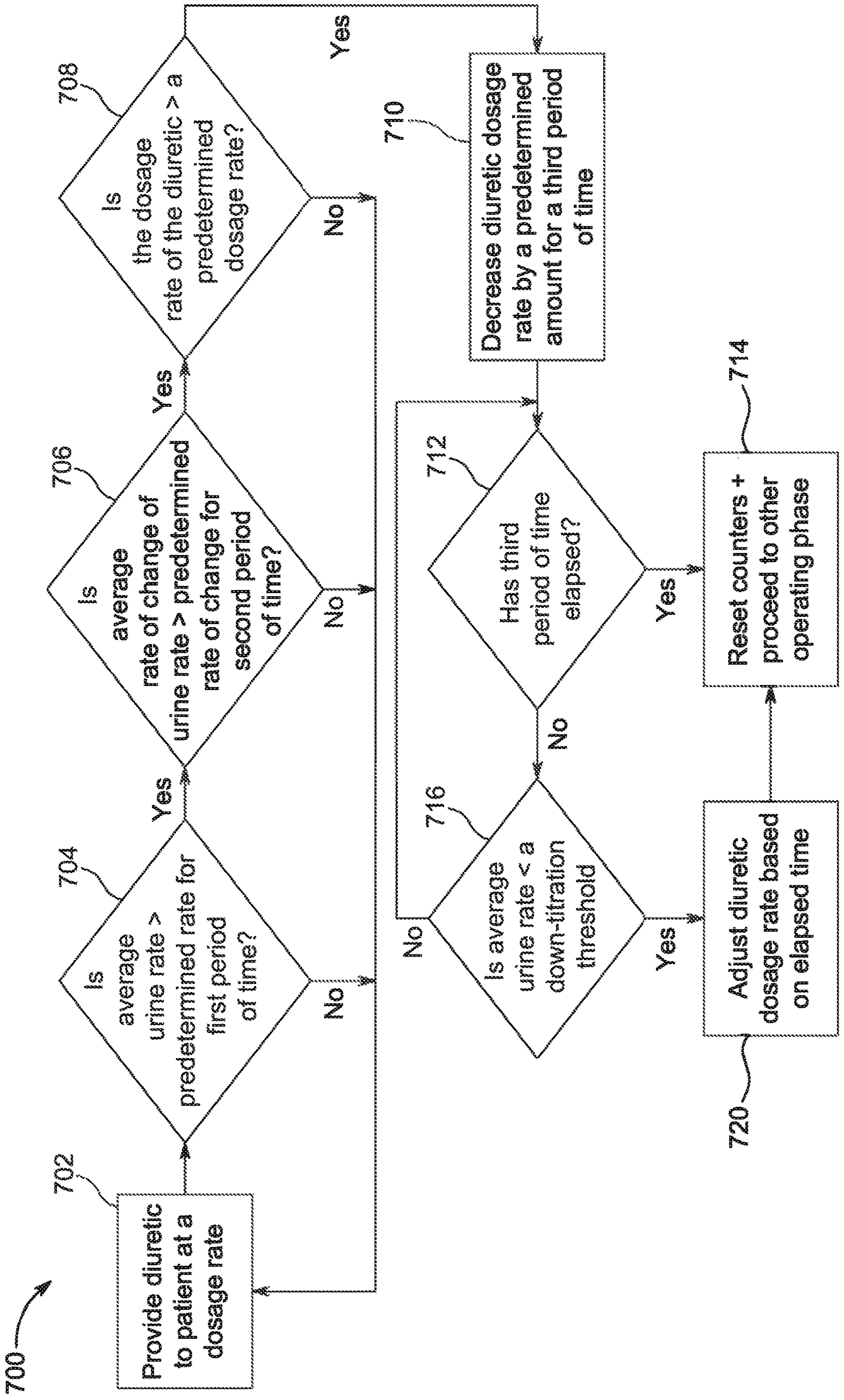
FIG. 7 is a flowchart illustrating down-titration or decrease of a diuretic dosage rate, in accordance with embodiments of the present technology.

FIG. 7 is a flowchart 700 illustrating down-titration of a diuretic dosage rate, in accordance with embodiments of the present technology. Fluid removal from a patient can often lead to physiological changes, which may cause an increased response to a diuretic dosage. In such instances, the urine rate may remain higher than clinically desired, which when left untreated over long periods of time can cause electrolyte loss and/or hypotension. Additionally, in such instances, it may also be desired to not simply cease providing diuretic to the patient, as doing so could unnecessarily cause fluid therapy to have to be restarted and thus increase the overall time needed to remove a net amount of excess fluid. To mitigate such issues, embodiments of the present technology can include a methodology for down-titrating (i.e., reducing) the diuretic dosage without setting the diuretic dosage to zero.

As shown in FIG. 7, the flowchart 700 begins by providing a diuretic to a patient at a dosage rate (process portion 702), as described elsewhere herein. The system then determines whether each one of a set of conditions is met, and if so down-titrates the diuretic dosage. The set of conditions can include determining whether the average urine rate is greater than a predetermined rate for a first period of time (e.g., 2 hours, 3 hours, 4 hours, or within a range of 2-4 hours) (process portion 704). The predetermined rate can be dependent on whether hydration fluid is being infused to the patient. If hydration fluid is being infused to the patient, the predetermined rate can be 900 ml/hr, 950 ml/hr, 1025 ml/h, 1100 ml/hr, or within a range of 900-1100 ml/hr. If no hydration fluid is being infused to the patient, the predetermined rate can be 400 ml/hr, 450 ml/hr, 525 ml/hr, 600 ml/hr, or within a range of 400-600 ml/hr. The set of conditions can further include determining whether an average rate of increase of the urine rate (e.g., a positive slope) is greater than a predetermined rate of change (e.g., 30 $ml/hr^2$, 40 $ml/hr^2$, 50 $ml/hr^2$, 60 $ml/hr^2$, 70 $ml/hr^2$, or within a range of 30-70 $ml/hr^2$) for a second period of time (e.g., 1 hour, 2 hours, 3 hours, or within a range of 1-3 hours) (process portion 706). The set of conditions can further include determining whether the diuretic dosage rate is greater than a predetermined dosage rate (e.g., 8 mg/hr, 10 mg/hr, 12 mg/hr, or within a range of 8-12 mg/hr) (process portion 708). In some embodiments, if any one of the set of conditions is not met, the system will not down-titrate the diuretic dosage and will revert to process portion 702. If each one of the set of conditions is met, the system will proceed to decrease the diuretic dosage rate by a predetermined. In some embodiments, the system may proceed to decrease the diuretic dosage per process portion 710 if two of the three conditions are met.

In some embodiments, by requiring all or a majority of the set of conditions to be met, the system avoids unnecessarily decreasing the diuretic dosage rate, thereby allowing urine rates to remain high and preventing fluid therapy from being unnecessarily interrupted. For example, whereas other methodologies may interrupt fluid therapy and decrease the diuretic dosage rate when the urine rate is merely above a predetermined threshold, embodiments of the present technology may only decrease the dosage rate (per process portion 710) when the urine rate is both high and increasing. Stated differently, such a methodology can prevent the diuretic dosage rate from being unnecessarily decreased when urine rates are high (e.g., above the predetermined rate) temporarily but are trending downward to eventually be below the predetermined rate. In doing so, embodiments of the present technology can also prevent or inhibit over-diuresis or excess fluid loss and/or electrolyte loss, as well limit unnecessary exposure of the patient to additional medical agents. Additionally or alternatively, down-titrating the diuretic dosage rate, as opposed to ceasing the diuretic dosage can be beneficial, as fluid therapy can be continued (albeit at lower urine rates) without the need to restart completely. Additionally or alternatively, by mitigating the potential hazard of diuretic overshooting (e.g., when ramping the diuretic during the dosage determining phase) and limiting overexposure of the patient to the diuretic, there may be additional regulatory benefits to having the down-titration methodology.

If the set of conditions are met, the system can decrease the diuretic dosage rate by a predetermined percentage (e.g., 20%, 25%, 30%, or within a range of 20-30%) for a third period of time (e.g., 2 hours, 3, hours, 4 hours, or within a range of 2-4 hours) (process portion 710). After decreasing the diuretic dosage, the system checks whether the third period of time has elapsed (process portion 712), and if so resets the counters associated with the set of conditions (process portion 714). In such embodiments, the diuretic dosage rate can remain at the down-titrated levels or be adjusted based on the subsequent operating phase of therapy. If the third period of time has not elapsed, the system may determine whether the average urine rate is greater than a down-titration threshold (process portion 720). The down-titration threshold may be based on the predetermined rate used in process portion 704. For example, the down-titration threshold can be 100 ml/hr less than the predetermined rate. In such embodiments, the down-titration threshold can be 800 ml/hr, 850 ml/hr, 925 ml/h, 1000 ml/hr, or within a range of 800-1000 ml/hr when hydration fluid is being infused, and 300 ml/hr, 350 ml/hr, 425 ml/hr, 500 ml/hr, or within a range of 300-500 ml/hr if no hydration fluid is being infused. If the average urine rate is less that the down-titration threshold, the diuretic dosage rate can be adjusted (e.g., increased) based on the elapsed time at that moment in time. In some embodiments, the predetermined percentage that the diuretic dosage rate decreased per process portion 710 is reduced by the fraction of the third period that has elapsed. For example, assuming the predetermined percentage was 25%, if the diuretic dosage rate drops below the down-titration threshold 90 minutes after the down-titration began (i.e., half of the third period of time of 180 minutes), the diuretic dosage rate would then be increased to be only half of the predetermined percentage, or 12.5%. After the diuretic dosage is adjusted per process portion 720, the system can reset the counters associated with the set of conditions (process portion 714), as previously described.

Figure 8:
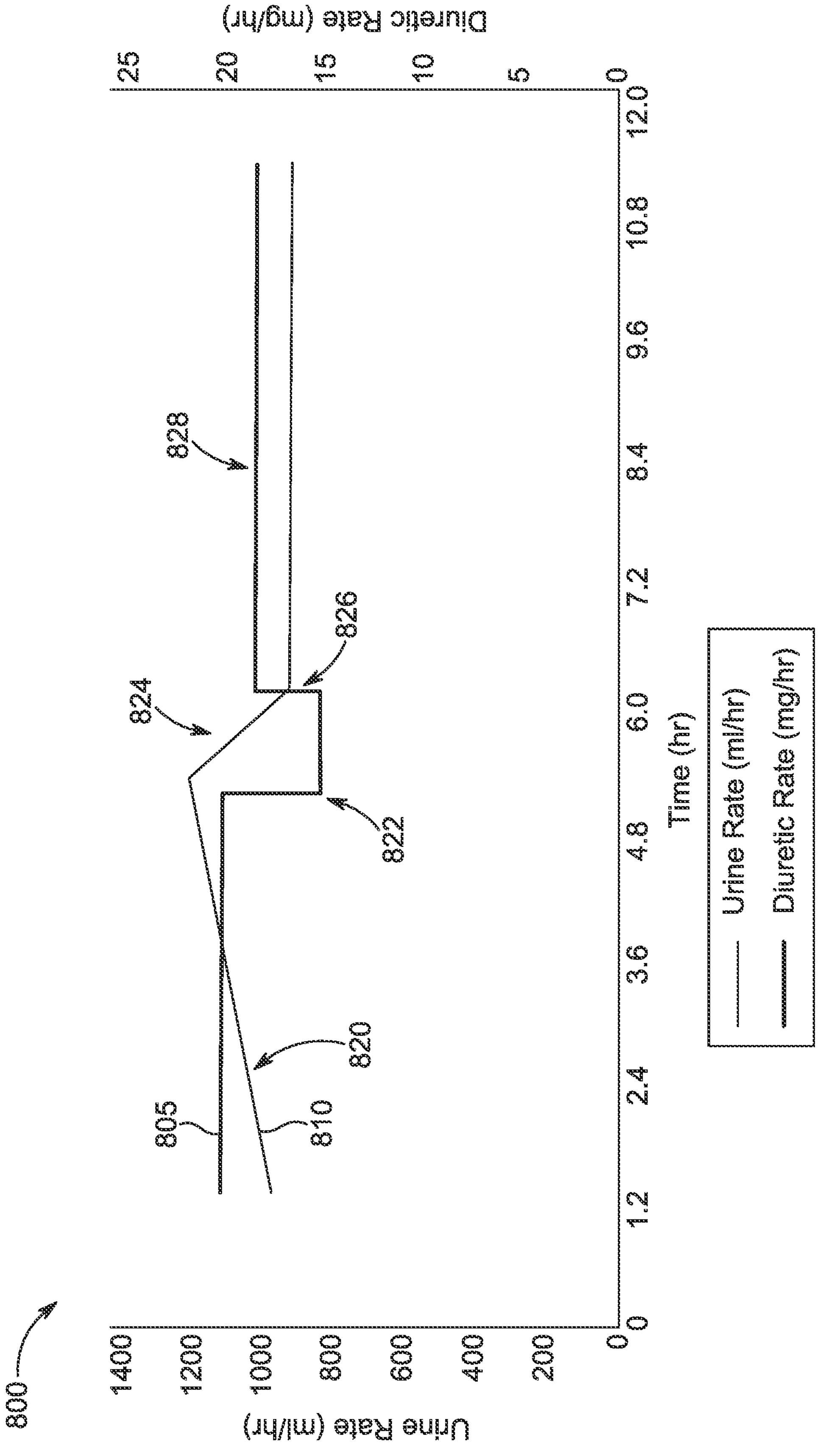
FIG. 8 is a graphical representation of down-titrating or decreasing a diuretic dosage rate, in accordance with embodiments of the present technology.

FIG. 8 is a graphical representation 800 of down-titrating a diuretic dosage rate 805, in accordance with embodiments of the present technology. The graphical representation 800 generally illustrates the embodiments described with reference to FIG. 7. As shown in FIG. 8, the diuretic dosage rate 805 is initially steady at a rate of approximately 20 mg/hour, and the urine rate 810 is increasing at a rate greater than 50 ml/hr$^2$. Approximately at point 820, the urine output exceeds 1025 ml/hr. At point 822, each one of the set of conditions described with reference to FIG. 7 is met. That is, (i) the average urine rate 810 has been above a predetermined rate of 1025 ml/hr for a first period of time of 3 hours, (ii) the average rate of change of the urine rate is above a predetermined rate of change of 50 ml/hr$^2$, and (iii) the diuretic dosage rate is above a predetermined dosage rate of 10 mg/hr. As such, the diuretic dosage rate at point 822 is decreased by a predetermined percentage, in this instance 25%, from 20 mg/hr to 15 mg/hr for a period of time, in this instance 3 hours. Decreasing the diuretic dosage rate 805 causes the urine rate to drop, as illustrated by portion 824. Once the urine output reaches a down-titration threshold of 925 ml/hr at point 826, the diuretic dosage rate is increased. Since the down-titration threshold was reached one hour after the down-titration event (i.e. ⅓ of the 3 hour period of time), the diuretic dosage rate is subsequently set to be ⅓ (33%) of the original 25% reduction or 8.3% less than the original diuretic dosage rate of 20 mg/hr. Accordingly, the diuretic dosage rate is set to approximately 18.3 mg/hr. Point 828 corresponds to 3 hours of elapsed time since the down-titration event, and thus at that time the down-titration check is re-engaged. Stated differently, the down-titration feature is disabled for a period of time, in this instance 3 hours, after a down-titration event occurs.

Figure 9:
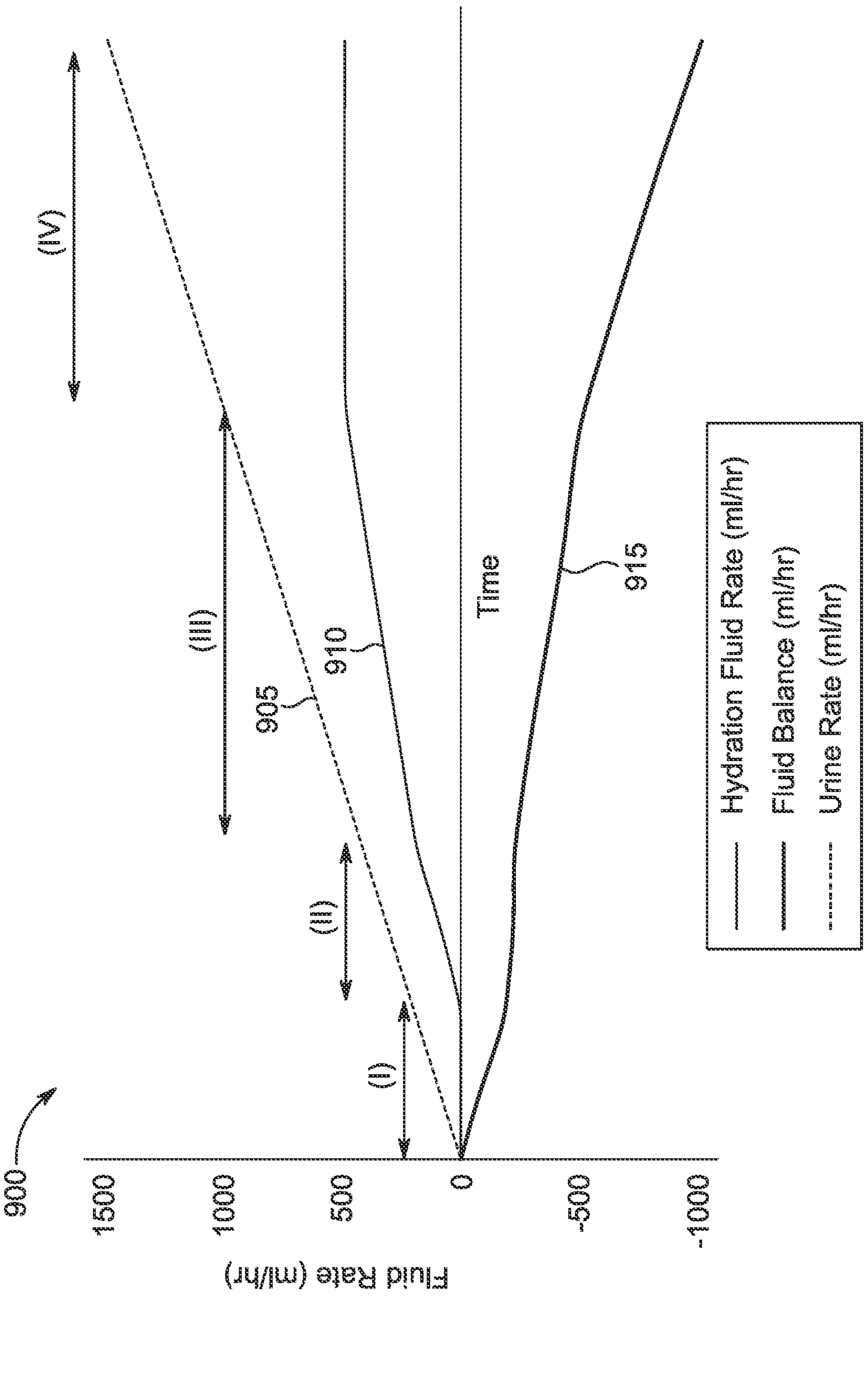
FIG. 9 is a graphical representation of the relationship between urine output rate, hydration fluid infusion rate, and net fluid balance, in accordance with embodiments of the present technology.

FIG. 9 is a graphical representation 900 of the relationship between urine output rate 905, hydration fluid infusion rate 910, and net fluid balance 915, in accordance with embodiments of the present technology. As described elsewhere herein, embodiments of the present technology enable the urine rate 905 of a patient to be rapidly increased by increasing the diuretic dosage rate provided to the patient at a relatively fast rate, e.g., exponentially during the diuretic dosage determining phase (as described elsewhere herein). Simultaneously, hydration fluid can be infused at rates equal to or less than the diuretic dosage rates, to thereby enable net fluid balance over time. The hydration fluid infusion, e.g., during the diuretic dosage determining phase, may be done to "jumpstart" the patient's urination response. In some embodiments, the initial hydration fluid infusion can cause the patient to respond to the diuretic more quickly, and so, without being bound by theory, the initial hydration fluid may be infused in order to inhibit intravascular depletion, as well as inhibit drops in cardiac output and renal perfusion. As described elsewhere herein, in some embodiments the algorithm may control the hydration fluid infusion rate to substantially match (e.g., at least 90% or 100%) the urine output rate while administering the initial diuretic dosage (e.g., during the diuretic dosage ramp) for an initial amount (e.g., at least the initial 150 ml, 200 ml, 250 ml, 300 ml, 400 ml, 500 ml, or within a range of 150-500 ml) of urine output or for a first time period (e.g., the first hour, 2 hours, or 3 hours), whichever comes first. It is noted that the need for initial hydration fluid infusion may be determined more by the desire to achieve better patient response to the diuretic, as opposed to decreasing salt concentration of fluid levels, which may be the driving need for hydration fluid infusion in subsequent operating phases. For example, hydration fluid infusion during the fluid reduction phase or continuous infusion phase may be done to optimize net fluid removal while also avoiding safety risks, e.g., by maintaining a safe blood pressure and sodium level. That is, a goal of infusing hydration fluid is to maximize net fluid removal while avoiding adding too much sodium back and/or in any way increasing the likelihood of causing a hypotensive state.

As shown in FIG. 9, the urine rate may be classified into different regions, including a first region (I), a second region (II), a third region (III), and a fourth region (IV), with each subsequent region corresponding to a higher urine output rate 905. The first region (I) can correspond to a urine rate below a first threshold (e.g., 175 ml/hr, 225 ml/hr, 275 ml/hr, or within a range of 175-275 ml/hr), the second region (II) can correspond to a urine rate between the first threshold and a second threshold (e.g., 375 ml/hr, 425 ml/hr, 500 ml/hr, or within a range of 375-500 ml/hr), the third region (III) can correspond to a urine rate between the second threshold and a third threshold (e.g., 975 ml/hr, 1025 ml/hr, 1100 ml/hr, or within a range of 975-1100 ml/hr), and the fourth region (IV) can correspond to a urine rate above the third threshold. As shown in FIG. 9, as the urine rate 905 increases, the hydration rate 910 generally increases as well, but at a rate less than that of the urine rate 905. In doing so, the net fluid balance 915 decreases (i.e., becomes more negative) and net fluid loss increases. Urine output rate is continuously calculated throughout the treatment so the algorithm can respond to changes quickly. For example, flow, weight, volume, and/or other characteristics indicative of volumetric rate change of the urine may be measured every minute, and the urine output rate 905 can be calculated every minute based on a previous time period (e.g. 5 minutes, 10 minutes, 20 minutes, or within a range of 5-20 minutes). Assessing how much hydration fluid to infuse may occur every minute.

As shown in FIG. 9, when urine rate 905 is in the first region (I) below the first threshold, the hydration fluid rate 910 may be zero, or a minimum amount (e.g., 10 ml/hr), e.g., to keep the vein pressurized and open (referred to as a Keep Vein Open (KVO) rate). Since the urine output is low in the first region, rehydration is less or not necessary, Also, as a general goal is to maximize net fluid removal, no infusion of hydration fluid may be provided when the urine rate 905 is in the first region (I). As previously described, in some embodiments, the hydration fluid rate 910 may match the urine rate 905 for a first period of time or until a minimum amount of hydration fluid is infused.

When the urine rate 905 is in the second region (II), substantially all (e.g., at least 90% or 100%) of the urine volume in the second region (II) (i.e., between the first and second thresholds) is replaced by hydration fluid, e.g., to ensure the kidneys are getting enough fluid and salt, and to inhibit a hypotensive state.

When the urine rate 905 is in the third region (III), substantially all (e.g., at least 90% or 100%) of the urine volume in the second region (II) between the first and second thresholds can be replaced by hydration fluid, and 40%, 45%, 50%, or a range of 40-50% of the urine volume above in the third region (III) and above the second threshold is replaced. By only replacing a portion of the urine rate above the second threshold, net fluid balance as well as salt concentration can be decreased. Urine typically has less sodium concentration than blood or normal saline, which is approximately 154 mmol/L. As such, replacing urine with an equal amount of hydration fluid may result in increased and undesirable sodium levels. In some embodiments, providing saline or hydration fluid at a rate of more than 50% of the urine rate can increase the risk of giving them more sodium than they are releasing. Accordingly, limiting the hydration fluid rate to 50% can protect patients having low sodium urine, while also enabling patients having higher sodium urine to experience faster net fluid and sodium removal. Urine output rate in the third region (III) can serve as an indication that the kidneys are functioning well and not in a hypotensive state, and so the reduced hydration fluid rate is more acceptable.

When the urine rate 905 is the fourth region (IV), substantially all (e.g., at least 90% or 100%) of the urine volume in the second region (II) between the first and second thresholds can be replaced by hydration fluid, 40%, 45%, 50%, or a range of 40-50% of the urine volume in the third region (III) between the second and third thresholds can be replaced, and none of the urine volume in the fourth region (IV) above the third threshold is replaced. In doing so, the net fluid balance can be further decreased.

It was previously thought that removing high excess fluid amounts (e.g., greater than 5 L) within 24 hours with conventional therapy methods would be dangerous and could cause hypotension. However, embodiments of the present technology have shown that even at relatively high urine rates (e.g., at urine rates within the third or fourth regions), removing excess fluid amount (e.g., via infusing hydration fluid at 50% replacement) of at least 5 L per day can be safely done with limited or no risk of kidney failure.

In some embodiments, a net fluid loss limit may be set based on the urine rate at the time and/or region the urine rate is in, with the net fluid loss limit increasing for each subsequent region. For example, the net fluid loss limit for (i) the first region (I) can be 80 ml/hr, 90 ml/hr, 100 ml/hr, or within a range of 80-100 ml/hr, (ii) the second region (II) can be 100 ml/hr, 130 ml/hr, 160 ml/hr, or within a range of 100-160 ml/hr, (iii) the third region (III) can be 250 ml/hr, 400 ml/hr, 500 ml/hr, or within a range of 250-500 ml/hr, and (iv) the fourth region (IV) can be 500 ml/hr, 750 ml/hr, 900 ml/hr, or within a range of 500-1000 ml/hr.

IV. Methods for Causing Net Fluid Loss from a Patient

Figure 10:
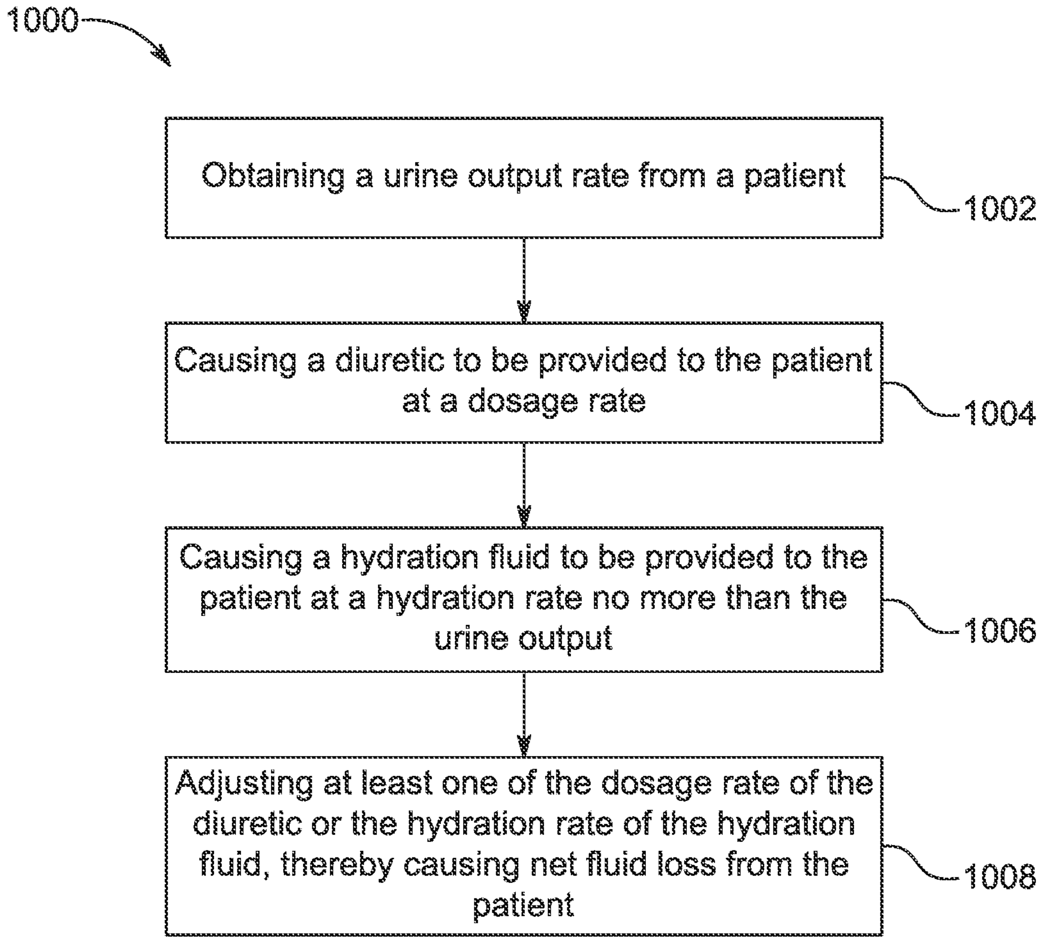
FIGS. 10 and 11 are flow diagrams of methods for causing net fluid loss from a patient, in accordance with embodiments of the present technology.

FIG. 10 is a flow diagram of a method 1000 for causing net fluid loss from a patient, in accordance with embodiments of the present technology. The method 1000 can be implemented via a computer, a controller, and/or in the form of executable tangible, non-transitory computer-readable media. For example, the method 1000 can correspond to executable instructions that are executed by one of more processors that are part of a console or associate device.

The method 1000 can include obtaining a urine output rate from a patient (process portion 1002), e.g., by receiving an input from a flow, volumetric, weight, optical or other sensor for determining flow. The urine rate can be an average rate measured over the previous 5 or 10 minutes and be updated on a continuous or recurring basis (e.g., every 30 seconds, 1 minutes, 2 minutes, etc.).

The method 1000 can include causing a diuretic to be provided to the patient at a dosage rate (process portion 1004). The diuretic can comprise furosemide, bumetanide, ethacrynic acid, torsemide, and/or other diuretics known in the art, and may be part of a solution including saline or other hydration fluid mixed therewith. The diuretic can be provided to the patient as part of a diuretic dosage determining phase, as described elsewhere herein (e.g., with reference to FIGS. 2A-4B). For example, the diuretic can be provided at an initial dosage and then increased in a rapid manner. In some embodiments, the diuretic dosage rate can be increased exponentially and/or in a manner that doubles the diuretic dosage rate or total diuretic within a period of time (e.g., 10 minutes, 15 minutes, 20 minutes, or within a range of 10-20 minutes).

The method 1000 can include causing a hydration fluid to be provided to the patient at a hydration rate no more than the urine output rate (process portion 1006). The hydration fluid can comprise saline or other fluids having sodium. The hydration fluid can be provided to the patient based on the corresponding urine rate. For example, as described elsewhere herein, the hydration fluid rate may be determined based on whether the urine rate is above or below a number of different thresholds (e.g., the first threshold, second threshold, and third threshold described with reference to FIG. 9), with the difference between the urine rate and each threshold increasing as the urine rate increases. In some embodiments, the hydration fluid may substantially match the urine rate for an initial amount (e.g., at least the initial 150 ml, 200 ml, or 250 ml) of urine provided to the patient and/or for an initial time period (e.g., the first hour, 2 hours, or 3 hours).

The method 1000 can include adjusting at least one of the dosage rate of the diuretic or the hydration rate of the hydration fluid, thereby causing net fluid loss from the patient (process portion 1008). In this regard, the difference between the diuretic dosage rate and the hydration rate may be increased by increasing the diuretic dosage rate, increasing the diuretic dosage rate relative to the hydration fluid, and/or decreasing the hydration fluid. As described elsewhere, adjusting one or both of the diuretic dosage rate and hydration fluid rate may be done while also requiring a minimum fluid loss limit.

In some embodiments, adjusting the dosage rate of the diuretic can comprise ramping or reramping the diuretic dosage. Determining whether to initiate a reramp can be based upon a set of conditions (e.g., the set of conditions described with reference to process portion 510; FIG. 5). For example, a trigger for the reramp may require determining whether (i) the average urine rate is below a predetermined threshold rate (e.g., 250 ml/hr, 300 ml/hr, 325 ml/hr, 350 ml/hr, or 400 ml/hr) for a predetermined period of time (e.g., 2 hours, 2.5 hours, or 3 hours), and/or (ii) more than a predetermined amount (e.g., 100 ml, 125 ml, 150 ml, 175 ml) of debt has accumulated over the predetermined period of time. As previously described, debt can be defined as the area below a threshold (e.g., 250 ml/hour, 275 ml/hour, 325 ml/hr, or within a range of 250-325 ml/hr) and above the current urine rate over a given period of time. If one of these conditions is met, a reramp may be initialized.

The reramp can occur after an initial ramp of the diuretic (e.g., during the diuretic dosage determining phase) and in response to the urine rate dropping below a threshold. For example, as described with reference to FIGS. 5 and 6, if the urine rate (e.g., the average urine rate) is determined to be low, based on a set of conditions, the system can begin to reramp the diuretic dosage rate, e.g., after receiving confirmation from the patient that it is ok to do so. The reramp can be implemented in a manner similar to the diuretic dosage determining phase, in that the diuretic dosage rate is increased rapidly until a period of time elapses and/or a urine rate of the patient rises above a predetermined threshold. For example, in such embodiments, the diuretic dosage is incrementally increased exponentially, such that each diuretic dosage rate is greater than the immediately previous diuretic dosage rate, e.g., by at least 50%, 75%, 100%, or within a range of 50-100%. In such embodiments, the diuretic dosage rate can effectively double one or more times throughout a particular ramp or diuretic dosage determining phase. At such time that the ramp ceases due to the period of time elapsing or the urine rate rising above the predetermined threshold, the diuretic dosage rate can be further adjusted, e.g., by setting the diuretic dosage to be a percentage of the total diuretic delivered up to that point. The total amount of diuretic delivered can include that delivered during the reramp and, if applicable, any previous ramp that occurred.

The ramp and reramp feature of embodiments of the present technology can be beneficial to the user and fluid therapy generally, as it allows the urine rate of the patient to increase as quickly as possible, while also maintaining safe levels of intravascular volume (e.g., by infusing hydration fluid) so as to minimize the risk of hypotension and drops in cardiac output and renal perfusion. Additionally or alternatively, the ramp and reramp features, in combination with other features, of embodiments of the present technology also enable the patient, operator, or system itself to treat patients and relieve them of excess fluid conditions quickly. That is, embodiments of the present technology have been shown to remove fluid amounts in excess of 7.5 L over timespans of less than 24 hours. Moreover, because embodiments of the present technology are configured to rapidly increase a patient's urine rate in a relatively short time period, the system can also automatically determine if the patient is not responding appropriately to a particular fluid therapy. That is, if after providing the diuretic according to the ramp or diuretic dosage determining phase, as described herein, the patient's urine rate does not increase in the manner expected, this may indicate that the patient is diuretic resistant of that another problem exists requiring further investigation. Accordingly, embodiments of the present technology can enable issues such as diuretic resistance to be discovered and subsequently treated of dealt with in a shorter period of time than other conventional technologies.

Figure 11:
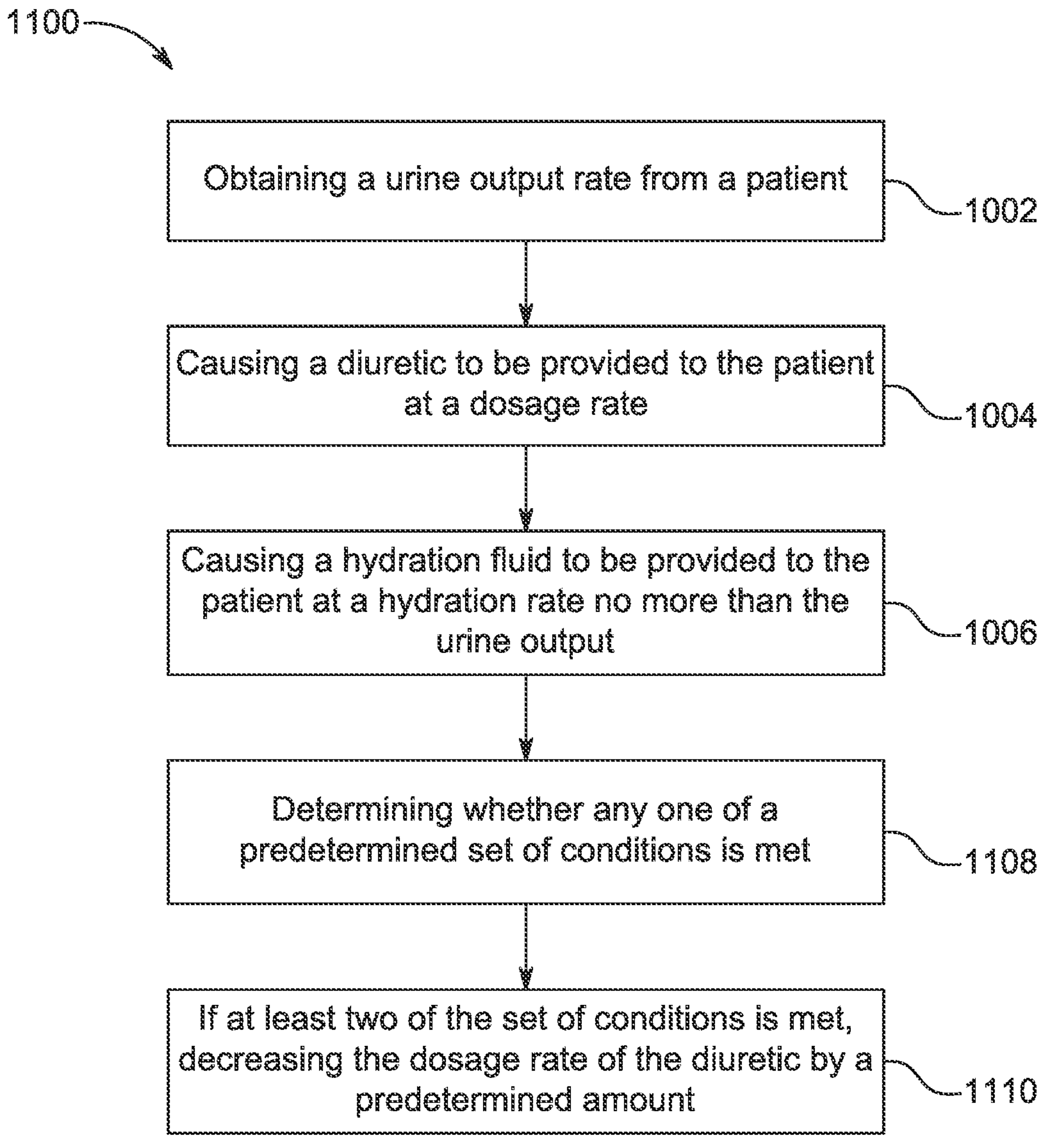

FIG. 11 is a flow diagram of a method 1100 for causing net fluid loss from a patient, in accordance with embodiments of the present technology, in accordance with embodiments of the present technology. The method 1100 can be implemented via a computer, a controller, and/or in the form of executable tangible, non-transitory computer-readable media. For example, the method 1100 can correspond to executable instructions that are executed by one of more processors that are part of a console or associate device. The method 1100 can include process portions 1002, 1004, 1006, as described with reference to FIG. 10.

The method 1100 can include determining whether any one of a predetermined set of conditions is met (process portion 1108), e.g., to determine whether the urine rate is too high. The set of conditions can correspond to those described with reference to FIG. 7 (e.g., process portions 704, 706, 708) and FIG. 8. For example, the set of conditions can include determining whether the average urine rate is greater than a predetermined rate for a first period of time (e.g., 2 hours, 3 hours, 4 hours, or within a range of 2-4 hours). The predetermined rate can be dependent on whether hydration fluid is being infused to the patient. If hydration fluid is being infused to the patient, the predetermined rate can be 900 ml/hr, 950 ml/hr, 1025 ml/h, 1100 ml/hr, or within a range of 900-1100 ml/hr. If no hydration fluid is being infused to the patient, the predetermined rate can be 400 ml/hr, 450 ml/hr, 525 ml/hr, 600 ml/hr, or within a range of 400-600 ml/hr. The set of conditions can further include determining whether an average rate of change of the urine rate (i.e., a slope) is greater than a predetermined rate of change (e.g., 30 ml/$hr^2$, 40 ml/$hr^2$, 50 ml/$hr^2$, 60 ml/$hr^2$, 70 ml/$hr^2$, or within a range of 30-70 ml/$hr^2$) for a second period of time (e.g., 1 hour, 2 hours, 3 hours, or within a range of 1-3 hours). The set of conditions can further include determining whether the diuretic dosage rate is greater than a predetermined dosage rate (e.g., 8 mg/hr, 10 mg/hr, 12 mg/hr, or within a range of 8-12 mg/hr).

The method 1100 can include, if at least two of the set of conditions is met, decreasing the dosage rate of the diuretic by a predetermined amount. That is, if two or three of the following conditions are met, the dosage rate may be decreased: (i) the average urine rate is greater than the predetermined rate for the first period of time, (ii) the average rate of change of the urine rate is greater than the predetermined rate of change, and (iii) the diuretic dosage rate is greater than the predetermined dosage rate. In some embodiments, each one of the set of conditions must be met in order to decrease the dosage rate of the diuretic by a predetermined amount. By requiring all or a majority of the set of conditions to be met, the system avoids unnecessarily decreasing the diuretic dosage rate, thereby allowing urine rates to remain high and preventing fluid therapy from being unnecessarily interrupted. For example, whereas other methodologies may interrupt fluid therapy and decrease the diuretic dosage rate when the urine rate is just too high, embodiments of the present technology may only decrease the dosage rate (per process portion 1110) when the urine rate is both high and increasing. Stated differently, such a methodology can prevent the diuretic dosage rate from being unnecessarily decreased when urine rates are high (e.g., above the predetermined rate) temporarily but are trending downward to eventually be below the predetermined rate. In doing so, embodiments of the present technology can also prevent or inhibit over-diuresis, excess fluid loss and/or electrolyte loss, as well limit unnecessary exposure of the patient to additional diuretic. Additionally or alternatively, down-titrating the diuretic dosage rate, as opposed to ceasing the diuretic dosage, is beneficial, as fluid therapy can be continued (albeit at lower urine rates) without the need for a complete restart. This allows net fluid balance to continue to increase even during the down-titration event, as opposed to ceasing the fluid therapy and thereby halting net fluid loss increases. Additionally or alternatively, by mitigating the potential hazard of diuretic overshooting (e.g., when ramping the diuretic during the dosage determining phase) and limiting overexposure of the patient to the diuretic, there may be additional regulatory benefits to having the down-titration methodology.

Decreasing the dosage rate of the diuretic by a predetermined amount can correspond to the down-titration methodology described elsewhere herein with reference to FIG. 7 (e.g., process portion 710, 712, 714, 716, 720) and FIG. 8. For example, decreasing the dosage rate of the diuretic can comprise decreasing the diuretic dosage by a predetermined percentage (e.g., 20%, 25%, 30%, or within a range of 20-30%) for a period of time (e.g., 2 hours, 3, hours, 4 hours, or within a range of 2-4 hours). In some embodiments, after decreasing the diuretic dosage and once the period of time has elapsed, the counters associated with the set of conditions may be reset. In such embodiments, the diuretic dosage can remain at the down-titrated levels or be adjusted based on the subsequent operating phase of therapy. If the third period of time has not elapsed and the average urine rate drops below a down-titration threshold, the diuretic dosage rate can be adjusted (e.g., increased) based on the elapsed time at that moment. In some embodiments, the predetermined percentage that the diuretic dosage rate is decreased by is reduced by the fraction of the period of time that has elapsed. For example, assuming a predetermined percentage of 25% and a period of time of 3 hours, if the diuretic dosage drops below the down-titration threshold 90 minutes after the down-titration began, the diuretic dosage would then be increased to be only half of the predetermined percentage, or 12.5%. After the diuretic dosage is adjusted per process portion 1110, the counters associated with the set of conditions may be reset, as previously described.

V. Example: Fluid Overload Therapy with Diuretics and Hydration Fluid

The following example is included to further describe some aspects of the present technology, and should not be used to limit the scope of the invention.

Clinical data associated with embodiments of the present technology were obtained from patient tests conducted at the Tbilisi Heart and Vascular Center in Tbilisi, Georgia. 15 patients underwent fluid therapy in which diuretic(s) and hydration fluid were administered via the Reprieve Cardiovascular™ Second Generation System according to the methods described herein ("treatment group"). As described below, data obtained from the tests indicate that the net fluid loss and net sodium loss levels achieved represent a significant improvement over conventional methods for treating fluid overload conditions, and generally indicate that embodiments of the present technology produce improved diuresis and renal safety.

Table 1 below indicates total urine output, net fluid loss (not including intake fluid), net fluid loss (including intake fluid), net sodium balance, and average diuretic (Lasix) dosage rate for each patient in the treatment group, as measured across a therapy timespan. As shown in Table 1, the average net fluid loss (not including oral fluid intake) for patients in the treatment group was nearly 7 liters (L) over an average therapy timespan of 31 hours. When normalized over a 24-hour period for each patient, average net fluid loss was approximately 5.4 L. Compared to patients undergoing conventional fluid therapy treatment (i.e., administered diuretic with no replacement hydration fluid) ("control group"), which achieved an average net fluid loss of 1.75 L over a normalized 24-hour period, the treatment group showed over 200% increase in net fluid loss. Additionally, the average therapy timespan for the treatment group was 31 hours, whereas the average therapy timespan for standard of care therapy in the literature is approximately 5 days. Accordingly, the combined diuretic and hydration fluid treatment was able to achieve significantly more net fluid loss and decreased overall therapy time relative to conventional treatments. During the treatment, the patients in the treatment group also showed an average weight loss of 6.8 kilograms (kg) at the time of patient discharge, and an average loss of 5.7 kg after 30 days. Over the 30 days, none of the patients in the treatment group regained the weight that lost during therapy or were readmitted for additional treatment.

TABLE 1

Clinical data for treatment group patients

| Patient # | Total Urine (ml) | Net Fluid Loss (not including oral fluid intake) (ml) | Net Fluid Loss (including oral fluid intake) (ml) | Therapy Timespan (hh:mm) | Avg. Lasix/Hr (mg) |
|---|---|---|---|---|---|
| 1 | 9,162 | −4,704 | −3,844 | 23:49 | 13 |
| 2 | 14,158 | −6,001 | −4,868 | 30:34 | 44 |
| 3 | 11,456 | −4,590 | −4,247 | 24:51 | 10 |
| 4 | 6,329 | −2,993 | −2,232 | 21:03 | 36 |
| 5 | 19,728 | −11,913 | −10,787 | 53:44 | 82 |
| 6 | 3,726 | −2,003 | −1,021 | 26:06 | 44 |
| 7 | 12,966 | −8,306 | −6,276 | 45:55 | 79 |
| 8 | 12,179 | −6,941 | −5,625 | 27:01 | — |
| 9 | 6,496 | −3,953 | −3,636 | 21:10 | 25 |
| 10 | 20,184 | −12,269 | −10,299 | 50:43 | 15 |
| 11 | 8,328 | −4,364 | −3,724 | 19:06 | 58 |
| 12 | 17,784 | −9,995 | −9,156 | 29:07 | 27 |

TABLE 1-continued

Clinical data for treatment group patients

| Patient # | Total Urine (ml) | Net Fluid Loss (not including oral fluid intake) (ml) | Net Fluid Loss (including oral fluid intake) (ml) | Therapy Timespan (hh:mm) | Avg. Lasix/Hr (mg) |
|---|---|---|---|---|---|
| 13 | 14,629 | −7,888 | −6,583 | 33:40 | 29 |
| 14 | 12,930 | −7,018 | −6,186 | 21:34 | 30 |
| 15 | 21,155 | −11,333 | −10,301 | 40:08 | 7 |
| Average | 12,744 | −6,948 | −5,919 | 31 | 39 |

As also shown in Table 1, the average diuretic dosage rate was nearly 40 mg/hr, which corresponds to a daily dose of nearly 950 mg. This diuretic dosage rate and dose were significantly higher than corresponding dosage rate and dose for the conventional treatment methods, and thus contributed to the relative increased treatment efficacy of the embodiments of the present technology.

As also shown in Table 1, the average net sodium balance for all patients in the treatment group decreased by nearly 800 millimoles (mmol) over the therapy timespan. When normalized over a 24-hour period, the average and median net sodium balance was −14 grams (g) and −15 g respectively. Relative to conventional treatment methods, which showed a median net sodium balance of −3.63 g over a normalized 24-hour period, this represents an improvement of over 11 g or 300%.

Estimated glomerular filtration rate (eGFR) is a measure of kidney function and stage of kidney disease, and is based on patient factors including blood creatinine and a patient's age, body size, and gender. The patients in the treatment group showed an average increase in creatinine of 0.11 mg/dL (deciliter) and only a modest average decrease of 1.6 eGFR over a 30-day span. Such modest changes in eGFR, especially given the amount and rate of net fluid loss, indicate the fluid therapy was generally well tolerated by the patients and kidney function after therapy was largely maintained at pre-treatment levels.

Blood pressure measurements of the patients in the treatment group serve as another indication that the fluid therapy was well received by the patients. For example, the average mean arterial pressure (MAP) of patients dropped from 90.1 mmHg to 88.2 mmHg at the time of patient discharge, and then to 87.2 mmHg after 30 days. Additionally, average systolic pressure of the patients dropped from 121 mmHg to 119 mmHg at the time of patient discharge, and then to 117 mmHg after 30 days. Such modest changes in MAP and systolic pressure, especially given the amount and rate of net fluid loss, indicate the fluid therapy was generally well tolerated by the patients.

VI. Exemplary Functional Requirements of Embodiments of the Present Technology

User Interface

Displays

The software shall display the Urine Production Rate reported by the urine monitoring device.

The software shall display the Net Target, defined as the (Desired Fluid Balance)*(−1)+(Urine Buffer Range) (Note: Default Desired Fluid Balance is −225 and default Urine Buffer Range is 100, thus default Net Target is 325)

The software shall display the total urine over the previous hour ("Last Hour Urine")

The software shall display the total urine over the previous 2-hours ("Last 2-Hour Urine")

The software shall display the total urine over the previous 3-hours ("Last 3-Hour Urine")

The software shall display the total "Debt", defined as the area below the "Net Target" and above the "Urine Production Rate" over the previous three hours. If the urine production rate is above the "Net Target", "debt" is not added or removed.

The software shall display the Average Urine Rate over the previous hour.

The software shall display the time in the current mode.

The software shall display the total diuretic dose during the previous Ramp.

The software shall display the total urine measured by the urine monitoring device during the previous Ramp.

The software shall display the time the previous ramp exceeded the target urine rate (Note: default target urine rate is 525 ml/hr).

The software shall display the total diuretic infused since the start of therapy.

The software shall display the total diuretic infused during the previous 24 hours.

The software shall display the current diuretic infusion rate.

The software shall display the total saline infused since the start of therapy, as reported by the hydration fluid infusing device.

The software shall display the total urine measured since the start of therapy, as reported by the urine monitoring device.

The software shall display the measured net fluid balance ("Removed Volume" since the start of therapy, based on a difference between total urine output and total hydration fluid infused.

The software shall display the current fluid balance target.

The software shall plot the urine rate and may display the urine rate, such as an average rate over one or more periods of time, such as 15 minutes, 1 hour and/or three hours. The software shall plot the diuretic infusion rate on the same plot as the urine rate.

The software shall provide the user the ability to adjust the time scale and the y-axis of the urine plot.

The software shall indicate that the diuretic infusing device, urine monitor device and/or the hydration fluid source are connected to the console(s) housing the computer control system.

The software shall indicate that the diuretic dispensing device, e.g., a infusion syringe for dispensing a diuretic, is connected.

Keys

The software shall provide a button to allow the user to start therapy.

The software shall provide a button to allow the user to stop therapy.

The software shall provide a button to allow the user to pause infusion.

The software shall provide a button to allow the user to stop the ramp and go to continuous infusion.

The software shall provide a button to allow the user to enable manual control of the diuretic infusion rate.

The software shall provide a control to allow the user to adjust the diuretic pump rate in milliliters/hour.

The software shall provide a means to allow the user to confirm error messages.

The software shall provide a means to allow the user to reset a serial port for the syringe infusion system.

The software shall provide a means to allow the user to reset one or more serial ports on the console(s) housing the computer system, wherein the ports are to connected to one or more of the urine monitoring device, the diuretic dispensing device and the hydration fluid source or dispensing device.

The software shall provide a means to allow the user to initiate Ramp mode.

The software shall provide a means to allow the user to Download an event log from the computer system.

Settings

The software shall allow the user to set the following parameters:

Urine Buffer Range (ml/hr)—the rate above the "Desired Fluid Balance"*(−1) used as a target. Default value: 100 ml/hr.

Urine Rate Target (ml/hr)—urine rate target during the ramp phase. Default value: 525 ml/hr.

Debt Threshold (ml/hr)—urine rate below which debt is calculated. Default value: 325 ml/hr.

Mode Control

Ramp Mode:

The software shall provide a Ramp mode, that begins when the user initiates Diuretic Management.

If NO file input is selected by the user upon initiation of the diuretic infusion, the IV Infusion of the diuretic shall exponentially ramp following a log base 2 curve from 0 to the max rate required to infuse 200 mg of Furosemide if given for 60 minutes.

If a file input is selected by the user, the IV infusion shall follow the specified profile.

The IV infusion described in shall be stopped either:

a) when 60 minutes elapse from the start of ramp without reaching the target urine rate

OR b) when the console measured Urine Production Rate is higher or equal to the user adjustable target urine rate (default 525 ml/h). The software shall then wait 10 minutes and monitor the urine output rate. During this time, the software shall set the diuretic pump rate to 20% of the currently delivered dose. If the urine output rate remains above 525 ml/hr, the software shall enter Continuous Infusion mode, if the urine rate is now below 525 ml/hr, the ramp shall resume for at least 5 minutes.

OR c) per user request

When the Ramp completes, the software shall enter continuous infusion.

Pause:

During the ramp phase, the user shall be provided with the option to pause the IV infusion. Upon requesting the IV infusion to resume the IV infusion shall start at the rate at which it was paused and follow the selected IV infusion pattern for the time remaining until the conclusion of 60 minutes.

Continuous Infusion:

Once the ramp completes, the system shall continue to administer a continuous diuretic IV infusion rate based on the formula below:

Infusion rate (mg/hour)=0.2*(total amount of diuretic infused during the ramp phase in mg that corresponds with the minute of the ramp that was completed)

If the infusion rate calculated in the previous step is less than 4 mg/hr, it will be set to 4 mg/hr.

During continuous infusion mode, the system shall monitor the patient's urine output to determine if Ramp mode or Downtitrate mode criteria have been met.

If the urine output is consistently above 625 ml/hr for 3 hours, and the slope of the urine rate over the previous 2 hours predicts that the urine the urine output will be above 625 ml/hr in three hours, the software shall enter Downtitrate mode.

If the average urine output is below the Urine Buffer Range+Net Target (default 325 ml/hr) for three hours, or if the accumulated debt over the previous 3 hours exceeds 150 ml, the software shall re-enter ramp mode. Debt shall be defined as the area below the Debt Threshold (default value 325 ml/hr) and above the urine rate when the urine rate is below the debt threshold. Ramp mode shall resume at the minute in the ramp phase that corresponds with the current infusion rate (Ramp Total=infusion rate/0.2)

The Ramp mode shall not be entered if the urine output in the previous 15 minutes is less than 25 ml (100 ml/hr).

The Ramp mode shall not be entered if the current infusion rate corresponds with 55 minutes of the ramp or greater.

Downtitrate:

If Downtitrate mode is initiated, the software shall set the pump speed to 0.4 ml/hr for up to 50 minutes.

If those 50 minutes complete without the urine rate dropping below 525 ml/hr, the software shall resume the continuous infusion at 75% of the rate prior to the initiation of down titration (a 25% reduction in the rate).

If during those 50 minutes, the urine output drops below 525 ml/hr, the software shall resume infusion at a rate calculated as follows:

New infusion rate=previous infusion rate*(1−0.25*(minute urine rate dropped below 525)/50)

Re-ramp:

The software shall provide a means to allow the user to re-initiate Ramp mode.

When the Ramp restarts, it shall continue for at least 5 minutes.

When the Ramp restarts, it shall continue restart at the minute of the ramp corresponding to the current continuous infusion rate (as in, it should restart at the minute in the ramp where the ramp ending would result in the continuous infusion rate currently set).

The ramp shall continue the exponential ramp from the initial ramp.

When the urine production rate reaches the target urine rate (525 ml/hr), the software shall switch to the continuous infusion rate that corresponds to the current minute of the total ramp (i.e. if the re-ramp starts at minute 25, and runs for 10 minutes, the continuous infusion rate shall be set to the same rate as it would have had the initial ramp run for 35 minutes).

If the ramp is Restarted, the debt shall be reset to 0 and the 3 hour average urine rate timer shall be reset.

Manual:

The software shall provide a mode to allow the user to set the diuretic infusion rate.

The units of diuretic infusion setting shall be in ml/hr.

The increments of the diuretic infusion setting shall be 0.1 ml/hr

The minimum value shall be 0.4 ml/hr.

The maximum value shall be 4.0 ml/hr.

The user shall have the option of enabling and disabling the diuretic control algorithm to operate while in manual mode.

Off:

The software shall provide an "off" mode, during which time Diuretic management is stopped, and the diuretic dispensing device, e.g., Gaseby™ infusion syringe, is stopped.

When the user turns the Diuretic management back on, control shall resume where it was prior to entry to "Off" mode.

Monitoring & Protection Functions

The software shall inform the user if there is an alarm on the diuretic dispensing device, e.g., Gaseby™ infusion syringe.

The software shall inform the user if the diuretic dispensing device, e.g., Gaseby™ infusion syringe pump, is disconnected.

The software shall inform the user if the system is not in Run mode.

The software shall inform the user if the urine rate over the previous 15 minutes is below the limit to enable When the diuretic dispensing device, e.g., Gaseby™ infusion syringe pump, goes into alarm mode, the application shall wait for the alarms to be manually cleared and consequently set the pump infusion rate to the previous value and mode.

When a different diuretic dispensing device, e.g., Gaseby™ infusion syringe pump, infusion rate is detected than the one requested by the application, the application shall stop the pump and notify the user.

Exemplary software code for the hydration fluid control component of the algorithm is as follows:

```
static void calcNetGain( float period_urine_delta )
{
  float setting= 0.0;
  float netGain_mlphr;
    //float maxFluidLossRate;
  //float excessUrineOutput; //urine output over and above the max loss rate, in ml/hr
    float pMatchSetting;
  //float urine_rate_exceeding_net_gain;
  float percent_match_adjustment_to_target;
  float fullMatchLimit, urine_rate_exceeding_full_match_limit;
  float fullMatchRange ; //
  float initalBalanceVolume;
  //float kvo_setting;
  float desired_fluid_loss_rate;
  float fluid_match_rate;
    netGain_mlphr = getUserSetting( DESIRED_BALANCE_SETTING );
    pMatchSetting = getUserSetting( PERCENT_MATCH_SETTING );
      fullMatchRange = getUserSetting( PCT100_MATCH_RANGE_SETTING );
```

-continued

```
        initalBalanceVolume = getUserSetting( INITIAL_FLUID_MATCH_SETTING );
        maxHourlyInfusion = getUserSetting( HOURLY_INFUSION_LIMIT_SETTING )
        if ( netGain_mlphr >= 0 )
        {
        setting = ( float ) ( ( ( double ) netGain_mlphr * ( double ) FlowControlInterval )
/3600.0 ); //convert from ml/hr to ml/s
        if ( (pMatchSetting >= 0) && (pMatchSetting < 100)) //apply percent match if it's
set and negative net gain is not
        {
          setting-= period_urine_delta * ( (100-pMatchSetting) / 100 );
        }
        fluid_match_rate = LightUrineRate + (setting)*3600.0/( double )
        if ( fluid_match_rate > maxHourlyInfusion)//if the current setting exceeds the
current max hourly rate, clip it to the max hourly rate
        {
          desired_fluid_loss_rate = (-1.0)*(LightUrineRate - maxHourlyInfusion); //rate
of fluid loss in ml/hr
          setting = ((desired_fluid_loss_rate* ( double ) FlowControlInterval) / 3600.0 );
//convert from ml/hr to ml/s
        }
        }
        else if( (control_data.accumulated_urine_weight > initalBalanceVolume ) ||
( GetRunModeTime( ) > 3600 ) ) //only use negative net gain if 500 ml volume reached
or 60 minutes
        {
        fullMatchLimit = abs( netGain_mlphr ) + fullMatchRange; // calculate rate where
percent match begins
        if ( LightUrineRate > abs( netGain_mlphr ) ) //urine rate if above the max net
gain
        {
          if ( LightUrineRate < fullMatchLimit ) //if in full match range, take off net
gain, but nothing else
          {
            setting = ( float ) ( ( ( double ) ( netGain_mlphr ) * ( double )
FlowControlInterval ) / 3600.0 ); //convert from ml/hr to ml/s
          }
          else
          {
            urine_rate_exceeding_full_match_limit = LightUrineRate - fullMatchLimit;
//calculate the amount of urine exceeding full match limit
            percent_match_adjustment_to_target = urine_rate_exceeding_full_match_limit
* ( (100-pMatchSetting) / 100 );
            setting = ( float ) ( ( ( double ) ( netGain_mlphr - percent_match_adjustment
to__target ) * ( double ) FlowControlInterval ) / 3600.0 ); //convert from ml/hr to ml/s
          }
          fluid_match_rate = LightUrineRate +
(setting)*3600.0/( double )FlowControlInterval; //setting is negative- calculate rate of
replacement with current setting
          if ( fluid_match_rate > maxHourlyInfusion)//if the current setting exceeds the
current max hourly rate, clip it to the max hourly rate
          {
            desired_fluid_loss_rate = (-1.0)*(LightUrineRate - maxHourlyInfusion);
//rate of fluid loss in ml/hr
            setting = ((desired_fluid_loss_rate* ( double ) FlowControlInterval ) /
3600.0 ); //convert from ml/hr to ml/s
          }
        }
        else
        {
          //if urine rate is below desired fluid balance, take the urine rate off of the target
          setting = -( ( ( double ) LightUrineRate * ( double ) FlowControlInterval ) /
3600.0 ); //convert from ml/hr to ml/s
        }
        // increment get gain by the user setting for this interval
      }
      control_data.net_gain_target += setting;
} // end func calcNetGain()
```

VII. Conclusion

It will be apparent to those having skill in the art that changes may be made to the details of the above-described embodiments without departing from the underlying principles of the present technology. In some cases, well known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

Unless otherwise indicated, all numbers expressing concentrations, shear strength, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples may be combined in any combination, and placed into a respective independent example. The other examples can be presented in a similar manner.

1. A system for removing fluid from a patient, comprising:
   - a console housing a computer controller;
   - a urine output device for measuring a rate or volume of urine production of the patient;
   - a first infusion pump configured to pump a hydration fluid into the patient; and
   - a second infusion pump configured to pump a diuretic medication into the patient;
   - wherein the controller is configured to:
     - receive urine output data from urine output device;
     - control the first infusion pump to deliver to the patient a first desired infusion rate of the hydration fluid while simultaneously controlling the second infusion pump to progressively increase a dosage of the diuretic medication;
     - determine a second desired infusion rate of the hydration fluid, lower than the first desired infusion rate, wherein the second desired infusion rate is dependent on the rate and/or the volume of urine production; and
     - control the first infusion pump to deliver the second desired infusion rate of the hydration fluid while simultaneously controlling the second infusion pump to infuse a substantially constant dosage of the diuretic medication.

2. The system of clause 1, wherein the controller is further configured to progressively increase the dosage of the diuretic medication in periodic steps, wherein each step is a greater dosage increase than a prior step.

3. The system of clause 1 or 2, wherein the controller is further configured to progressively increase the dosage of the diuretic medication in accordance with a linear mathematical function.

4. The system of clause 1 or 2, wherein the controller is further configured to progressively increase the dosage of the diuretic medication in accordance with an exponential mathematical function.

5. The system of clause 4, wherein the mathematical function is a first order exponential function.

6. The system of any of the preceding clauses, wherein the controller is further configured to determine the constant dosage of the diuretic medication based on a total amount of the diuretic medication given while controlling the second infusion pump to progressively increase the dosage of the diuretic medication.

7. A system configured to administer a diuretic and a hydration fluid to a patient, a console housing a computer controller;
   - a urine output device for measuring a rate or volume of urine production of the patient;
   - a first infusion pump configured to pump a hydration fluid into the patient;
   - a second infusion pump configured to pump a diuretic medication into the patient;
   - wherein the controller is configured to:
     - control the second infusion pump to infuse a diuretic into the patient,
     - control the first infusion pump to pump a hydration fluid containing sodium chloride into the patient, and
     - monitor urine output by the patient,
     - wherein the control of the first infusion pump includes automatically adjusting a rate of the hydration fluid infused into the patient in response to changes in the urine output by the patient.

8. The system of clause 7, wherein the automatic adjustment of the rate of the hydration fluid includes adjusting the rate of the hydration fluid to substantially match the urine output while the urine output is below a first threshold, and to be less than the urine output while the urine output is above the first threshold.

9. The system of clause 8, wherein the first threshold is in at least one range of 350 ml/hour to 550 ml/hour, 375 ml/hour to 475 ml/hr, 400 ml/hr to 450 ml/hr or within 5% of 425 ml/hour.

10. The system of clause 8 or 9, wherein the automatic adjustment of the hydration fluid includes setting the hydration fluid to a fraction of a current rate of urine output while the urine output is above the first threshold, wherein the fraction is in a range of 70% to 30%, 60% to 40%, or 45% to 55% of the current rate of the urine output.

11. The system of any of clauses 7 to 10, wherein the automatic adjustment of the rate of the hydration fluid includes adjusting the rate of the hydration fluid to substantially a constant hydration fluid rate while the urine output exceeds a second threshold.

12. The system of clause 10 wherein the second threshold is above at least one of 800 ml/hour, 900 ml/hour, 1000 ml/hour, 1025 ml/hour, 1100 ml/hour, or 1200 ml/hour.

13. The system of any of clauses 7 to 12, further comprising automatically adjusting a rate of the infusion of the diuretic into the patient during at least one period while the urine output is below a third threshold.

14. A method to treat a patient suffering from fluid overload, comprising:
- causing a diuretic to be administered to the patient to increase urine output of the patient;
- determining urine output by the patient while causing the diuretic to be administered;
- infusing a hydration fluid into the patient; and
- automatically adjusting a rate of the hydration fluid infused into the patient to achieve a desired net fluid loss in the patient.

15. The method of clause 14, wherein the automatic adjustment of the rate of the hydration fluid is calculated based on a difference between the urine output and the desired net fluid loss.

16. The method of clause 14 or 15, wherein the automatic adjustment of the rate of the hydration fluid is calculated based on a current rate increase of the urine output.

17. The method of any clauses 14 to 16, wherein the automatic adjustment of the rate of the hydration fluid reduces a rate or rate of increase of the hydration fluid in response to the urine output exceeding a first threshold output.

18. The method of clause 16, wherein the first threshold output is a rate of urine output.

19. The method of any of clauses 14 to 18, wherein the automatic adjustment of the rate of the hydration fluid includes increasing the rate of the hydration fluid to a rate within ten percent (10%) of a current rate of urine output, until the current rate of urine output reaches a first threshold output.

20 The method of clause 19, wherein the first threshold output is a urine output rate in a range of 200 ml/hr to 240 ml/hr.

21. The method of any of clauses 14 to 20, further comprising limiting a rate of the hydration fluid infusion to a maximum limit for the hydration fluid while a current urine output rate is above a second threshold is above 500 ml/hr, above 700 ml/hr, or above 1020 ml/hr.

22. The method of any of clauses 14 to 21, further comprising stopping the method when the net fluid loss reaches a desired amount for the net fluid loss, such as 5 liters, 8 liters or 10 liters.

23. The method of any of clauses 14 to 22, further comprising automatically adjusting the diuretic administered to the patient based on the urine output.

24. The method of clause 23, wherein the automatic adjustment of the diuretic includes increasing a rate of the diuretic being administered until the urine output reaches a desired minimum urine value.

25. The method of clause 24, wherein the minimum urine value is a minimum urine output rate.

26. The method of any of clauses 23 to 25, wherein the step of adjusting the diuretic includes automatically increasing the diuretic level at intervals of five minutes or less until the urine output reaches the desired minimum urine value.

27. The method of clause 26, wherein at least one of the increases in the diuretic level is a greater increase than the immediately prior increase.

28. The method of clauses 26 or 27, wherein each of the increases in the diuretic level is greater than the increase of the immediately prior increase.

29. The method of any of clauses 14 to 28, wherein the automatic adjustment of the diuretic includes:
- calculating a reduced rate for the diuretic in response to the urine output reaching the desired minimum urine value or rate, wherein the reduced rate is below and based on a value of the diuretic administered when the urine output reached the desired minimum urine value or rate, and
- administering the diuretic at the reduce rate for a period of at least one hour.

30. A fluid management system, comprising:
- a hydration fluid pump configured to pump a hydration fluid into a patient;
- a diuretic pump configured to pump a diuretic into the patient;
- a measurement device configured to measure urine output of the patient;
- a computer configured to:
  - determine an amount or rate of urine output of the patient;
  - automatically inject a diuretic to the patient by controlling the diuretic pump to deliver the diuretic at a dosage rate determined by the computer;
  - automatically infuse an amount or rate of a hydration fluid into the patient by controlling the hydration fluid pump; and
  - automatically adjust the rate or the amount of the hydration fluid infused into the patient to achieve a desired amount or rate of net fluid loss in the patient.

31. The fluid management system of clause 30, wherein the computer is configured to determine the automatic adjustment of the amount or rate of the hydration fluid based on a difference between the respective amount or rate of urine output and the desired net fluid loss.

32 The fluid management system of clause 30 or 31, wherein the automatic adjustment of the rate of the hydration fluid is calculated based on a current rate increase of the urine output.

33. The fluid management system of any of clauses 30 to 32, wherein the automatic adjustment of the rate of the hydration fluid reduces a rate increase of the hydration fluid in response to the urine output exceeding a first threshold output.

34. The fluid management system of any of clauses 30 to 33, wherein the first threshold output is a rate of urine output.

35. The fluid management system of any of clauses 30 to 34, wherein the automatic adjustment of the rate of the hydration fluid includes increasing the rate of the hydration fluid to a rate within ten percent (10%) of a current rate of urine output, until the current rate of urine output reaches a first threshold output.

36. The fluid management system of any of clauses 30 to 35, wherein the first threshold output is a urine output rate in a range of 200 ml/hr to 240 ml/hr.

37. The fluid management system of any of clauses 30 to 36, further comprising limiting a rate of the hydration fluid infusion to a maximum limit for the hydration fluid while a current urine output rate is above a second threshold is above 500 ml/hr, above 700 ml/hr, or above 1020 ml/hr.

38. The fluid management system of any of clause 37, wherein the computer is further configured to maintain the rate of the hydration fluid infusion at the maximum limit while the urine output exceeds a maximum threshold urine output rate.

39. The fluid management system of any of clauses 30 to 38, further comprising ceasing to automatically inject the diuretic when the net fluid loss reaches a desired amount for the net fluid loss, such as 5 liters, 8 liters or 10 liters.

40. The fluid management system of any of clauses 30 to 39, wherein the computer is further configured to stop the administration of the diuretic when the fluid loss reaches a desired amount for the net fluid loss.

41. The fluid management system of any of clauses 30 to 40, wherein the computer is configured to automatically adjust the diuretic administered to the patient based on the urine output.

42. The fluid management system of any of clauses 30 to 41, wherein the automatic adjustment of the diuretic includes increasing a rate of the diuretic being administered until the urine output reaches a desired minimum urine value.

43. The fluid management system of any of clauses 30 to 42, wherein the minimum urine value is a minimum urine output rate.

44. The fluid management system of any of clauses 30 to 43, wherein the adjustment of the diuretic includes automatically increasing the diuretic level at intervals of five minutes or less until the urine output reaches the desired minimum urine value.

45. The fluid management system of clause 44, wherein at least one of the increases in the diuretic level is a greater increase than the immediately prior increase.

46. The fluid management system of clause 44 or 45, wherein each of the increases in the diuretic level is greater than the increase of the immediately prior increase.

47. The fluid management system of any of clauses 30 to 46, wherein the automatic adjustment of the diuretic includes:

calculating a reduced rate for the diuretic in response to the urine output reaching the desired minimum urine value or rate, wherein the reduced rate is below and based on a value of the diuretic administered when the urine output reached the desired minimum urine value or rate, and administering the diuretic at the reduce rate for a period of at least one hour.

48. A method for providing fluid therapy, the method comprising:

obtaining a urine output rate from a patient;

causing a diuretic to be provided to the patient at a dosage rate;

causing a hydration fluid to be provided to the patient at a hydration rate no more than the urine output; and adjusting at least one of the dosage rate of the diuretic or the hydration rate of the hydration fluid, thereby causing net fluid loss from the patient.

49. The method of any one of the clauses herein, wherein adjusting the dosage rate of the diuretic comprises increasing the dosage rate until (i) a predetermined period of time has elapsed, (ii) the urine output rate is above a first predetermined threshold, (iii) a total amount of the diuretic provided is above a second predetermined threshold, and/or (iv) the dosage rate is above a third predetermined threshold.

50. The method of clause 49, wherein the first predetermined threshold is at least 150 ml/hour, 200 ml/hour, 250 ml/hour, 300 ml/hour, 350 ml/hour, 400 ml/hour, 450 ml/hour, 500 ml/hour, or 525 ml/hour.

51. The method of any one of clauses 49 or 50, wherein the second predetermined threshold is at least 100 mg, 150 mg, 200 mg, or 250 mg.

52. The method of any one of clauses 49-51, wherein the third predetermined threshold is at least 20 mg/hour, 30 mg/hour, 40 mg/hour, or 50 mg/hour.

53. The method of any one of clauses 49-52, wherein the predetermined period of time is at least 20 minutes, 30 minutes, 40 minutes, or 60 minutes.

54. The method of any one of the clauses herein, wherein causing the diuretic to be provided comprises causing the diuretic to be provided in incrementally-increasing dosages, such that each of the dosages is greater than the immediately previous dosage.

55. The method of any one of the clauses herein, wherein causing the diuretic to be provided comprises causing the diuretic to be provided in recurring and increasing dosages, such that the dosage rate is doubled in a time period no more than 20 minutes, 15 minutes, or 10 minutes.

56. The method of any one of the clauses herein, wherein causing the diuretic to be provided comprises causing the dosage rate of the diuretic to increase exponentially.

57. The method of any one of the clauses herein, wherein causing the diuretic to be provided comprises causing the diuretic to be provided in continuously increasing dosages until at least one of a predetermined time period elapses or a threshold urine rate is exceeded.

58. The method of any one of the clauses herein, wherein causing the diuretic to be provided comprises iteratively increasing the dosage rate such that the diuretic rate or amount provided to the patient increases by at least 50%, 100%, or 150%, relative to a previous dosage rate, after a set period of time, the set period of time being no more than 15 minutes, 20 minutes, or 30 minutes.

59. The method of any one of the previous clauses, wherein causing the diuretic to be provided to the patient comprises increasing the dosage rate of the diuretic such that the urine output rate is above a predetermined threshold, and wherein adjusting the dosage rate comprises decreasing the dosage rate such that a value of the decreased dosage rate is a percentage of a value of a total amount of the diuretic provided to the patient.

60. The method of any one of the previous clauses, wherein causing the diuretic to be provided comprises causing the diuretic to be provided such that the urine output rate is above a predetermined threshold, the method further comprising:

after causing the diuretic to be provided, determining that the urine output rate is less than a predetermined threshold; and requesting confirmation from a user or the patient to increase the diuretic rate.

61. The method of clause 60, further comprising:

receiving confirmation from the user or the patient to increase the diuretic rate; and only after receiving the confirmation, increasing the dosage rate.

62. The method of clause 61, wherein increasing the dosage rate comprising increasing the dosage rate until the urine output rate rises above the predetermined threshold.

63. The method of any one of the previous clauses, wherein causing the diuretic to be provided comprises causing the diuretic to be provided such that the urine output rate is above a predetermined threshold, the method further comprising:

after causing the diuretic to be provided, determining that average urine output rate over a period of time is less than a desired threshold, the period of time being at least one hour and the desired threshold being at least 300 ml/hr; and increasing the dosage rate at least until the urine output rate is greater than the predetermined threshold.

64. The method of any one of the clauses herein, wherein causing the hydration fluid to be provided to the patient at the hydration rate comprises causing the hydration rate to be provided such that the hydration rate substantially matches the urine output rate at least until a first amount of hydration fluid is infused, the first amount being at least 200 ml or 250 ml.

65. The method of any one of the clauses herein, wherein causing the hydration fluid to be provided to the patient at the hydration rate comprises causing the hydration rate to be provided such that the hydration rate substantially matches the urine output rate for at least an initial infusion time, the initial infusion time being 60 minutes.

66. The method of any one of the clauses herein, wherein adjusting at least one of the dosage rate of the diuretic or the hydration rate of the hydration fluid comprises increasing the dosage rate of the diuretic and increasing the hydration rate of the hydration fluid, wherein increasing the hydration rate comprises setting the hydration rate of the hydration fluid based on the urine output rate, such that— if the urine output rate is below a first threshold, the hydration rate is set to zero or less than 20 ml/hr; and if the urine output rate is between a second threshold and the first threshold, the hydration rate is set to 75%-125% of the urine output rate between the second threshold and the first threshold.

67. The method of any one of the clauses herein, wherein adjusting at least one of the dosage rate of the diuretic or the hydration rate of the hydration fluid comprises increasing the dosage rate of the diuretic and increasing the hydration rate of the hydration fluid, wherein increasing the hydration rate comprises setting the hydration rate of the hydration fluid based on the urine output rate, such that— if the urine output rate is below a first threshold, the hydration rate is set to zero or less than 20 ml/hr;

if the urine output rate is between a second threshold and the first threshold, the hydration rate is set to a first rate equal to 100% or 75%-125% of the urine output rate between the second threshold and the first threshold; and if the urine output rate is between a third threshold and the second threshold, the hydration rate is set to a sum of the (i) first rate and (ii) 50% or 25% to 75% of the urine output rate between the third threshold and the second threshold.

68. The method of any one of the clauses herein, wherein adjusting at least one of the dosage rate of the diuretic or the hydration rate of the hydration fluid comprises increasing the dosage rate of the diuretic and increasing the hydration rate of the hydration fluid, wherein increasing the hydration rate comprises setting the hydration rate of the hydration fluid based on the urine output rate, such that— if the urine output rate is below a first threshold, the hydration rate is set to zero or less than 20 ml/hr;

if the urine output rate is between a second threshold and the first threshold, the hydration rate is set to a first rate equal to 100% or 75%-125% of the urine output rate between the second threshold and the first threshold;

if the urine output rate is between a third threshold and the second threshold, the hydration rate is set to a sum of the (i) first rate and (ii) a second rate equal to 50% or 25% to 75% of the urine output rate between the third threshold and the second threshold; and if the urine output rate is above the third threshold, the hydration rate is set to a sum of the first rate and the second rate.

69. The method of any one of the clauses herein, wherein the first threshold is no more than 100 ml/hour, 125 ml/hour, 150 ml/hour, 175 ml/hour, 200 ml/hour, 225 ml/hour, or 250 ml/hour.

70. The method of any one of the clauses herein, wherein the second threshold is no more than 300 ml/hour, 325 ml/hour, 350 ml/hour, 375 ml/hour, 400 ml/hour, 425 ml/hour, or 450 ml/hour.

71. The method of any one of the clauses herein, wherein the third threshold is no more than 800 ml/hour, 850 ml/hour, 900 ml/hour, 950 ml/hour, 1000 ml/hour, 1025 ml/hour, or 1050 ml/hour.

72. The method of any one of the clauses herein, further comprising, if the urine output rate is above a urine output threshold for a predetermined period of time, decreasing the dosage rate of the diuretic based on a down-titration algorithm, the urine output threshold being at least 500 ml/hour, 525 ml/hour, 550 ml/hour, 1000 ml/hour, 1025 ml/hour, or 1050 ml/hour, the predetermined period of time being at least 2 hours, 3 hours, or 4 hours.

73. The method of any one of the clauses herein, further comprising, if the urine output rate is above a urine output threshold for a predetermined period of time, decreasing the dosage rate of the diuretic by a percentage, the percentage being at least 10%, 25%, or 40%, the urine output threshold being at least 500 ml/hour, 525 ml/hour, 550 ml/hour, 1000 ml/hour, 1025 ml/hour, or 1050 ml/hour, the predetermined period of time being at least 2 hours, 3 hours, or 4 hours.

74. The method of any one of clauses 72 or 73, wherein decreasing the dosage rate comprises decreasing the dosage rate of the diuretic until the urine output rate is equal to or less than a down-titration threshold, the down-titration threshold being at least 50 ml, 100 ml, 150 ml, or 200 ml less than the urine output threshold.

75. The method of any one of the clauses herein, wherein adjusting at least one of the dosage rate comprises decreasing the dosage rate of the diuretic based on a down-titration algorithm if any one or two or all of a set of conditions is met, the set of conditions including— the urine output rate is above a predetermined rate for a predetermined period of time, the predetermined rate being at least 500 ml/hour, 750 ml/hour, or 1000 ml/hour, the predetermined period of time being at least 1 hour, 2 hours, or 3 hours;

a rate of change in the urine output rate is above a predetermined rate for a predetermined period of time, the predetermined rate being at least 30 ml/hour$^2$, 40 ml/hour$^2$, or 50 ml/hour$^2$, the predetermined period of time being of at least 1 hour, 2 hours, or 3 hours; and the dosage rate of the diuretic is above a predetermined rate, the predetermined rate being at least 5 mg/hour, 10 mg/hour or 15 mg/hour.

76. The method of any one of the previous clauses, wherein an average net fluid loss rate from the patient is at least 50 ml/hour, 75 ml/hour, 100 ml/hour, 125 ml/hour, 150 ml/hour, 175 ml/hour, or 200 ml/hour.

77. The method of any one of the previous clauses, wherein an average net fluid loss amount from the patient over a day is at least 3 L, 4 L, or 5 L.

78. The method of any one of the previous clauses, further comprising:

after causing the diuretic to be provided, determining that the urine output rate is less than a desired threshold; and after determining that the urine output rate is less than the desired threshold, determining whether the blood pressure of the patient is below a first predetermined threshold and/or the electrolyte level of the patient is below a second predetermined threshold.

79. The method of any one of the previous clauses, wherein the diuretic is a first diuretic, the method further comprising:

after causing the first diuretic to be provided, determining that the urine output rate is less than a desired threshold; and causing a second diuretic, different than the first diuretic, to be provided to the patient.

80. The method of any one of the previous clauses, wherein obtaining the urine output rate comprises determining urine output based on at least one of an optical sensor, a ultrasound sensor, or thermistor.

81. The method of any one of the previous clauses, wherein adjusting at least one of the dosage rate of the diuretic or the hydration rate of the hydration fluid is based on a conductivity, potassium concentration, and/or magnesium concentration of urine from the patient.

82. The method of any one of the clauses herein, wherein causing the hydration fluid to be provided to the patient at the hydration rate causes a urine salt concentration of the patient to increase, and wherein adjusting at least one of the dosage rate or the diuretic or the hydration rate of the hydration fluid causes the urine salt concentration of the patient to decrease.

83. The method of any one of the clauses herein, wherein causing the hydration fluid to be provided to the patient at the hydration rate causes a salt concentration of the patient to increase, and wherein adjusting at least one of the dosage rate or the diuretic or the hydration rate of the hydration fluid causes the salt concentration of the patient to decrease.

84. The method of any one of the clauses herein, further comprising determining whether the patient is diuretic resistant.

85. A method for providing fluid therapy, the method comprising:

obtaining a urine output rate from a patient;

causing a diuretic to be provided to the patient at a dosage rate such that the urine output rate is above a predetermined threshold;

causing a hydration fluid to be provided to the patient at a hydration rate no more than the urine output;

determining whether any one of a predetermined set of conditions is met; and if at least one of the set of conditions is met, decreasing the dosage rate of the diuretic by a predetermined amount.

86. The method of any one of the clauses herein, wherein the predetermined amount is at least 15%, 20%, or 25%, or between 10-40%.

87. The method of any one of the clauses herein, wherein decreasing the dosage rate of the diuretic comprises decreasing the dosage rate of the diuretic by the predetermined amount for a predetermined period of time of at least 1 hour, 2 hours, or 3 hours.

88. The method of any one of the clauses herein, further comprising, after decreasing the dosage rate of the diuretic, setting the dosage rate based on an algorithm.

89. The method of any one of the clauses herein, wherein determining whether any one of predetermined set of condition is met includes determining whether the urine output rate is above a predetermined rate for a predetermined period of time, the predetermined rate being at least 500 ml/hour, 750 ml/hour, 1000 ml/hour, the predetermined period of time being of at least 1 hour, 2 hours, or 3 hours.

90. The method of any one of the clauses herein, wherein determining whether any one of predetermined set of condition is met includes determining whether a rate of change in the urine output rate is above a predetermined rate for a predetermined period of time, the predetermined rate being at least 30 ml/hour$^2$, 40 ml/hour$^2$, or 50 ml/hour$^2$, the predetermined period of time being of at least 1 hour, 2 hours, or 3 hours.

91. The method of any one of the clauses herein, wherein determining whether any one of a predetermined set of condition is met includes determining whether the dosage rate of the diuretic is above a predetermined rate, the predetermined rate being at least 5 mg/hour, 10 mg/hour or 15 mg/hour.

92. Tangible, non-transitory computer-readable media having instructions that, when executed by one or more processors, causes a computing device to perform operations comprising the method of any one of the clauses herein.

93. A fluid therapy system, comprising:

a urine measurement device configured to measure urine output from a patient;

a pump configured to be fluidly coupled to a source of diuretic and provide the diuretic to the patient;

one or more processors; and tangible, non-transitory computer-readable media having instructions that, when executed by the one or more processors, cause the fluid therapy system to perform operations comprising— obtaining a urine output rate from the urine measurement device; and causing the diuretic to be provided, via the pump, to the patient at a dosage rate, such that a dosage volume is increased over a period of time of no more than 120 minutes, wherein an end of the period of time is based at least in part on the urine output rate being above a predetermined threshold.

94. The fluid therapy system of any one of the clauses herein, the operations further comprising, after causing the diuretic to be provided, setting the dosage rate of the diuretic to be a predetermined percentage of a current dosage rate.

95. The fluid therapy system of any one of the clauses herein, the operations further comprising:

determining that the urine output rate is above a predetermined threshold; and setting the dosage rate of the diuretic to be a predetermined percentage of a total amount of the diuretic delivered at the time of determining the urine output rate is above the predetermined threshold.

96. The fluid therapy system of any one of the clauses herein, the operations further comprising:

determining that an average urine output rate measured over a preset time period is above a predetermined threshold; and in response to the determination, decreasing the dosage rate of the diuretic by a predetermined percentage.

97. The fluid therapy system of any one of the clauses herein, the operations further comprising:

determining that one or more of the following set of conditions exists:

(i) an average urine output rate measured over a first preset time period is above a first predetermined threshold;

(ii) the urine output rate measured over a second preset time period is increasing at a rate above a predetermined rate of increase;

(iii) the dosage rate is above a second predetermined threshold; and in response to determining that one or more of the set of conditions exists, decreasing the dosage rate of the diuretic by a predetermined percentage.

98. The fluid therapy system of any one of the clauses herein, wherein the first predetermined threshold is at least 500 mL/hour, the predetermined rate of increase is at least 30 mL/hour$^2$, and the second predetermined threshold is at least 5 mg/hour.

99. The fluid therapy system of any one of the clauses herein, wherein the diuretic is provided such that the dosage rate increases by at least 200% over the period of time.

100. The fluid therapy system of any one of the clauses herein, wherein causing the diuretic to be provided comprises iteratively increasing the dosage rate in an exponential manner.

101. The fluid therapy system of any one of the clauses herein, the operations further comprising:

determining that an average urine output rate measured over a preset time period is below a predetermined threshold; and in response to the determination, iteratively increasing the dosage rate of the diuretic in an exponential manner.

102. The fluid therapy system of any one of the clauses herein, wherein the pump is a first pump, the system further comprising a second pump configured to be operably coupled to a source of hydration fluid and provide the hydration fluid to the patient, the operations further comprising causing the hydration fluid to be provided, via the second pump, to the patient at a hydration rate no more than the urine output rate.

103. The fluid therapy system of any one of the clauses herein, wherein the hydration fluid is provided to the patient such that the hydration rate substantially matches or is within a predetermined percentage of the urine output rate until at least one of (i) a predetermined period of time has elapsed or (ii) a predetermined amount of hydration fluid is infused.

104. The fluid therapy system of any one of the clauses herein, wherein the hydration rate is based on the urine output rate, such that— if the urine output rate is below a first threshold, the hydration rate is set to a first rate; and if the urine output rate is above the first threshold, the hydrate rate is set to a second rate equal to a sum of the first rate and a predetermined percentage of the urine output rate above the first threshold.

105. The fluid therapy system of any one of the clauses herein, wherein the first threshold is no more than 200 mL/hour, the second threshold is no more than 450 mL/hour, and the predetermined percentage is within a range of 25-75%.

106. The fluid therapy system of any one of the clauses herein, wherein the hydration rate is set such that a difference between the hydration rate and the urine output rate increases with as the urine output rate increases, thereby inducing net fluid loss from the patient.

107. The fluid therapy system of any one of the clauses herein, wherein the net fluid loss is at least 200 mL/hour.

108. A console for providing fluid therapy to a patient, the console comprising:

a controller having one or more processors and in communication with— a urine measurement device configured to measure urine output from a patient;

a first pump configured to provide a diuretic to the patient;

a second pump configured to provide a hydration fluid to the patient; and tangible, non-transitory computer-readable media having instructions that, when executed by the one or more processors, cause the fluid therapy system to perform operations comprising— obtaining a urine output rate from the urine measurement device;

causing the diuretic to be provided, via the first pump, to the patient at a dosage rate, such that a dosage volume is increased over a period of time; and causing the hydration fluid to be provided, via the second pump, to the patient at a hydration rate no more than the urine output rate, thereby promoting a net fluid loss from the patient.

109. The console of any one of the clauses herein, the operations further comprising, after causing the diuretic to be provided, setting the dosage rate of the diuretic to be a predetermined percentage of a current dosage rate.

110. The console of any one of the clauses herein, the operations further comprising:

determining that an average urine output rate measured over a preset time period is above a predetermined threshold; and in response to the determination, decreasing the dosage rate of the diuretic by a predetermined percentage.

111. The console of any one of the clauses herein, the operations further comprising:

determining that an average urine output rate measured over a preset time period is below a predetermined threshold; and in response to the determination, increasing the dosage rate of the diuretic.

112. The console of any one of the clauses herein, wherein the hydration fluid is provided to the patient such that the hydration rate substantially matches or is within a predetermined percentage of the urine output rate until at least one of (i) a predetermined period of time has elapsed or (ii) a predetermined amount of hydration fluid is infused.

113. The console of any one of the clauses herein, wherein the hydration rate is set such that a difference between the hydration rate and the urine output rate increases with as the urine output rate increases, thereby inducing net fluid loss from the patient.

114. The console of any one of the clauses herein, wherein the hydration rate is based on the urine output rate, such that— if the urine output rate is below a first threshold, the hydration rate is set to a first rate; and if the urine output rate is above the first threshold, the hydrate rate is set to a second rate equal to a sum of the first rate and a predetermined percentage of the urine output rate above the first threshold.

115. The console of any one of the clauses herein, wherein causing the diuretic to be provided comprises causing the diuretic to be provided such that the dosage rate is iteratively increased in an exponential manner.

116. A fluid therapy method for promoting net fluid loss from a patient, the method comprising:

obtaining a urine output rate from a patient;

causing a diuretic to be provided to the patient at a dosage rate, wherein the dosage rate is increased over a period of time such that the urine output rate increases to be above a predetermined threshold within the period of time;

after the urine output rate increases to be above the predetermined threshold, setting the dosage rate of the diuretic to be a predetermined percentage of the current dosage rate; and causing a hydration fluid to be provided to the patient at a hydration rate.

117. The method of any one of the clauses herein, wherein setting the dosage rate of the diuretic comprises setting the dosage rate of the diuretic to be a predetermined percentage of a total amount of the diuretic delivered to the patient.

118. The method of any one of the clauses herein, wherein causing the diuretic to be provided comprises causing the diuretic to be provided such that the dosage rate is iteratively increased in an exponential manner.

119. The method of any one of the clauses herein, wherein the dosage rate is iteratively increased in the exponential manner for no more than 60 minutes.

120. The method of any one of the clauses herein, further comprising:

determining that an average urine output rate measured over a preset time period is below a predetermined threshold; and in response to the determination, iteratively increasing the dosage rate of the diuretic in an exponential manner.

121. The method of any one of the clauses herein, wherein the hydration fluid is provided to the patient such that the hydration rate substantially matches or is within a predetermined percentage of the urine output rate until at least one of (i) a predetermined period of time has elapsed or (ii) a predetermined amount of hydration fluid is infused.

122. The method of any one of the clauses herein, wherein the hydration rate is based on the urine output rate, such that— if the urine output rate is below a first threshold, the hydration rate is set to a first rate; and if the urine output rate is above the first threshold, the hydrate rate is set to a second rate equal to a sum of the first rate and a predetermined percentage of the urine output rate above the first threshold.

123. The method of any one of the clauses herein, wherein the hydration rate is set such that a difference between the hydration rate and the urine output rate increases with as the urine output rate increases, thereby inducing net fluid loss from the patient.

We claim:

1. A fluid therapy system, comprising:

a urine measurement device configured to measure urine output from a patient;

a pump configured to provide a diuretic to the patient;

one or more processors; and tangible, non-transitory computer-readable media having instructions that, when executed by the one or more processors, cause the fluid therapy system to perform operations comprising— obtaining a urine output rate from the urine measurement device;

causing the diuretic to be provided, via the pump, to the patient at an initial dosage rate; and increasing a dosage rate of the diuretic from the initial dosage rate to additional dosage rates higher than the initial dosage rate over a period of time of 120 minutes, the additional dosage rates including at least:

a first dosage rate higher than the initial dosage rate, a second dosage rate higher than the first dosage rate, and a third dosage rate higher than the second dosage rate.

2. The fluid therapy system of claim 1, the operations further comprising, after increasing the dosage rate, setting the dosage rate of the diuretic to be a nonzero predetermined percentage of a current dosage rate.

3. The fluid therapy system of claim 1, wherein increasing the dosage rate comprises increasing the dosage rate to the additional dosage rates until the urine output rate is above a predetermined threshold, the operations further comprising:

after the period of time, setting the dosage rate of the diuretic to be a nonzero predetermined percentage of a total amount of the diuretic delivered at a time that the urine output rate is determined to be above the predetermined threshold.

4. The fluid therapy system of claim 1, wherein increasing the dosage rate comprises increasing the dosage rate to the additional dosage rates unless the urine output rate is above a predetermined threshold, the operations further comprising:

determining that an average urine output rate measured over a preset time period is above the predetermined threshold; and in response to the determination, decreasing the dosage rate of the diuretic by a nonzero predetermined percentage.

5. The fluid therapy system of claim 1, wherein increasing the dosage rate comprises increasing the dosage rate to the additional dosage rates unless the urine output rate is above a first predetermined threshold, the operations further comprising:

determining that one or more of the following set of conditions exists:

(i) an average urine output rate measured over a first preset time period is above the first predetermined threshold;

(ii) the urine output rate measured over a second preset time period is increasing at a rate above a predetermined rate of increase; or (iii) the dosage rate is above a second predetermined threshold; and in response to determining that the one or more of the set of conditions exists, decreasing the dosage rate of the diuretic by a predetermined percentage.

6. The fluid therapy system of claim 5, wherein the first predetermined threshold is at least 500 mL/hour, the predetermined rate of increase is at least 30 mL/hour$^2$, and/or the second predetermined threshold is at least 5 mg/hour.

7. The fluid therapy system of claim 1, wherein increasing the dosage rate comprises increasing the dosage rate by at least 200% over the period of time.

8. The fluid therapy system of claim 1, wherein the period of time is 60 minutes.

9. The fluid therapy system of claim 1, wherein, in operation, increasing the dosage rate occurs as the urine output rate increases.

10. The fluid therapy system of claim 1, wherein obtaining the urine output rate comprises obtaining the urine output rate every 10 minutes or less.

11. The fluid therapy system of claim 1, wherein a dose for the first dosage rate is immediately subsequent to a dose for the initial dosage rate.

12. The fluid therapy system of claim 1, wherein the first dosage rate occurs within 30 minutes of the initial dosage rate.

13. A fluid therapy system, comprising:

a urine measurement device configured to measure urine output from a patient;

a pump configured to provide a diuretic to the patient;

one or more processors; and tangible, non-transitory computer-readable media having instructions that, when executed by the one or more processors, cause the fluid therapy system to perform operations comprising— obtaining a urine output rate;

causing the diuretic to be provided to the patient at an initial dosage rate; and increasing a dosage rate of the diuretic from the initial dosage rate to three or more additional dosage rates higher than the initial dosage rate over a period of time within 120 minutes, wherein, in operation, an end of the period of time is based at least in part on the urine output rate being above a predetermined threshold.

14. The fluid therapy system of claim 13, the operations further comprising:

determining that an average urine output rate measured over a preset time period is below the predetermined threshold; and in response to the determination, iteratively increasing the dosage rate of the diuretic in an exponential manner.

15. The fluid therapy system of claim 13, wherein increasing the dosage rate comprises iteratively increasing the dosage rate in an exponential manner.

16. The fluid therapy system of claim 15, wherein increasing the dosage rate comprises iteratively increasing the dosage rate such that each dosage rate increase is greater than a previous dosage rate increase.

17. A fluid therapy system, comprising:

a urine measurement device configured to measure urine output from a patient;

a pump configured to provide a diuretic to the patient;

one or more processors; and tangible, non-transitory computer-readable media having instructions that, when executed by the one or more processors, cause the fluid therapy system to perform operations comprising— obtaining a urine output rate from the urine measurement device;

providing an initial dosage rate to the pump; and increasing a dosage rate provided to the pump by repeatedly increasing the dosage rate from the initial dosage rate at least three times for each subsequent dose over a period of time of 120 minutes, until (i) the urine output rate is above a predetermined threshold, (ii) a predetermined amount of time has elapsed since providing the initial dosage rate, and/or (iii) the urine output rate is above the predetermined threshold and the predetermined amount of time has elapsed since providing the initial dosage rate.

18. The fluid therapy system of claim 17, wherein obtaining the urine output rate comprises obtaining the urine output rate every 10 minutes or less.

19. The fluid therapy system of claim 17, wherein the first of the three subsequent doses occurs within 30 minutes of the initial dosage rate.

20. The fluid therapy system of claim 17, wherein the first of the three subsequent doses is immediately subsequent to the initial dosage rate.

* * * * *